(12) United States Patent
Tengler et al.

(10) Patent No.: US 9,072,680 B2
(45) Date of Patent: *Jul. 7, 2015

(54) COMPOSITIONS COMPRISING METHYLPHENIDATE COMPLEXED WITH ION-EXCHANGE RESIN PARTICLES

(71) Applicant: NEOS THERAPEUTICS, LP, Grand Prairie, TX (US)

(72) Inventors: Mark Tengler, Colleyville, TX (US); Russell McMahen, Flower Mound, TX (US)

(73) Assignee: NEOS THERAPEUTICS, LLP, Grand Prairie, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/844,584

(22) Filed: Mar. 15, 2013

(65) Prior Publication Data
US 2014/0037728 A1  Feb. 6, 2014

Related U.S. Application Data

(63) Continuation-in-part of application No. PCT/US2012/044698, filed on Jun. 28, 2012.

(60) Provisional application No. 61/502,189, filed on Jun. 28, 2011, provisional application No. 61/528,554, filed on Aug. 29, 2011.

(51) Int. Cl.
A61K 31/4458 (2006.01)
A61K 9/14 (2006.01)
(Continued)

(52) U.S. Cl.
CPC ............ *A61K 9/5042* (2013.01); *C12N 9/2402* (2013.01); *A61K 9/0056* (2013.01); *A61K 47/48184* (2013.01); *A61K 31/137* (2013.01); *A61K 31/4458* (2013.01); *A61K 9/14* (2013.01); *A61K 47/48853* (2013.01); *A61K 9/5084* (2013.01); *A61K 9/146* (2013.01); *A61K 9/50* (2013.01); *A61K 9/5026* (2013.01); *A61K 9/5047* (2013.01)

(58) Field of Classification Search
None
See application file for complete search history.

(56) References Cited

U.S. PATENT DOCUMENTS 2,099,402 A  11/1937 Keller et al.
2,809,918 A  10/1957 Hermelin
(Continued)

FOREIGN PATENT DOCUMENTS

WO   WO 03/020242    3/2003
WO   WO 2007/109104  9/2007
(Continued)

OTHER PUBLICATIONS

International Search Report, issued Aug. 31, 2012, in PCT/US2012/044698 (published as WO2013003622).
(Continued)

*Primary Examiner* — Michael B Pallay
(74) *Attorney, Agent, or Firm* — Hunton & Williams LLP

(57) ABSTRACT

Pharmaceutical compositions of methylphenidate complexed with ion-exchange resin particles to form drug-resin particles are provided. The compositions have a first plurality of drug-resin particles that are uncoated and a second plurality of drug-resin particles that are coated with a delayed release coating. Preferably, the second plurality of drug-resin particles are coated with a triggered-release coating triggered by a pH change and a diffusion barrier coating.

28 Claims, 41 Drawing Sheets

(51) Int. Cl.
*A61K 47/48* (2006.01)
*A61K 9/50* (2006.01)
*C12N 9/24* (2006.01)
*A61K 9/00* (2006.01)
*A61K 31/137* (2006.01)

(56) References Cited

U.S. PATENT DOCUMENTS

| | | | |
|---|---|---|---|
| 2,990,332 | A | 6/1961 | Keating |
| 3,048,526 | A | 8/1962 | Boswell et al. |
| 3,365,365 | A | 1/1968 | Butler et al. |
| 4,221,778 | A | 9/1980 | Raghunathan |
| 4,619,934 | A | 10/1986 | Sunshine et al. |
| 4,762,709 | A | 8/1988 | Sheumaker |
| 4,775,536 | A | 10/1988 | Patell |
| 4,794,001 | A | 12/1988 | Mehta et al. |
| 4,996,047 | A | 2/1991 | Kelleher |
| 4,999,189 | A | 3/1991 | Kogan et al. |
| 5,158,777 | A | 10/1992 | Abramowitz et al. |
| 5,837,284 | A | 11/1998 | Mehta et al. |
| 5,980,882 | A | 11/1999 | Eichman |
| 6,322,819 | B1 | 11/2001 | Burnside et al. |
| 6,344,215 | B1 | 2/2002 | Bettman et al. |
| 6,605,300 | B1 | 8/2003 | Burnside et al. |
| 6,913,768 | B2 | 7/2005 | Couch et al. |
| 7,101,576 | B2 | 9/2006 | Hovey et al. |
| 8,287,903 | B2 | 10/2012 | Mehta et al. |
| 2002/0058061 | A1 | 5/2002 | Midha et al. |
| 2003/0099711 | A1* | 5/2003 | Meadows et al. ............ 424/474 |
| 2004/0052849 | A1 | 3/2004 | O'hare |
| 2004/0126428 | A1 | 7/2004 | Hughes et al. |
| 2005/0013792 | A1 | 1/2005 | Hollenbeck et al. |
| 2006/0193877 | A1 | 8/2006 | Tengler et al. |
| 2006/0286174 | A1* | 12/2006 | Raman et al. ................ 424/489 |
| 2007/0042955 | A1 | 2/2007 | Mickle et al. |
| 2007/0059270 | A1 | 3/2007 | Hall et al. |
| 2007/0092553 | A1 | 4/2007 | Tengler et al. |
| 2007/0140983 | A1 | 6/2007 | Hall et al. |
| 2007/0148239 | A1 | 6/2007 | Hall et al. |
| 2007/0215511 | A1* | 9/2007 | Mehta et al. ................. 206/531 |
| 2007/0264323 | A1 | 11/2007 | Shojaei et al. |
| 2009/0011027 | A1 | 1/2009 | Pathak et al. |
| 2009/0176884 | A1 | 7/2009 | Dickerson et al. |
| 2009/0221552 | A1 | 9/2009 | Teicher et al. |
| 2010/0104621 | A1 | 4/2010 | Waldo |
| 2010/0166858 | A1 | 7/2010 | Mehta et al. |
| 2010/0278901 | A1 | 11/2010 | Tengler et al. |
| 2012/0015030 | A1 | 1/2012 | Mehta et al. |

FOREIGN PATENT DOCUMENTS

| | | | | |
|---|---|---|---|---|
| WO | WO 2012112140 | A1 * | 8/2012 | ............ A61K 9/50 |
| WO | WO 2013003622 | | 1/2013 | |

OTHER PUBLICATIONS

Prabhu et al., "Comparison of Dissolution Profiles for Sustained Release Resinates of BCS Class 1 Drugs Using USP Apparatus 2 and 4: A Technical Note", *AAPS PharmSciTech*, 9(3): 769-773 (2008).
Hinsvark, et al., *Journal of Phamacokinetics and Biopharmaceutics*, 1(4):319-328, (1973).
Hadzija, *Journal of Forensic Sciences*, 41:878-880 (1996).
Physicians' Desk Reference: Adderall, 51st Ed. (1997).
K. Lehmann, "Coating of Multiparticulates using Polymeric Solutions, Formulations and Process Considerations," in Multiparticulate Oral Drug Delivery, I. Ghebre-Sellassie, Ed., Marcel Dekker, Inc., N.Y., 1994.
Remington: The Science and Practice of Pharmacy, 19th Ed., 1995, vol. II, 1653-1658.
Lin et al., *J. Int. Med. Res.*, 10: 122-125 (1982).
Lin et al., *J. Int. Med. Res.*, 10: 126-128 (1982).
FDA "Guidance for Industry, SUPAC-MR: Modified Release Solid Oral Dosage Forms. Scale-Up and Postapproval Changes: Chemistry, Manufacturing, and Controls; In Vitro Dissolution Testing and In Vivo Bioequivalence Documentation" (Sep. 1997), pp. 1-36.
The United States Pharmacopeia 23, National Formulary 18 (1995), pp. 1791-1799.
Center for Drug Evaluation and Research, "Guidance for Industry: Statistical Approaches to Establishing Bioequivalence" (Jan. 2001), pp. 1-45.
ADDERALL XR® Product Insert. This document is used to illustrate the inherent similarities of ADDERALL® and ADDERALL XR®.
Remington: Pharmaceutical Sciences, 15th Ed., 1975, 1618, 1625-1626.
FDA "Guidance for Industry: Specifications: Test Procedures and Acceptance Criteria for New Veterinary Drug Substances and New medicinal Products: Chemical Substances" (Jun. 14, 2006), pp. 1-35.
Teter et al., "Illicit Methylphenidate Use in an Undergraduate Student Sample: Prevalence and Risk Factors", Pharmacotherapy (2003), vol. 23, No. 5, pp. 609-617.
Kimko et al., "Pharmacokinetics and Clinical Effectiveness of Methylphenidate", Clinical Pharmacokinetics (1999), vol. 37, No. 6, pp. 457-470 (Abstract Only).
Clinical Pharmacology Review for Methylphenidate HCl, NDA #202100, NextWave Pharmaceuticals (2011).
Meyer et al., "FDA's ACPS Meeting, Oct. 2005, Awareness Topic: Mitigating the Risks of Ethanol Induced Dose Dumping from Oral Sustained/Controlled Release Dosage Forms" (2005).
Drug Summary for Quillivant XR, NextWave Pharmaceuticals at PDR.net, accessible at www.pdr.net/drug-summary/quillavant-xr?druglabelid=3038.
ADDERALL XR® Product Insert, registered with the FDA on Aug. 11, 2004.
Lasser et al. "Comparative Efficacy and Safety of Lisdexamfetamine Dimesylate and Mixed Amphetamine Salts Extended Release in Adults with Attention Deficit/Hyperactivity Disorder", *Primary Psychiatry*, 17:44-54 (2010).
Chourasia et al., *J. Pharm. Pharmaceuti. Sci.*, 6:33-66 (2003).
Silver, Larry B., "Medications for ADHD/ADD: Tips for Your Children", accessible at http://www.ldaamerica.org/aboutld/parents/adhd/print_medications.asp (2009).
Spencer et al., "Efficacy of a Mixed Amphetamines Salts Compound in Adults with Attention-Deficit/Hyperactivity Disorder", Arch.Gen. Psychiatry, 58, 775-782 (2001).
National Institute on Drug Abuse, "DrugFacts: Stimulant ADHD Medications-Methylphenidate and Amphetamines", accessible at: http://www.drugabuse.gov/publications/drugfacts/stimulant-adhd-medications-methylphenidate-amphetamines (2009).
Outram, Simon M., "The use of Methylphenidate among students: the future of enhancement?", J. Med. Ethics (2010), vol. 36, pp. 198-202.
Srikanth et al., "Ion-Exchange Resins as Controlled Drug Delivery Carriers", *J. Sci. Res.*, 2:597-611 (2010).
Wick, "Abuse Deterrent Formulations", *Pharmacy Times*, 77:1-6 (2011).

* cited by examiner

Mean d-amphetamine and l-amphetamine Plasma Concentrations Following Administration of ADDERALL XR 20 mg (8 am) and ADDERALL (immediate-release) 10 mg Twice Daily (8 am and 12 noon) in the Fed State.

COMPOSITIONS COMPRISING METHYLPHENIDATE COMPLEXED WITH ION-EXCHANGE RESIN PARTICLES

CROSS-REFERENCE TO RELATED APPLICATIONS

This application is a continuation-in-part of International Application No. PCT/US2012/044698, filed Jun. 28, 2012, which claims priority to U.S. Provisional Application No. 61/502,189, filed Jun. 28, 2011, and U.S. Provisional Application No. 61/528,554, filed Aug. 29, 2011, the disclosures of each of which are hereby incorporated by reference in their entireties.

BACKGROUND OF THE INVENTION (a) Field of the Invention

The invention relates to Attention Deficit Hyperactivity Disorder (ADHD) effective agent dosage forms that both facilitate oral ingestion and provide an effective treatment over a prolonged period of time. In particular, the invention provides for pharmaceutical compositions having a first and second plurality of drug-resin particles, where the first plurality of drug-resin particles does not have a delayed release coating and the second plurality of drug-resin particles does have a delayed release coating, where the drug is an ADHD effective agent and the composition achieves an escalating in vivo plasma concentration of the ADHD effective agent.

(b) Description of the Related Art

Many drug therapies use immediate-release oral dosage forms administered at spaced intervals to provide and maintain a desired therapeutic effect over a prolonged therapy period. For example, drugs used in treating Attention Deficit Disorder (ADD) and ADHD such as ADDERALL® and RITALIN® are administered two or three times a day.

For various reasons, subjects often experience difficulty complying with this administration schedule. In particular, because ADD and ADHD are commonly diagnosed in children, the dosage regimen generally requires that at least one dose is administered during the school day. Children are typically not permitted to self-administer the drug at school. As such, authorized school personnel generally take on the responsibility for administering the drug to children during the school day. However, this approach raises issues of medical privacy and potential stigmatizing of the child by peers. In addition, the compliance issue becomes further complicated as transportation, storage and supply of the drug typically must be documented and/or monitored, and the schedules of the different parties involved, i.e., the child, the educators and the authorized school personnel, must be coordinated and accommodated. The unfortunate result is that doses may be given late or missed altogether resulting in decreased efficacy of the therapy.

To avoid administering multiple doses during the day, once-a-day sustained and extended release medications have been developed. For example, ADDERALL XR®, a mixed amphetamine salts medication, is administered once-a-day for the treatment of ADD and ADHD. To achieve extended release, ADDERALL XR requires a mixture of four amphetamine salts: dextroamphetamine sulfate, dextroamphetamine saccharate, amphetamine aspartate, and amphetamine sulfate. U.S. Pat. Nos. 6,322,819 and 6,605,300, which disclose ADDERALL XR, are hereby incorporated by reference in their entirety. U.S. Pat. No. 6,913,768, which is hereby incorporated by reference, also discloses a four amphetamine salt composition.

METADATE CD® is another once-a-day ADHD treatment. This formulation comprises methylphenidate hydrochloride and achieves an extended-release profile through its make up of 30% immediate release beads and 70% extended release beads.

Prior art ADHD compositions such as ADDERALL XR and METADATE CD are only available in solid dosage forms. Many people, especially children, have difficulty swallowing standard solid dosage forms. Accordingly, there is a need in the art to develop easily ingested, once-daily oral compositions that provide effective, prolonged treatment.

U.S. Pat. No. 2,990,332 to Keating discloses adsorbing amphetamines onto a sulphonic acid cation exchange resin from which the drug is slowly and uniformly released by gastric and intestinal juices. In particular, this patent discloses a homogeneous pharmaceutical drug compound which will immediately release its drug continuously over a long period of time without the necessity of complicated and expensive enteric coating procedures. The amphetamine-resin complex of this patent is such that not more than approximately 50% of the amphetamine is released in one hour by elution with simulated gastric juice and at least approximately 10% in three hours by such elution.

Hinsvark, et al. journal of Phamacokinetics and Biophaaceutics, 1(4):319-328, 1973) reports the comparison of oral bioavailability and pharmacokinetics of between a resin-bound form of amphetamine and the soluble hydrochloride salt. The efficiency of absorption was the same for resinate as for soluble salt, but the speed of absorption was about three times slower for the resinate and blood levels after the resinate reached a lower, later and flatter peak. Without any coating, the resin-bound amphetamine produced more sustained blood levels.

Although, as described by Keating and Hinsvark, amphetamine adsorbed on ion exchange resin was released more slowly into gastric and/or intestinal juices than soluble salts, the pharmacokinetic profile is not comparable to ADDERALL XR or METADATE CD. As such, there is still a need for a once-a-day formulation that is easily ingested.

SUMMARY OF VARIOUS EMBODIMENTS OF THE INVENTION

The invention provides pharmaceutical compositions comprising drug-resin particles comprising at least one ADHD effective agent (e.g., amphetamine, methylphenidate), methods of making such compositions, and methods of treatment using these compositions. In particular, the invention provides for easily ingested, once-daily oral compositions that provide effective, prolonged treatment.

The invention provides various advantage over prior art compositions and methods. For example, the invention provides for liquid drug suspensions, chewable compositions, and orally disintegrating compositions—compositions favored by individuals who have difficulty swallowing conventional solid dosage forms (e.g., children or dysphagic individuals). Moreover, the compositions comprise ion-exchange resins and thus have enhanced taste masking properties as compared to traditional drug formulations. The use of multiple coated resin beads for the controlled release portions of the compositions reduces the risk of dose dumping when the composition is chewed or crushed, because there is no single point where failure of the controlled release mechanism can occur.

In some embodiments, the compositions of the invention are advantageous as compared to currently available amphetamine compositions. For example, the compositions minimize the amount of sulfates, which reduces the likelihood of formation alkyl sulfonates—toxic compounds that the FDA recommends limiting or excluding from drug formulations. Moreover, unlike ADDERALL XR, various compositions of the invention do not require four amphetamine salts. As such, the compositions streamline the supply chain by reducing the number of distinct components required, i.e., simplifies processing and handling.

Also, in the presence of ethanol, the compositions have an improved exposure level of amphetamines and methylphenidate compared to ADDERALL XR and METADATE CD, respectively, i.e., the invention reduces dose dumping when the composition and ethanol are ingested by a subject. For example, the inventors have shown that in the presence of varying concentrations of alcohol (e.g., 4%, 20%, and 40% ethanol) did not significantly alter the rate and extent of absorption of a controlled-release ODT amphetamine composition described herein.

Also in the presence of food, the liquid suspension amphetamine compositions have an increased exposure of amphetamines compared to fed ADDERALL XR during the first four hours or up to the $T_{max}$, i.e., these compositions have less food effect than ADDERALL XR.

In particular, the invention relates to pharmaceutical compositions comprising a plurality of drug-resin particles, wherein the drug in said drug-resin particles comprises at least one ADHD effective agent. For example, in one embodiment, the pharmaceutical composition comprises (a) at least one pharmaceutically active ADHD effective agent drug-resin complex providing for immediate release; and (b) at least one pharmaceutically active ADHD effective agent drug-resin complex covered with a delayed release coating, wherein said component (a) provides for an immediate release of ADHD effective agent from the drug resin complex to provide a first blood level of ADHD effective agent and component (b) provides a delayed release of ADHD effective agent from the drug-resin complex that increases the blood level of ADHD effective agent to a second level.

In one embodiment, the ADHD effective agent is at least one amphetamine such as a mixture of amphetamine and dextroamphetamine (e.g., a mixture of 75% dextroamphetamine and 25% levoamphetamine). In one embodiment, the compositions are substantially free of dextroamphetamine saccharate and/or amphetamine asparate. Alternatively, where the compositions consist essentially of amphetamine salts, anions of those salts are polymeric. In another alternative, the compositions or the drug-resin particles are substantially free of soluble anions. In another embodiment, the ADHD effective agent is methylphenidate.

In preferred embodiments, the compositions comprise a first plurality of drug-resin particles that are not coated with a delayed release coating, and a second plurality of drug-resin particles that are coated with a delayed release coating. The delayed release may comprise a triggered-release coating (e.g., where a pH change triggers the triggered-release coating such as EUDRAGIT® L100). The particles covered by a triggered-release coating may further comprise an extended release coating such as a diffusion barrier coating (e.g., a water insoluble, water permeable membrane such as ethylcellulose).

The compositions may comprise various amounts of the first and second plurality of drug-resin particles. For example, in one embodiment, the compositions comprise 20%-50% of the first plurality of drug-resin particles and 50-80% of the second plurality of drug-resin particles. In particular, the compositions may comprise 40%-50%, or about 45%, of the first plurality of drug-resin particles and 50%-60% or about 55% of the second plurality of drug-resin particles. In other particular embodiments, the compositions may comprise 20%-30%, or about 25%, of the first plurality of drug-resin particles and 70%-80% or about 75% of the second plurality of drug-resin particles.

In some embodiments, the resin particles are strong acidic cation exchange resins such as polistirex, polacrilex, or polacrilin. In other embodiments, the resin particles are AMBERLITE® IRP64, IRP69, or IRP88 resins, or DUOLITE™ AP143 resins. The compositions may be liquid suspensions, chewable compositions, or an orally disintegrating tablet compositions.

The invention provides for compositions having unique in vitro dissolution profiles. In particular, the rate of appearance of the drug in a dissolution medium increases after a period of decrease in the rate of appearance of the drug in the dissolution medium. The period of decrease in the rate of appearance of the drug may occur within 0.5, 1, 1.5, 2, or 2.25 hours after the composition is introduced into the dissolution medium. In some embodiments, 30-60% of the drug may be released before the rate of appearance of the drug in a dissolution medium increases. Typically, release of 80% or more of the drug is achieved only after the rate of appearance of the drug in the dissolution medium has decreased and then increased. In particular, 80% or more of the drug is released during the dissolution assay within the first half (i.e., within 12 hours) of the dosing interval (i.e., 24 hour dosing interval).

In other embodiments, 40-45% of the drug is released within the first 45 minutes after the drug-resin particles are introduced into a dissolution assay, followed by a period of substantially no drug release from 45 minutes to 2 hours, and concluding with period of from 2 to 8 hours during which substantially all of the remaining drug is released. In another embodiment, 40-45% of the drug is released within the first 45 minutes after the drug-resin particles are introduced into a dissolution assay, 45-50% of the drug is released within 2 hours, and 50-100% of the drug is released by 8 hours. In another embodiment, 30-33% of the drug is released the first 30 minutes after the drug-resin particles are introduced into a dissolution assay, 34-42% of the drug is released within 2 hours, 40-80% of the drug is released within 4 hours and 80-100% of the drug is released within 24 hours. In any of these embodiments, the conditions of the dissolution assay are an initial dissolution medium of 0.1 N HCL, and after 2 hours, the medium is adjusted to a pH of ~6.8; and dissolution testing is performed using a USP Apparatus 2.

The invention also provides for compositions having unique in vivo serum profiles. In some embodiments, the composition has an in vivo serum profile with a first and second peak (e.g., where the second peak is the $C_{max}$). For example, the composition may have an in vivo serum profile with a first peak between 1 and 3 hours after ingestion of the composition, and with a second peak between 4 and 7 hours after ingestion of the composition. In a particular mode, the composition may have an in vivo serum profile with a first peak between 1 and 2.5 hours after ingestion of the composition, and with a second peak between 4 and 6 hours after ingestion of the composition. Alternatively, the composition may have an in vivo serum profile that reaches a therapeutically effective level fairly rapidly (1-3 hours) and them continues to increase more slowly up to a maximum serum level between 4 hours and 7 hours after ingestion.

In one aspect, the compositions have in vivo serum profiles bioequivalent to the profiles of compositions described in the Examples and shown in the Figures. In particular aspect, the in vivo serum profile of the composition is bioequivalent to the in vivo serum profile of ADDERALL XR (e.g., under fasted conditions). In other embodiments, the compositions have one or more partial AUCs (e.g., $AUC_{0-4}$, $AUC_{0-5}$, $AUC_{4-12}$, $AUC_{5-12}$, $AUC_5$, $(AUC_{5\text{-}last})$[1], $AUC_{0-24}$, and/or $AUC_{0-\infty}$) which meet the bioequivalence conditions of the compositions described in the Examples (e.g., ADDERALL XR) and shown in the Figures. In another embodiment, the composition, in the presence of ethanol, provides that the recipient of the composition is exposed to a reduced amount of amphetamines compared to ADDERALL XR.

[1] $(AUC_{5\text{-}last})$=$AUC_{5\text{-}t}$=the area under the plasma concentrate time curve for the time between 5 hours after ingestion to the last data point collected.

The invention also provides for methods of treating various conditions such as Attention-Deficit Disorder or ADHD, fatigue, obesity or imparting alertness, by administering an effective amount of the compositions described herein. In one embodiment, the amount of drug delivered to the subject is between about 2 mg/24 hours to about 60 mg/24 hours. In another embodiment, the amount of drug delivered to the subject is about 5 mg/24 hours to about 30 mg/24 hours. In particular embodiments, the effective amount is 0.5 mg/kg/day to 1.5 mg/kg/day, 0.25 mg/kg/day to 0.5 mg/kg/day, or 0.28/kg/day to 0.4 mg/kg/day. The composition may be administered once-a-day as a single or multiple unit dose. This invention is preferred for a subject suffering from dysphagia.

The invention also relates to methods of reducing the effects of an elevated exposure of a subject to ADHD effective agents (e.g., amphetamines). For example, when the compositions are administered substantially contemporaneously with ethanol, such that the subject is exposed to a reduced amount of amphetamines compared to administering ADDERALL XR to a subject substantially contemporaneously with ethanol.

The invention also provides for various methods of making the compositions. In one embodiment, the method involves (a) loading a plurality of resin particles with at least one ADHD effective agent (e.g., at least one amphetamine, methylphenidate) to form drug-resin particles; (b) coating a subset of the drug-resin particles with a triggered-release coating to form coated drug-resin particles; and (c) combining uncoated drug-resin particles with the subset of coated drug-resin particles in a pharmaceutical composition. In another embodiment, the method involves (a) loading a plurality of resin particles with an ADHD effective agent (e.g., methylphenidate) to form drug-resin particles; (b) coating drug-resin particles with an extended release coating (e.g., ethyl cellulose) to form extended release coated drug-resin particles; (c) further coating the extended release coated drug-resin particles with a delayed release coating (e.g., triggered-release coating) to form extended release/delayed release coated drug-resin particles; and (d) combining loaded, but uncoated drug-resin particles with the extended release/delayed release coated drug-resin particles in a pharmaceutical composition.

In another embodiment, the composition, wherein, for in vivo pharmacokinetic parameters of the composition, one or more in vivo pharmacokinetic parameters selected from the group consisting of $C_{max}$, $AUC_{0-5}$, $AUC_{5-12}$, $AUC_{5-24}$, $AUC_{5-t}$ $(AUC_{5\text{-}last})$, $AUC_{0-12}$, $AUC_{0-24}$, $AUC_{0-t}$, and $AUC_{0-\infty}$ have a 90% confidence interval with upper and lower bounds within a range from 90%-115% of the value of the same parameter(s) for a bioequivalent reference composition (e.g., ADDERALL XR).

BRIEF DESCRIPTION OF THE DRAWINGS

FIG. 10A shows the results of d-amphetamine. FIG. 10B shows the results of l-amphetamine.

DETAILED DESCRIPTION OF THE INVENTION

Figure 1:
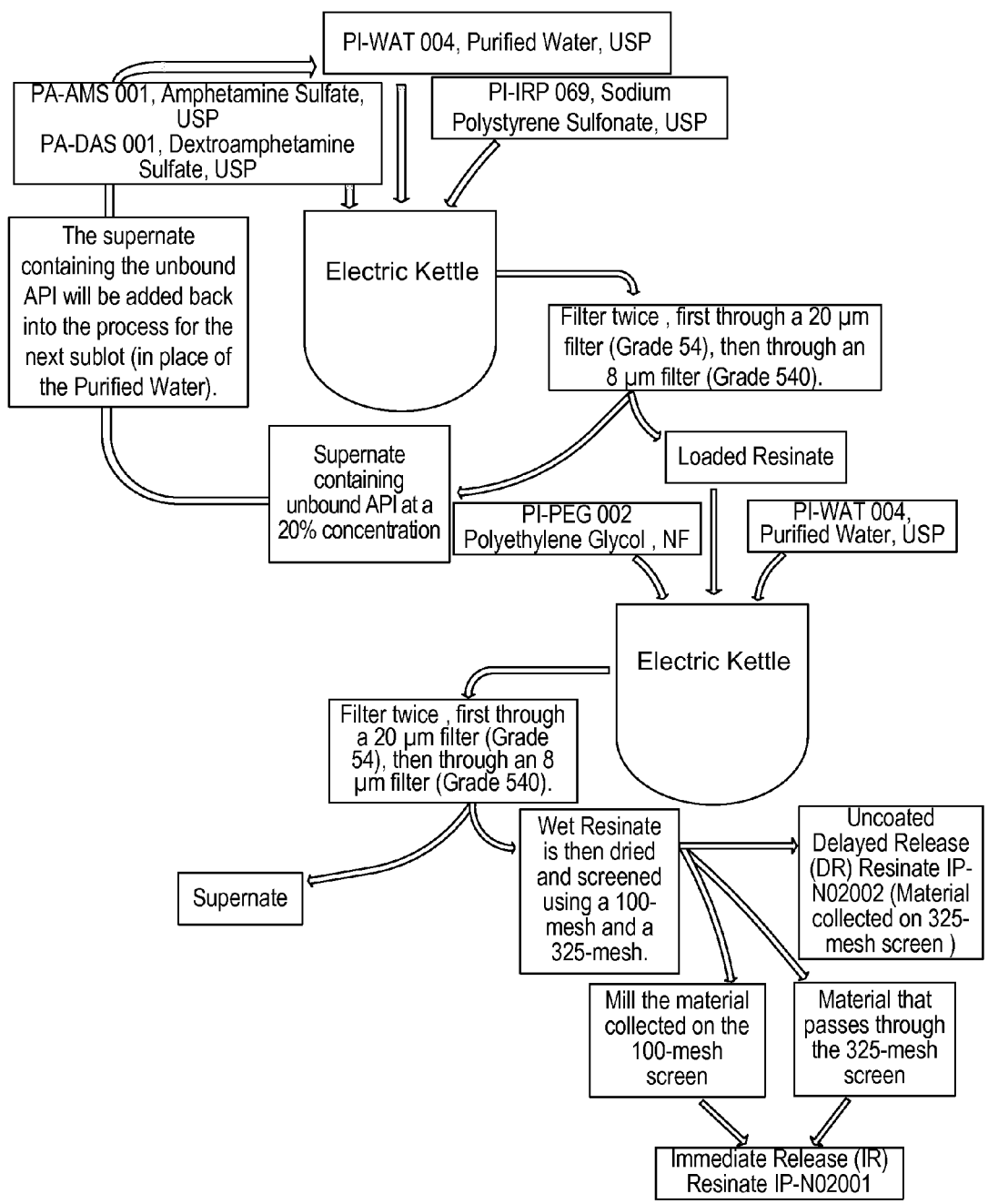
FIG. 1 depicts an exemplary process for loading amphetamines onto resin particles.

The invention provides for various dosage forms comprising drug-resin particles that provide an effective treatment over a prolonged period of time. The invention provides pharmaceutical compositions such as liquid drug suspensions, chewable compositions, or orally disintegrating compositions comprising at least one plurality of drug-resin particles comprising a delayed-release coating. The invention also provides for methods of making pharmaceutical compositions and methods of treatment using these pharmaceutical compositions.

For example, the invention provides for such pharmaceutical compositions in which (i) the rate of appearance of the drug (e.g., at least one amphetamine) in a dissolution medium is increasing during a time period from a first time point through to a second time point, wherein the first time point is at least one hour after the composition is introduced into the dissolution medium; and/or (ii) the composition achieves an ascending plasma concentration of the drug (e.g., at least one amphetamine) after a therapeutically effective level is reached (e.g., one, two, three hours after ingestion of the composition).

The inventors have also observed that, when monitoring the release of the compositions of the invention and a reference listed ADHD effective agent (e.g., amphetamine, methylphenidate) in vivo, contemporaneous consumption of alcohol and drug affected both the rate and amount of ADHD effective agent appearing in the subject's circulation. Consequently, alcohol consumption by a patient being treated for ADHD can substantially increase the patient's level of exposure to ADHD effective agent (e.g., amphetamine, methylphenidate). The compositions of this invention help control the exposure, by reducing dose dumping.

Definitions

As used herein, a "drug-resin particle" is a drug-containing ion-exchange resin particle in which there is an ionic bond between the drug and the ion-exchange resin particle.

As used herein, an "ADHD effective agent" is any agent effective to treat ADHD or ADD in any patient population (e.g., children, adolescents, adults), wherein the agent includes stimulants such as amphetamine, lisdexamphetamine, methylphenidate, and their optical isomers; non-stimulants such as atomoxetine, guanfacine, and clonidine; antidepressants such as bupropion; anti-hypertussives such as gaunfacine and clonidine, derivatives thereof, or any combination that comprises at least one of these agents. As discussed herein, ADHD effective agents may also be used in the effective treatment of other conditions such as fatigue, obesity and for imparting alertness.

As used herein, "controlled release" means the time course of drug appearance in medium surrounding the composition is modified compared to an immediate release composition. Controlled release encompasses "delayed release" and "extended release" formulations.

As used herein, "delayed release" means that appearance of drug in the medium surrounding the composition occurs after a time lapse. An example of a delayed release coating is a triggered-release coating.

As used herein, a "triggered-release coating" is a coating that degrades as a result of a triggering event, where the triggering event is a change in the physiological environment of surrounding the triggered-release coating. Triggering events include, but are not limited to, a pH change which occurs upon transit from one stage to another stage in a subject's GI tract, an enzyme secreted in a particular region in a subject's GI tract, or enzymatic presence in digestion.

As used herein, "extended release" means that the rate of release is slower than the rate for an immediate release or delayed release composition from the initial point of release.

As used herein, "immediate release" means the initial period during which drug is released from the composition that does not involve delayed or extended release but may include taste-masking.

As used herein, a "subject" means any animal, but is preferably a mammal, such as, for example, a human.

As used herein, "dose dumping" means the premature and/or accelerated release of a drug. Dose dumping could produce adverse effects or toxicity due to exposure of the patient to higher levels of the drug.

As used herein, "substantially free of dextroamphetamine saccharate and/or amphetamine asparate" means little to no dextroamphetamine saccharate and/or amphetamine asparate is present. Thus, while trace amounts of dextroamphetamine saccharate and/or amphetamine asparate may be included, therapeutically effective levels of dextroamphetamine saccharate and/or amphetamine asparate are excluded.

As used herein, "substantially free of soluble anions" means little to no soluble anions may be included. Thus, while trace amounts of soluble anions may be included, these trace amounts will affect the release of the drug by no more than 5%, preferably no more than 2%. Particularly, the trace amounts will affect the release of the drug by no more than 5%, preferably no more than 2%, during the first half hour after ingestion of the drug or after introduction of the drug to a dissolution assay.

As used herein, "substantially contemporaneously with ethanol" means ingesting (or introducing) a substance containing ethanol (e.g., beer, wine, hard liquor) within 5, 10, 15, 30, 45, 60, 75, 90, or 120 minutes before or after ingesting (or introducing) a composition of the invention.

As used herein, "substantially all," in the context of drug release, means 90% or more.

As used herein, "substantially similar" parameters have values within −20%/+25% of each other.

Bioavailability

Measures of bioavailability well known in the art include the area under the plasma concentration-time curve (AUC), the concentration maximum ($C_{max}$), and the time to $C_{max}$ ($T_{max}$).

AUC is a measurement of the area under the plasma concentration-time curve, and is representative of the amount of drug absorbed following administration of a single dose of a drug (see Remington: The Science and Practice of Pharmacy, (Alfonso R. Gennaro ed. 2000), page 999).

$C_{max}$ is the maximum plasma concentration achieved after oral drug administration (see Remington, page 999). An oral drug administration results in at least one $C_{max}$, but may result in more than one "peak plasma concentration" or "plasma concentration peak" (for example, following the administration of a pulsed dose formulation).

$T_{max}$ is the amount of time necessary to achieve the $C_{max}$ after oral drug administration, and is related to the rate of absorption of a drug (see Remington, page 999).

Bioequivalence is the absence of a significantly different rate and extent of absorption in the availability of the active ingredient when administered at the same dose under similar conditions. Bioequivalence can be measured by pharmacokinetic parameters such as, for example, AUC and $C_{max}$. According to the FDA, two products are bioequivalent if the 90% confidence intervals of the relative mean AUC, $C_{max}$, and $T_{max}$ of the test formulation are within 80% to 125% (−20%/+25%) of the reference formulation drug when administered in the fasting state. In a particular embodiment, bioequivalence may be established by comparing a test drug to a reference drug by comparing partial AUCs (e.g., over statistically or clinically relevant time intervals). This bioequivalence measure based partial AUCs may be used alone or in combination with the bioequivalence measure discussed above.

As used herein, a dissolution profile is "statistically similar" to another profile if the f2 similarity factor calculated for the two profiles is greater than or equal to 50. (See Moore and Flanner, Pharm. Tech. 20: 64-74, 1996).

Drug-containing Resin Particles

The invention provides for various dosage forms comprising drug-containing ion-exchange resin particles. These particles generally comprise at least one ADHD effective agent (e.g., at least one amphetamine, methylphenidate) bound to particles of an ion-exchange resin to provide a drug-resin complex. This complex may be coated with (i) a delayed release coating (e.g., triggered-release coating); (ii) an extended release coating (e.g., a water-permeable diffusion barrier coating that is insoluble in gastrointestinal fluids (and water) thereby providing a controllable extended release of drug under conditions encountered in the gastrointestinal tract); or (iii) both (i) and (ii). The drug-resins may also include a slow-dissolve polymer coating. Alternatively, the drug-resin particles are uncoated, i.e., omit a delayed release coating (e.g., triggered-release coating) and/or other coating (e.g., water-permeable diffusion barrier coating).

Resins

Ion-exchange resins suitable for use in the preparations and methods described herein are water-insoluble and comprise an indigestible organic and/or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion-exchangers suitable for use in ion-exchange chromatography and for such applications as deionization of water are suitable for use in the controlled release of drug preparations. Suitable ion exchange resins are also sold under the trade names AMBERLITE and Dowex. Such ion-exchangers are described by H. F. Walton in "Principles of Ion Exchange" (pp. 312-343) and "Techniques and Applications of Ion-Exchange Chromatography" (pp. 344-361) in Chromatography. (E. Heftmann, editor), Van Nostrand Reinhold Company, New York (1975), incorporated herein by reference. Exemplary ion-exchange resins that can be used in the present invention have exchange capacities below about 6 milliequivalents (meq)/gram and preferably below about 5.5 meq/gram.

Typically, the size of the ion-exchange particles is from about 30 microns to about 500 microns, preferably the particle size is within the range of about 40 micron to about 150 micron for liquid dosage forms, although particles up to about 1,000 micron can be used for solid dosage forms, e.g., tablets and capsules. Particle sizes substantially below the lower limit are difficult to handle in all steps of the processing. Commercially-available ion-exchange resins having an irregular shape and larger diameters up to about 200 micron are gritty in liquid dosage forms. Moreover, it is believed that the increased distance that a displacing ion must travel in its diffusion into these large particles, and the increased distance the displaced drug must travel in its diffusion out of these large particles, cause a measurable but not readily controlled prolongation of release, even when the drug-resin complexes are uncoated. Release of drug from uncoated drug-resin complexes with particle sizes in the approximate range of 40 micron to 150 micron is relatively rapid in the appropriate environment. Satisfactory control of the release from such complexes is achieved almost exclusively by applying a diffusion barrier coating.

Both regularly and irregularly shaped particles may be used as resins. Regularly shaped particles are those particles that substantially conform to geometric shapes, such as spherical, elliptical, cylindrical and the like, which are exemplified by Dow XYS-40010.00 and Dow XYS-40013.00 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by AMBERLITE IRP-69 (Rohm and Haas). Two of the preferred resins of this invention are AMBERLITE IRP-69 and Dow XYS-40010.00. Both are sulfonated polymers composed of polystyrene cross-linked with 8% of divinylbenzene, with an ion-exchange capacity of about 4.5 to 5.5 meq/g of dry resin ($Na^+$-form). Their essential difference is in physical form. AMBERLITE IRP-69 consists of irregularly-shaped particles with a size range of 47 micron to 149 micron produced by milling the parent large-sized spheres of AMBERLITE® IRP-120. The Dow XYS-40010.00 product consists of spherical particles with a size range of 45 micron to 150 micron. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 meq/g of dry resin.

The following U.S. patents and Publications describe resins suitable for use in the preparations and methods described herein: U.S. Pat. Nos. 4,221,778; 4,996,047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

Drugs

Drugs that are suitable for the invention may be acidic, basic or amphoteric. Basic drugs that can be used in the present invention include amphetamine and methylphenidate. Drugs which may be used in the invention include ADHD effective agents such as amphetamine, dextroamphetamine, levoamphetamine, lisdexamphetamine, methylphenidate, dexmethylphenidate, atomoxetine, guanfacine, clonidine, and bupropion. In preferred embodiments, the drug is a stimulant such as amphetamine and methylphenidate.

Drug-resin Complexes

Binding of drug to resin can be accomplished using methods known in the art. Indeed, one of ordinary skill in the art can easily determine the appropriate method depending upon the drug. Typically four general reactions are used for a basic drug, these are: (a) resin ($Na^+$-form) plus drug (salt form); (b) resin ($Na^+$-form) plus drug (as free base); (c) resin ($H^+$-form) plus drug (salt form); and (d) resin ($H^+$-form) plus drug (as free base). All of these reactions except (d) have cationic by-products and these by-products, by competing with the cationic drug for binding sites on the resin, reduce the amount of drug bound at equilibrium. For basic drugs, stoichiometric binding of drug to resin is accomplished only through reaction (d).

Typically, the ion-exchange resin, in the form indicated by the chosen reaction, is placed in an aqueous solution of the chosen form of drug and agitated. The drug-resin complex thus formed is collected and washed with deionized or purified water to ensure removal of any unbound drug. The complexes are then dried.

Uncoated drug-resin complexes rapidly release the drug in the subject, such as, for example, in the gastrointestinal tract. To delay the release of drug from the drug-resin complex, the complex may be coated as described below.

The amount of drug that can be loaded onto a resin will typically range from about 1% to about 80%, preferably about 15% to about 60%, by weight of the loaded drug-resin particles. A skilled artisan with little or no experimentation can readily determine the optimum loading for any drug resin complex. In a preferred embodiment, loadings of about 30% to about 60% by weight of the drug-resin particles can be employed.

Those of skill in the art will appreciate that certain drugs will have an affinity for particular types of resins. The inventors have determined that the loading levels of amphetamine are suitable on strongly acidic cation exchange resins such as AMBERLITE IRP-64 and AMBERLITE IRP-69 resins. Resins useful in the invention with modification of the API are strong base anion exchange resins (e.g., DUOLITE™ AP143) and weak acid cation exchange resins (e.g., AMBERLITE IRP-88).

Amphetamine resin complexes can be formed using any amphetamine salt, since the salt counter-ion is replaced by the ion exchange resin, and release of the drug is controlled by coating and ionic bonding, rather than differential solubility of the salts. In a preferred mode, resin particles are loaded using a single salt of racemic amphetamine and a single salt of dextroamphetamine.

The following U.S. patents and Publications describe preparations and methods suitable for drug-resin complexes described herein: U.S. Pat. Nos. 4,221,778; 4,996,047; and 5,980,882; U.S. Publication Nos. 2003/0099711; 2006/0193877; 2007/0059270; 2007/01400983; 2007/0148239; and 2009/0011027. The disclosure of each of these patents and publications is incorporated by reference herein in their entireties.

Impregnation

Drug-resin particles can be impregnated with a humectant substantially as described in U.S. Pat. No. 4,221,778. The humectant can be added as an ingredient in the resin drug complexation step or, preferably, the particles can be treated with the humectant after complexing. This treatment helps particles retain their geometry, and enables the effective application of diffusion barrier coatings to such particles. One preferred humectant is polyethylene glycol, a hydrophilic agent. Other effective humectant agents include, for example, propylene glycol, lactose, methylcellulose, hydroxypropylmethylcellulose, sugar alcohols such as sorbitol, mannitol, polyvinylpyrrolidone, carboxypolymethylene, xanthan gum, propylene glycol, alginate and combinations of these agents. The humectant may be added in an amount of up to about 50 parts per 100 parts by weight of the resin or 50 to 150 parts per 100 parts of the resin; such humectant levels have been found to be effective. Preferably, the humectant (solvating agent) is added in an amount of about 75 to about 100 parts per 100 parts of resin.

Coatings

Coating layers can provide immediate release, delayed release, pulsed release, or extended release of drug from the drug-resin particle. Immediate release of the drug from the immediate-release layer can be achieved by any of various methods known in the art. One example is the use of a very thin layer or coating which by virtue of its thinness is quickly penetrated by gastric fluid allowing rapid leaching of the drug. Another example is by incorporating the drug in a mixture that includes a supporting binder or other inert material that dissolves readily in gastric fluid, releasing the drug as the material dissolves. A third is the use of a supporting binder or other inert material that rapidly disintegrates upon contact with gastric fluid, with both the material and the drug quickly dispersing into the fluid as small particles. Examples of materials that rapidly disintegrate and disperse are lactose and microcrystalline cellulose.

The following U.S. patents and Publications describe coating materials suitable for use in the preparations and methods described herein: U.S. Pat. Nos. 4,221,778; 4,996,047; and 5,980,882; U.S. Publication Nos. 2003/0099711; 2006/0193877; 2007/0059270; 2007/01400983; 2007/0148239; US 2007/0264323; and 2009/0011027. The disclosure of each of these patents and publications is incorporated by reference herein in their entireties.

Diffusion Barrier Coating

Loaded particles may be coated with a diffusion barrier comprising a water-permeable, film-forming polymer. Any coating procedure which provides a contiguous coating on each particle of drug-resin complex without significant agglomeration of particles may be used. Coatings may be applied with a fluid-bed coating apparatus having the Wurster configuration. Measurements of particle size distribution can be done before and after coating to show that agglomeration of particles is acceptable.

The polymer may be any of a large number of natural or synthetic film-formers used singly, or in admixture with each other, and optionally in admixture with plasticizers, pigments and other substances to alter the characteristics of the coating. In general, the diffusion barrier coating should be insoluble or slowly soluble in water and permeable to water. Additional examples of coating polymers are described by R. C. Rowe in Materials Used in Pharmaceutical Formulation (A. T. Florence, editor), Blackwell Scientific Publications, Oxford, 1-36 (1984), incorporated by reference herein.

Preferably, the diffusion barrier is ethyl cellulose, for example, an ethyl cellulose having the content of ethoxyl group from 44 to 47.5%, preferably from 45 to 46.5%. In embodiments of the present invention, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it may be necessary to add plasticizer to the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after routine experimentation with the particular coating solution and method of application.

Examples of suitable plasticizers for ethylcellulose include water insoluble plasticizers such a dibutyl sebacate, diethyl phthalate, triethyl citrate, tributyl citrate and triacetin, although it is possible that other water-insoluble plasticizers (such as acetylated monoglycerides, phthalate esters, castor oil, etc.) may be used. A plasticizer such as Durkex 500 vegetable oil may also be incorporated to improve the film forming property. In one alternative, it is desirable to incorporate a water-soluble substance, such as methyl cellulose, to alter the permeability of the coating.

The diffusion barrier coating materials can be applied as an aqueous suspension. One commercially available aqueous dispersion of ethylcellulose is Aquacoat® (FMC Corp., Philadelphia, Pa., U.S.A.). Aquacoat® is typically prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is preferable to intimately mix the Aquacoat® with a suitable plasticizer prior to use.

Another aqueous dispersion of ethylcellulose is commercially available as Surelease® (Colorcon, Inc., West Point, Pa., U.S.A.). This product is typically prepared by incorporating plasticizer into the dispersion during the manufacturing process. A hot melt of a polymer, plasticizer (e.g., dibutyl sebacate), and stabilizer (e.g., oleic acid) may be prepared as a homogeneous mixture, which is then diluted with an alkaline solution to obtain an aqueous dispersion which can be applied directly onto substrates.

Another alternative coating material is a mixture of an insoluble, film-forming polymer and a water soluble pore former or polymer, i.e., refers to a two-component system. One preferred water soluble polymer is methyl cellulose, which may be used in a two-component system with ethylcellulose.

Another alternative coating material is a mixture of two insoluble, film-forming polymers; for example polyvinyl acetate phthalate (PVAP) and ethylcellulose. Another alternative coating material is polyvinylpyrrolidone (PVP), polyvinylalcohol, polyvinylacetate and mixtures thereof.

Typically, the water-permeable, film-forming polymer comprises from about 1% to about 60% by weight of the drug-resin complex, and preferably from about 20% to about 50% by weight of the dry resin. In terms of coat thickness, preferably, the diffusion barrier coat thickness is at least 5 microns and more preferably, the diffusion barrier coat thickness is from about 10 microns to about 50 microns. Optimum coat weight and coat thickness may be determined for each drug-resin complex and generally depend on the drug release characteristics of the resin for a particular drug. For example, to achieve drug release times within about 1 hour to about 4 hours, the drug-resin complex may be coated with a light coat weight. A light coat weight is a coat weight present in the amount of about 10% to about 20% by weight of the dry resin. To achieve drug release times from about 6 hours to 10 hours, a medium coat weight may be used, i.e. a coat weight present in the amount of 30% to about 35% by weight. To achieve drug release times for about 12 hours, a heavy coat weight may be used, i.e. a coat weight of about 40% to 50% by weight of the dry resin.

Triggered-release Coatings

A water-soluble barrier comprises a pharmaceutically acceptable polymer such as, for example, methylcellulose (dissolves in cold water), hydroxypropylmethylcellulose (HPMC), hydroxyethlycellulose (HEC), acrylic acid ester, cellulose acetate phthalate, HEC phthalate, HPMC phthalate, hydroxypropyl cellulose (HPC), polyethylene glycol, polyvinyl alcohol, xanthan gum, carbomer, carrageenan, zooglan or other cellulosic polymers, or mixtures of polymers. Drugs mixed with one or more of these polymers, or covered by a layer of the polymer, will not be released until the polymer dissolves or degrades.

Triggered-release coatings are degraded as a result of a triggering event. Triggering events may be pH dependent or pH independent. A pH dependent coating is activated to release drug within a known pH range, which typically is matched to the local pH of the environment where delayed release is desired. Exemplary pH dependent coatings include cellulose acetate phthalate, cellulose acetate trimellitate, hydroxypropyl methylcellulose phthalate, polyvinyl acetate phthalate (PVAP), carboxymethylethylcellulose, co-polymerized methacrylic acid/acrylic acid ethyl esters, co-polymerized methacrylic acid/methacrylic acid methyl esters such as, for instance, materials known under the trade name EUDRAGIT L12.5, L100, or EUDRAGIT S12.5, S100 or similar compounds. Aqueous colloidal polymer dispersions or re-dispersions can be also applied, e.g., EUDRAGIT L 30D-55, EUDRAGIT L100-55, EUDRAGIT S100, EUDRAGIT preparation 4110D (Rohm Pharma); AQUATERIC, AQUACOAT CPD 30 (FMC); KOLLICOAT MAE 30D and. 30DP (BASF); or EASTACRYL 30D (Eastman Chemical). Aqueous colloidal polymer dispersions or re-dispersions can be also applied, e.g. EUDRAGIT® L 30D-55, EUDRAGIT L100-55, EUDRAGIT S100, EUDRAGIT preparation 4110D (Rohm Pharma); AQUATERIC®, AQUACOAT CPD 30 (FMC); KOLLICOAT MAE® 30D and 30DP (BASF); EASTACRYL® 30D (Eastman Chemical).

A pH independent coating includes materials susceptible to enzymatic activation. Exemplary triggered-release coatings include cross-linked gelatin, polylactic acid, cellophane, plastarch material, polycaprolactone, polyglycolide, poly-3-hydroxybutyrate, zein, materials susceptible to enzymatic activation by azo-reductases in intestinal bacteria, and materials susceptible to degradation in the colon.

The invention provides for combinations of triggered-release coatings and diffusion barrier coatings. For example, the invention provides for drug-resin particles that include a diffusion barrier coating such as ethylcellulose which is overcoated with a triggered-release coating (or vice versa, i.e., the triggered-release coating is overcoated with a diffusion barrier coating). This multicoated particle provides for a delayed release (via the triggered-release coating) followed by an immediate or extended release (via the diffusion barrier coating).

Dosage Forms

The invention provides for pharmaceutical compositions comprising various pluralities of drug-resin particles in which the pharmaceutical composition is, for example, a liquid, a chewable composition, or an orally disintegrating solid. Alternatively, pharmaceutical compositions according to this invention may be prepared in capsules or by standard tableting methods. For example, the invention provides for such pharmaceutical compositions in which (i) the rate of appearance of the drug (e.g., at least one amphetamine) in a dissolution medium is increasing during a time period from a first time point through to a second time point, wherein the first time point is at least one hour after the composition is introduced into the dissolution medium; and/or (ii) the composition achieves an ascending plasma concentration of the drug (e.g., at least one amphetamine) after a therapeutic effective level is reached (e.g., one, two, three hours after ingestion of the composition).

In any of the dosage forms described herein, the drug may be at least one of an amphetamine or dextroamphetamine, or methylphenidate. In some preferred modes, both amphetamine or dextroamphetamine are present.

Liquid Drug Suspensions

The invention provides for liquid oral dosage forms. These dosage forms have distinct advantages over prior art solid dosage forms including dosage flexibility and ease of swallowing. Liquid dosage forms are especially preferred for pediatric use.

Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. Liquid forms, such as syrups and suspensions, preferably contain from about 1% to about 50%, and more preferably from about 1% to about 25%, and most preferably from about 3% to about 10%, of the drug-resin complex. Other optional ingredients well known to the pharmacist's art may also be included in amounts generally known for these ingredients, for example, natural or artificial sweeteners, flavoring agents, colorants and the like to provide a palatable and pleasant looking final product; acidulants, for example, citric acid, ascorbic acid, or malic acid and the like to adjust pH; antioxidants, for example, butylated hydroxy anisole or butylated hydroxy toluene; and preservatives, for example, methyl or propyl paraben or sodium benzoate, to prolong and enhance shelf life.

In preparing the liquid oral dosage forms, the coated drug-resin complexes are incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. Preferably, the carrier is a suspension of the pharmaceutical composition in an aqueous vehicle containing a suitable suspending agent. Suitable suspending agents include Avicel RC-591 (a microcrystalline cellulose/sodium carboxymethyl cellulose mixture available from FMC), guar gum and the like. Such suspending agents are well known to those skilled in the art. While the amount of water in the compositions of this invention can vary over quite a wide range depending upon the total weight and volume of the drug-resin complex and other optional non-active ingredients, the total water content, based on the weight of the final composition, will generally range from about 20 to about 75%, and, preferably, from about 20 to about 40%, by weight/volume.

Although water itself may make up the entire carrier, typical liquid formulations may contain a co-solvent, for example, propylene glycol, glycerin, sorbitol solution and the like, to assist solubilization and incorporation of water-insoluble ingredients, such as flavoring oils and the like, into the composition. In general, therefore, the compositions of this embodiment preferably contain from about 5 to about 25 volume/volume percent and, most preferably, from about 10 to about 20 volume/volume percent, of the co-solvent.

Orally Disintegrating and Chewable Dosage Forms

The invention also provides for compositions and methods of making orally disintegrating or chewable, controlled-release formulations. In particular, the invention provides for orally disintegrating and chewable dosage forms comprising the various pluralities of drug-resin particles described herein Like liquid dosage forms, orally disintegrating and chewable dosage forms have distinct advantages over prior art solid dosage forms including ease of ingestion. Methods of preparing orally disintegrating and chewable dosage forms with drug-resins are known in the art. See U.S. Publication No. 2007/0092553, which is hereby incorporated by reference in its entirety.

Drug Release Profiles

The invention provides for compositions having various drug (e.g., ADHD effective agent) release profiles. In particular, the compositions may be administered in the morning and have therapeutically effective activity throughout the course of the day. For example, in one embodiment, the composition is administered to a child during breakfast (i.e., before school starts) and, by the time school starts, the ADHD effective agent (e.g., amphetamine, methylphenidate) will begin having a therapeutic effect on the child. The composition will continue to be therapeutically effective throughout the day including the mid-afternoon, when children tend to be fatigued. As such, the compositions described herein have an escalating in vivo serum profile.

In some embodiments, the invention provides for compositions in which the rate of appearance of the ADHD effective agent (e.g., at least one amphetamine) in a dissolution medium increases after a period of decrease in the rate of appearance of the drug in the dissolution medium. The compositions typically contain an immediate release and delayed release portion. The immediate release portion, in an in vitro dissolution assay, contributes to an initial release of ADHD effective agent (e.g., 30-60%) within an initial time period (e.g., 0.5, 1, 1.5, 2, or 2.25 hours from when the composition is introduced into the dissolution medium). After the initial increase amount of ADHD effective agent in the dissolution, due to the immediate release portion, the release rate of ADHD effective agent will decrease or level off. After this decrease or leveling off, typically the delayed release portion will release and the amount of ADHD effective agent released increases until, e.g., 80% or more of the ADHD effective agent is released. It will be appreciated that the first and second time points will vary depending on the ADHD effective agent, coatings used, and ratio of immediate and delayed release drug-resin particles.

In a particular embodiment, 40-45% of the drug (e.g., ADHD effective agent such as at least one amphetamine) is released within the first 45 minutes after the drug-resin particles are introduced into a dissolution assay, followed by a period of substantially no drug release from 45 minutes to 2 hours, and concluding with period of from 2 to 8 hours in which substantially all of the remaining ADHD effective agent is released from 2 to 8 hours. In another embodiment, 40-45% of the drug (e.g., ADHD effective agent such as at least one amphetamine) is released within the first 45 minutes after the drug-resin particles are introduced into a dissolution assay, 45-50% of the drug is released within 45 minutes to 2 hours, and 50-100% of the drug is released within 2 to 8 hours. In another embodiment, the delayed release coating releases substantially all of the one or more pharmaceutically active ADHD effective agents (e.g., amphetamines) coated with the delayed release coating within about 60 minutes after initiation of the delayed release. In yet another embodiment, 30-33% of the drug (e.g., ADHD effective agent such as methylphenidate) is released the first 30 minutes after the drug-resin particles are introduced into a dissolution assay, 34-42% of the drug is released within 30 minutes to 2 hours, 40-80% of the drug is released within 2 to 4 hours and 80-100% of the drug is released within 4 to 24 hours. For any of these embodiments, the conditions of the dissolution assay may be an initial dissolution medium of 0.1 NHCL, and after 2 hours, the medium is adjusted to a pH which triggers the triggered release coating, e.g., pH of~6.8; and dissolution testing is performed using a USP Apparatus 2. In other embodiments, the pH is adjusted to e.g., pH 6.8, 7, etc.

The invention also provides for compositions in which the composition achieves an ascending plasma concentration of the drug (e.g., at least one amphetamine during a time period) after a therapeutically effective level is reached. Typically, a therapeutically effective level is reached within one, two, three, four, or five hours after ingestion of the composition. Sometime after the therapeutically effective level is reached, the plasma concentration of drug increases due to additional release of drug from the drug-resin complex in the composition to a peak drug concentration level. In some individuals, clearance of drug will result in a decrease in plasma level between these two releases, resulting in two successive peak drug levels. In others, the timing of the two releases is close enough that no decrease is observed. As a result, the in vivo plasma concentration profile is preferably bimodal with two peaks. For example, the first peak may be achieved, between 1 to 3, 1 to 2.5, or 1 to 2 hours after ingestion of the composition. The second peak may be achieved 4 to 7, 4 to 6, or 4 to 5 hours after ingestion of the composition. The first or second peak may be the $C_{max}$. Alternatively, the composition may have an in vivo serum profile that reaches a therapeutically effective level fairly rapidly (1-3 hours) and them continues to increase more slowly up to a maximum serum level between 4 hours and 7 hours after ingestion. It will be appreciated that the therapeutic and peak drug concentration level will vary depending on the subject, drug, coatings used, and ratio of immediate and delayed release drug-resin particles.

The compositions of the invention may include at least one plurality of drug-resin particles coated with a triggered-release coating. In a particular embodiment, the invention provides for a first plurality of uncoated drug-resin particles and a second plurality of drug-resin particles being coated with a triggered-release coating. In another embodiment, the invention provides for a first plurality of uncoated drug-resin particles, a second plurality of drug-resin particles being coated with a triggered-release coating, and a third plurality of drug-resin particles being coated with a diffusion barrier coating. In another embodiment, the composition is a liquid dosage form and includes at least one plurality of drug-resin particles being coated with a triggered-release coating accompanied by unbound drug in solution.

Any of the diffusion barrier coatings or triggered-release coatings described herein may be used in any of the dosage forms described herein. For example, the some embodiments, the triggered-release coating is EUDRAGIT L100 or EUDRAGIT L100-55. In some embodiments, the triggered-release coating may have an overcoat (e.g., HPMC).

In other embodiments, the drug-resin particles may comprise both a triggered-release and a diffusion barrier coating. For example, the triggered-release coating may cover (i.e., overcoat) the diffusion barrier coating. In one embodiment, the diffusion barrier coating is ethylcellulose and the triggered-release coating is polyvinyl acetate phthalate (PVAP).

The invention provides pharmaceutical compositions comprising various mixtures of immediate release drug-resin particles (e.g., uncoated drug-resin particles) and delayed release drug-resin particles (e.g., triggered-release coated drug-resin particles). In one embodiment, the pharmaceutical composition comprises 20%-50% of immediate release drug-resin particles and 50-80% of delayed release drug-resin particles. In a particular embodiment, the composition comprises 40%-50% of immediate release drug-resin particles and 50%-60% of delayed release drug-resin particles. In a specific embodiment, the pharmaceutical composition comprises 45% of immediate release drug-resin particles and 55% of delayed release drug-resin particles. In another embodiment, the composition comprises 20%-30% of immediate release drug-resin particles and 70%-80% of delayed release drug-resin particles. In a specific embodiment, the pharmaceutical composition comprises 25% of immediate release drug-resin particles and 75% of delayed release drug-resin particles. As shown in the Examples, the percentage of uncoated and coated particles, as well as the types and percentages of coatings, effects the release profiles of the drug (e.g., at least one amphetamine).

The Examples provide in vitro dissolution and in vivo serum profiles for exemplary compositions of the inventions. These compositions (and their profiles) are encompassed within the invention. It will be understood that complete and partial profiles (e.g., partial AUCs) of the compositions set forth and described in the Examples are encompassed within the invention.

In one embodiment, the invention provides for administering an effective amount of a ADHD effective agent (e.g., at least one amphetamine such as a mixture of levo-amphetamine and dextroamphetamine). The effective dosage may range from 3.13 mg of amphetamine calculated as free base (equivalent to 5 mg of mixed amphetamine salts found in ADDERALL XR) to 18.8 mg of amphetamine calculated as free base (equivalent to 30 mg of mixed amphetamine salts found in ADDERALL XR). The amphetamine provided is preferably a mixture of 75% dextroamphetamine and 25% levoamphetamine. A delivery of about 2 mg/24 hours to about 60 mg/24 hours of the compositions of the invention, and more preferably from about 5 mg/24 hours to about 30 mg/24 hours, is typically needed to achieve a therapeutically effective dose in a patient (based on mixed amphetamine salts in ADDERALL XR). In particular embodiments, children 6-12 years old may take 10-30 mg/day (e.g., 0.5 mg/kg/day to 1.5 mg/kg/day), adolescents 13-17 years old may take 10-20 mg/day (0.25 mg/kg/day to 0.5 mg/kg/day), and adults may take 20 mg/day (0.28/kg/day to 0.4 mg/kg/day) (based on a mixed amphetamine salt in ADDERALL XR).

In another embodiment, the invention provides for administering an effective amount of methylphenidate. In one embodiment, the effective dosage ranges from 8.7 mg of methylphenidate base (equivalent to 10 mg of methylphenidate HCl) to 52.2 mg of methylphenidate base (equivalent to 60 mg of methylphenidate HCl). In another embodiment, the effective dosage is 26.1 mg of methylphenidate base (equivalent to 30 mg of methylphenidate HCl). A delivery of about 10 mg/24 hours to about 60 mg/24 hours of the compositions of the invention, and more preferably from about 20 mg/24 hours to about 40 mg/24 hours, is typically needed to achieve a therapeutically effective dose in a patient (based on methylphenidate HCl).

The compositions may be administered once-a-day (e.g., in a single unit or multiple unit compositions) in an amount that provides a therapeutic benefit equivalent to multiple doses of immediate release dosages.

The invention also provides for unit doses and packaging comprising unit dosages. For example, the invention provides for individually packaged liquid drug suspensions (e.g., 5, 10, 15, 30, or 60 ml), or the equivalent amount of drug as a chewable compositions or orally disintegrating dosage forms described herein. Methods of preparing unit dosage forms are known in the art.

It will be understood that the various aspects described herein may be combined. For example, the invention provides for a pharmaceutical composition comprising a first plurality of drug-resin particles being uncoated and a second plurality of drug-resin particles being coated with a triggered-release coating, wherein the drug is an ADHD effective agent (e.g., at least one amphetamine, methylphenidate) and the resin is IRP-64, IRP-69, IRP-88, or AP143.

Methods of Making Dosage Forms

The invention provides for methods of making the pharmaceutical compositions described herein. In one embodiment, the method comprises (a) loading a plurality of resin particles with at least one ADHD effective agent (e.g., at least one amphetamine, methylphenidate) to form drug-resin particles; (b) coating a subset of the loaded drug-resin particles with a delayed release coating (e.g., triggered-release coating) to form coated drug-resin particles; and (c) combining a subset of loaded, uncoated drug-resin particles with coated drug-resin particles in a pharmaceutical composition. In another embodiment, the method comprises (a) loading a plurality of resin particles with at least one ADHD effective agent (e.g., at least one amphetamine, methylphenidate) to form drug-resin particles; (b) coating drug-resin particles with a delayed release coating (e.g., triggered-release coating) to form coated drug-resin particles; and (c) combining said drug-resin particles with said coated drug-resin particles in a pharmaceutical composition.

In another embodiment, the method involves (a) loading a plurality of resin particles with an ADHD effective agent (e.g., methylphenidate) to form drug-resin particles; (b) coating drug-resin particles with an extended release coating (e.g., ethyl cellulose) to form extended release coated drug-resin particles; (c) further coating the extended release coated drug-resin particles with a delayed release coating (e.g., triggered-release coating) to form extended release/delayed release coated drug-resin particles; and (d) combining loaded, but uncoated drug-resin particles with the extended release/delayed release coated drug-resin particles in a pharmaceutical composition. In an alternative embodiment, a delayed release coating is applied to the loaded drug-resin particles to form delayed release coated drug-resin particles, and the extended release coating is then applied to the delayed release coated drug-resin particles.

The compositions made by the methods described herein may comprise various pluralities of drug-resin particles with the profiles described herein. For example, the composition may comprise pluralities of drug-resin particles such that (i) the rate of appearance of the drug (e.g., at least one amphetamine) in a dissolution medium is increasing during a time period from a first time point through to a second time point, wherein the first time point is at least one hour after the composition is introduced into the dissolution medium; and/or (ii) the composition achieves an ascending plasma concentration of the drug (e.g., at least one amphetamine) after a therapeutic effective level is reached (e.g., one, two, three hours after ingestion of the composition).

Methods of loading drugs onto resin particles are generally known in the art. The invention provides for methods of loading ADHD effective agents (e.g., at least one amphetamine, methylphenidate) onto resin particles (e.g., IRP-69, IRP-64, IRP-88, AP143). An exemplary method of loading is depicted in FIG. 1 and described in Example 1. In another embodiment, the composition comprises drug-resin particles comprise a mixture of l- and d-amphetamine (e.g., 25% l-amphetamine and 75% d-amphetamine), wherein each enantiomer is loaded onto a separate resin and the separately loaded resins are combined to form drug-resin particles. Alternatively, l- and d-amphetamine are mixed together in the desired ratio (e.g., 25% l-amphetamine and 75% d-amphetamine) and the mixed amphetamines are then loaded onto resins to form drug-resin particles.

Methods of coating drug-resin particles are also generally known in the art. The invention provides for various coating solutions and combinations of coatings (e.g., triggered-release coating such as EUDRAGIT L100, and a combination of EUDRAGIT 100 with HPMC). Example 2 provides an exemplary coating process and Examples 4-9 provide exemplary compositions with different coatings. Coatings may be applied using methods known in the art, such as with a fluid-bed coating apparatus having the Wurster configuration.

In alternative embodiments, the invention provides for methods of making orally disintegrating and chewable dosage forms comprising the various pluralities described herein. Methods of preparing orally disintegrating and chewable dosage forms with drug-resins are known in the art. See U.S. Publication No. 2007/0092553, which is hereby incorporated by reference in its entirety.

It will be understood that the various aspects described herein may be combined. For example, the invention provides for a pharmaceutical composition comprising a first plurality of drug-resin particles being uncoated and a second plurality of drug-resin particles being coated with a triggered-release coating, wherein the drug is at least one amphetamine or methylphenidate and the resin is IRP-64, IRP-69, IRP-88, AP143.

Methods of Treatment

The invention provides for various methods of treatment using the dosage forms described herein. In a particular embodiment, the invention provides for methods of treating ADD or ADHD, fatigue, obesity, or for imparting alertness, comprising administering an effective amount of any of the compositions described herein (e.g., a composition comprising at least one plurality of drug-resin particles being uncoated and at least one plurality of drug-resin particles coated with a delayed release coating such as a triggered-release coating, where the drug is at least one ADHD effective agent and the composition is, for example, a liquid, a chewable composition, or an orally disintegrating solid). In a preferred method, the individual being treated suffers from dysphagia.

It will be understood that the various aspects described herein may be combined. For example, the invention provides for methods of treating ADD or ADHD comprising administering an effective amount of a pharmaceutical composition comprising a first plurality of drug-resin particles being uncoated and a second plurality of drug-resin particles being coated with a triggered-release coating, wherein the drug is at least one amphetamine or methylphenidate and the resin is IRP-64, IRP-69, IRP-88, AP143.

Methods of Reducing Exposure of Amphetamines

The inventors have observed that, when the compositions described herein are administered to a subject substantially contemporaneously with ethanol, the subject has a reduced exposure level of an ADHD effective agent (e.g., amphetamines) compared to administering a reference listed drug (e.g., ADDERALL XR) to a subject substantially contemporaneously with ethanol. In particular embodiments, the exposure of amphetamines are reduced within 1.0, 1.5, 2.0, 2.5, and/or 3.0 hours after ingestion of the composition and ethanol. As such, the invention relates to methods of reducing exposure of amphetamines and, in particular, reduced exposure levels as compared to ADDERALL XR. The reduction in exposure is detectable; and assays for detecting exposure levels and comparing exposure levels are known in the art.

The inventors also observed that, when the compositions described herein are introduced into a dissolution medium substantially contemporaneously with ethanol, dose dumping of an ADHD effective agent (e.g., amphetamines) is reduced compared to introducing a reference listed drug (e.g., ADDERALL XR) into the same dissolution medium substantially contemporaneously with ethanol. As such, the invention relates to methods of reducing dose dumping of amphetamines in vitro and, in particular, reduced dose dumping as compared to ADDERALL XR. The reduction in dose dumping is detectable; and assays for detecting dose dumping levels and comparing such levels are known in the art. For example, cumulative release in vitro may be measured for the initial portion of the release curve, e.g., the first 0.5, 1, 1.5, 2, or 3 hours. Dose dumping may be evaluated from a partial area under the curve measurement to a relevant time point.

Dosage Forms Bioequivalent to a Target Product

The invention provides for dosage forms, methods of making dosage forms, and methods of administering dosage forms (e.g., for the conditions described herein such as ADHD) that are bioequivalent to a target product. In various embodiments, the invention provides for dosage forms (e.g., a liquid drug suspension, orally disintegrating tablet) that are bioequivalent to the in vivo serum profile of ADDERALL XR, or METADATE CD methods of making such dosage forms, and methods of treatment (as described herein) using such dosage forms. In particular embodiments, the compositions have complete and/or partial profiles (e.g., partial AUCs) that are bioequivalent to the profiles of ADDERALL XR or METADATE CD. Examples 16 and 17 describe such compositions. For example, the invention encompasses compositions that, when administered to a human, produce a mean plasma concentration profile which has any one of $AUC_{0-3}$, $AUC_{0-4}$, $AUC_{0-5}$, $AUC_{0-tmax}$, $AUC_{4-12}$, $AUC_{5-12}$, $AUC_{tmax-12}$, $AUC_{5-24}$, $AUC_{tmax-24}$, $AUC_{5-t}$, $AUC_{tmax-t}$ $AUC_{0-24}$ and/or $AUC_{0-\infty}$ (e.g., at least 2, 3, 4, 5, 6, 7, 8, 9, 10, 11, 12 and/or 13 AUC values) that is/are bioequivalent to the corresponding profiles of ADDERALL XR or METADATE CD.

Figure 23:
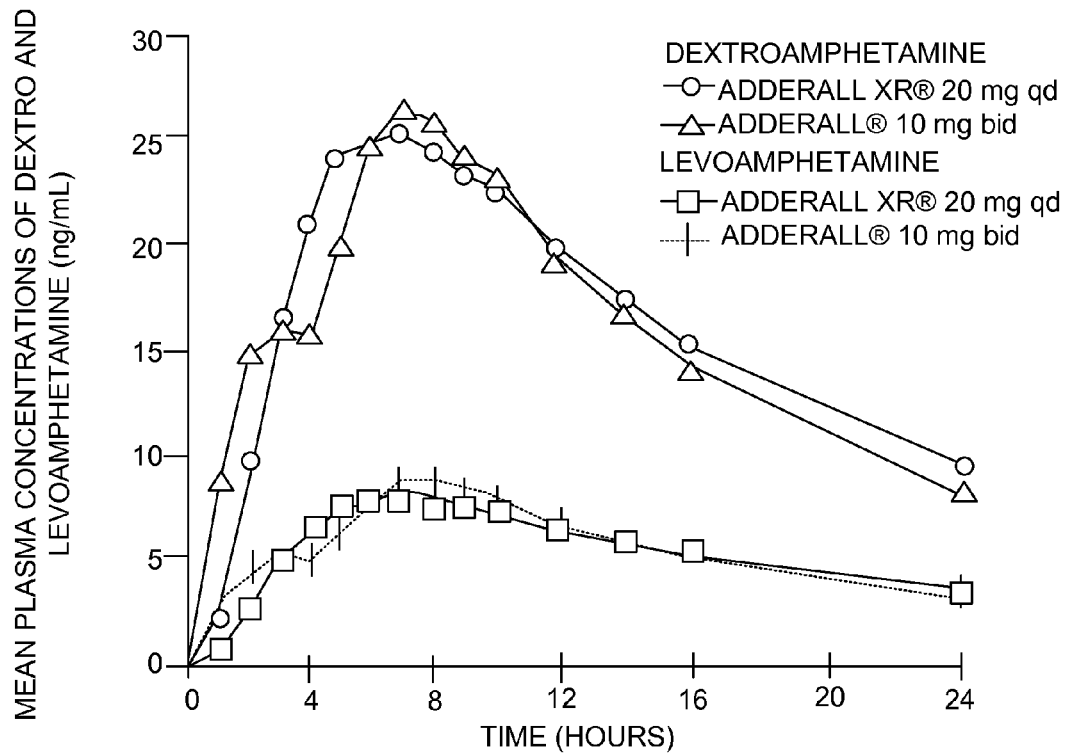
FIG. 23 shows the mean d-amphetamine and l-amphetamine plasma concentrations following administration of ADDERALL XR 20 mg (8 am) and ADDERALL (immediate-release) 10 mg twice daily (8 am and noon) in the fed state as reported in the prior art.
Figure 24:
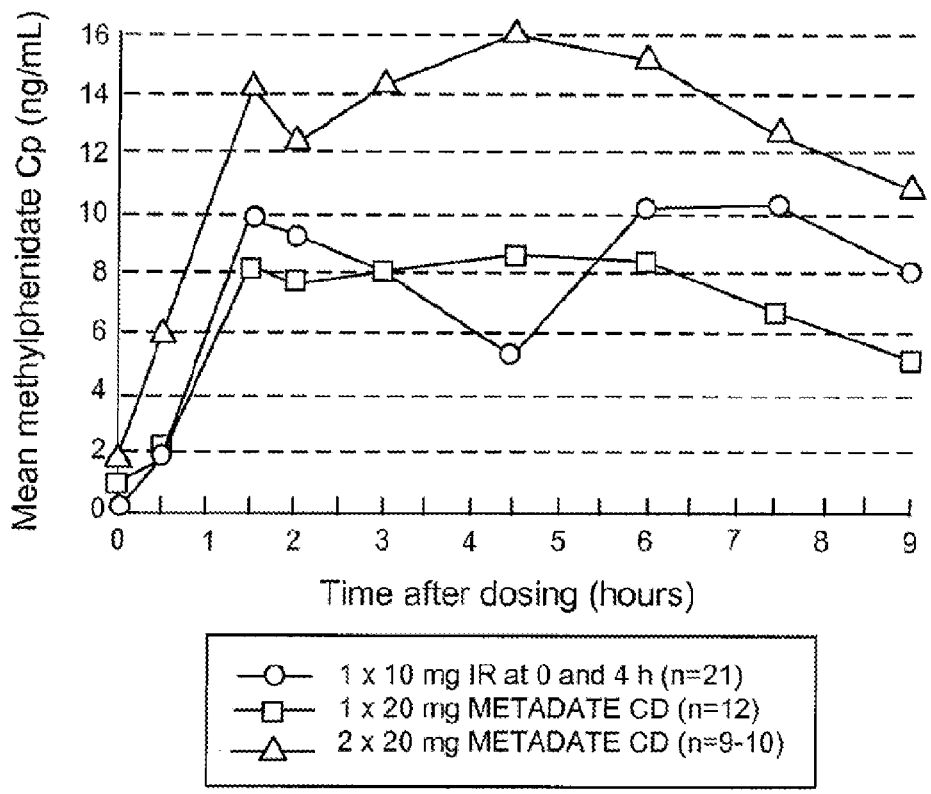
FIG. 24 shows the mean plasma concentrations following administration of immediate release methylphenidate and METADATE CD formulations as reported in the prior art.

U.S. Pat. Nos. 6,322,819 and 6,605,300, which are hereby incorporated by reference in their entirety, provide release profiles and plasma concentrations of ADDERALL XR. See also FIG. 23.

In another embodiment, the invention provides for dosage forms (e.g., orally disintegrating tablet) that are statistically similar and/or have partial AUCs with 90% confidence intervals that are within 80-125% of METADATE CD. For example, Example 18 describes compositions in which d-methylphenidate and total methylphenidate (d+1) are statistically similar and/or have $AUC_{last}$ and $AUC_{inf}$ with 90% confidence intervals that are within 80-125% of METADATE CD; but which does not have $T_{max}$ that is substantially similar.

EXAMPLES

The following examples describe various compositions encompassed within the invention and their corresponding dissolution and in vivo serum profiles. These examples are not intended to limit the invention in any way.

Example 1

Loading the Resin Particles with Drug

The invention relates pharmaceutical compositions comprising drug-resin particles and the methods of making these compositions. This example provides an exemplary method of loading amphetamines onto resin particles. FIG. 1 depicts this loading method.

In a kettle, amphetamine sulfate and dextroamphetamine sulfate are mixed in purified water until fully dissolved. AMBERLITE IRP 69 resins are added to the kettle and mixed. The solution is filtered through a 20 μm filter (Grade 54), then again through a 8 μm filter (Grade 540). The loaded resinate is collected on the filter paper during each filtration.

In a kettle, polyethylene glycol is mixed in purified water until fully dissolved. After it is completely dissolved, the loaded resinate is added, and the solution is mixed until uniform. The solution is filtered through a 20 μm filter (Grade 54), then again through a 8 μm filter (Grade 540). The loaded resinate/PEG is collected on the filter paper during each filtration.

The loaded resinate/PEG is dried in an oven until Loss on Drying is between 3% and 7%. The dried material is screened through a 100-mesh and 325-mesh screen.

The material that passed through the 100-mesh screen, but did not pass through the 325-mesh screen, is collected. This material is used as the uncoated delayed release resinate. Alternatively, this material could be used as a substitute immediate release resinate.

The material that did not pass through the 100-mesh screen is milled using a Fitzmill (with knives forward and a 50-mesh screen). This material is added together with the material that passed through the 325-mesh screen to become the immediate release resinate. These two materials are blended together.

Example 2

Coating Drug-resin Particles

The pharmaceutical compositions of the invention may comprise a coated and uncoated plurality of drug-resin particles. The coated drug-resin particles provide the delayed or triggered-release portion of the composition. This example provides an exemplary method of preparing a polymer coating for the coated drug-resin particles.

A clean, stainless steel container is pre-weighed. Acetone and ethanol are added to the container. Plasticizer is then added to the container and mixed until dispersed. A coating polymer such as HPMC, is slowly added to the container while mixing. The polymer solution is continuously stirred for at least an hour and until all of the solids are dissolved. This coating solution is continuously stirred during the coating process. The loaded resinate of Example 1 may be coated (e.g., in a wurster coater) with this coating solution to prepare coated drug-resin complexes.

Example 3

Loading Resin Particles with Drug and Coating the Drug-resin Particles

The methods of Examples 1 and 2 may be combined to prepare the pharmaceutical compositions of the invention. In particular, drug-resin particles may be prepared using the method of Example 1, and those drug-resin particles to be used as the delayed release portion of the composition may be coated with a polymer coating prepared by the method of Example 2. The particles may be dried and mixed in a V-blender. The specific ratio of immediate release and delayed release particles may vary as described below.

Once the resin particles are loaded, coated, and mixed, the resulting drug-resin particles may be used in any suitable dosage form (e.g., suspension, chewable composition, orally disintegrating composition, capsule, tablet, etc.).

Example 4

Orally Disintegrating Tablet with 45% IR and 55% DR (Formula A)

An orally disintegrating tablet was formulated with 45% of the amphetamine from immediate release resin complex and 55% of the amphetamine from a delayed release resin complex. A hydroxypropyl methylcellulose (HPMC) coating overlays the delayed released resin complex. The formula is presented below in Table 1.

TABLE 1

ODT amphetamine formulation with 45% IR and 55% DR with HPMC Overcoat
IR—34.17% base assay & DR—6.26% base assay: These values will be variable.

| | Formula A (HPMC overcoat) (45% active from IR Resin & 55% active from DR Resin) | | |
|---|---|---|---|
| | mg/dose | Notes | % |
| Uncoated (IR) AMP Resin Amphetamine (base) | 24.76 4.23 | The 24.76 mg/dose quantity is the actual amount of IR resin (at | 3.75 |

TABLE 1-continued

ODT amphetamine formulation with 45% IR and 55% DR with HPMC Overcoat
IR—34.17% base assay & DR—6.26% base assay: These values will be variable.

| | Formula A (HPMC overcoat) (45% active from IR Resin & 55% active from DR Resin) | | |
|---|---|---|---|
| | mg/dose | Notes | % |
| Dextroamphetamine (base) | 4.23 | a 34.17% assay value) | |
| AMBERLITE IRP069 Resin | 13.82 | that went into each tablet. | |
| Humectant | 1.24 | The values in the gray area are | |
| Purified Water | 1.24 | the quantities of each material that compromise the IR material. | |
| Coated (DR) AMP Resin | 165.08 | The 165.08 mg/dose quantity is | 25.01 |
| Amphetamine (base) | 5.17 | the actual amount of DR resin (at | |
| Dextroamphetamine (base) | 5.17 | a 6.26% assay value) | |
| AMBERLITE IRP069 Resin | 16.89 | that went into each tablet. | |
| Polyethylene Glycol | 1.51 | The IR resin material was used to | |
| Purified Water | 1.51 | make the 165.08 mg/dose DR | |
| HPMC Overcoat | 43.92 | material. | |
| EUDRAGIT L100 | 77.27 | The values in the gray area are | |
| Plasticizer | 13.64 | the quantities of each material that compromise the DR material. | |
| Excipients | 470.16 | | 71.24 |
| Total | 660.00 mg | | 100% |

Dissolution Method

Dissolution Parameters:

Dissolution testing is carried out using a USP Apparatus 2 with cannulas and cannula filters (Quality Lab Accessories, Porus Micron full flow filters 20 micron); paddle speed—100 rpm; kettle size—1000 mL; temperature—37.0±0.5° C.; filter—25 mm 0.45 um PVDF w/GMF; syringe—B-D10 mL Luer-Lok.

Dissolution Media:

The medium for the dissolution assay is 900 mL of 0.1N HCl for the first hour; after 2 hour time point~100 mL of potassium phosphate/sodium hydroxide solution is added to bring to pH~6.8.

The sample is weighed and is placed into the corresponding kettle, and the dissolution timing started.

Sampling pull times are 30 minutes, 1 hour, 2 hours, 3 hours, and 4 hours. For each sample pull time and each kettle, 10 mL of sample are pulled into a B-D 10 mL Luer-Lok syringe and returned to the kettles before the sample pull to flush out the cannula from the prior pulls. 2 ml are then pulled for filtration and placed into an HPLC vial. Non-media replacement and volume changes from the two media changes are calculated.

Figure 2:
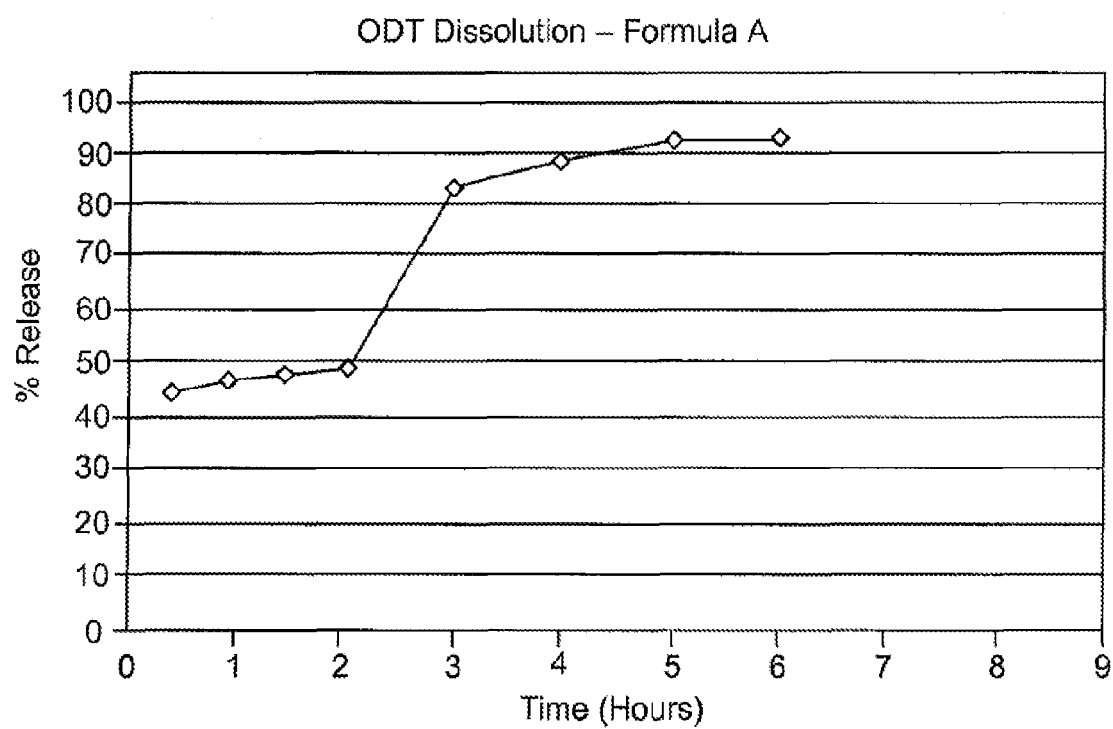
FIG. 2 shows the dissolution profile of the composition described in Example 4.

Dissolution Profile:

The amount of drug in the filtrate at each time point is determined by HPLC, and the percentage released from the drug-resin is plotted in FIG. 2.

The same profile was obtained without the use of the HPMC overcoat.

Example 5

Orally Disintegrating Tablet with 30% IR and 70% DR (Formula B)

An orally disintegrating tablet was formulated with 30% of the amphetamine from immediate release resin complex and 70% of the amphetamine from a delayed release resin complex. An HPMC coating overlays the delayed released resin complex. The formula is presented in Table 2.

TABLE 2

ODT amphetamine formulation with 30% IR and 70% DR with HPMC Overcoat
IR—34.17% base assay & DR—6.26% base assay: These values will be variable.

| | Formula B (HPMC overcoat) (30% active from IR Resin & 70% active from DR Resin) | | |
|---|---|---|---|
| | mg/dose | Notes | % |
| Uncoated (IR) AMP Resin | 16.50 | The 16.50 mg/dose quantity is | 2.50 |
| Amphetamine (base) | 2.82 | the actual amount of IR resin (at | |
| Dextroamphetamine (base) | 2.82 | a 34.17% assay value) | |
| AMBERLITE IRP069 Resin | 13.82 | that went into each tablet. | |
| Humectant | 1.24 | The values in the gray area are | |
| Purified Water | 1.24 | the quantities of each material that compromise the IR material. | |
| Coated (DR) AMP Resin | 210.12 | The 210.12 mg/dose quantity is | 31.84 |
| Amphetamine (base) | 6.58 | the actual amount of DR resin (at | |
| Dextroamphetamine (base) | 6.58 | a 6.26% assay value) | |
| AMBERLITE IRP069 Resin | 21.50 | that went into each tablet. | |

TABLE 2-continued

ODT amphetamine formulation with 30% IR and 70% DR with HPMC Overcoat
IR—34.17% base assay & DR—6.26% base assay: These values will be variable.

|  | Formula B (HPMC overcoat) (30% active from IR Resin & 70% active from DR Resin) | | |
|---|---|---|---|
|  | mg/dose | Notes | % |
| Humectant | 1.92 | The IR resin material was used to make the 210.12 mg/dose DR material. | |
| Purified Water | 1.92 | | |
| HPMC Overcoat | 55.91 | | |
| EUDRAGIT L100 | 98.35 | The values in the gray area are the quantities of each material that compromise the DR material. | |
| Triethyl Citrate | 17.36 | | |
| Excipients | 433.38 | | 65.66 |
| Total | 660.00 mg | | 100% |

The dissolution method is performed as described in the previous Example, except that sample pull times are 0.5, 1.0, 1.5, 2.0, 3.0, 4.0, 5.0, and 6.0 hours.

Figure 3:
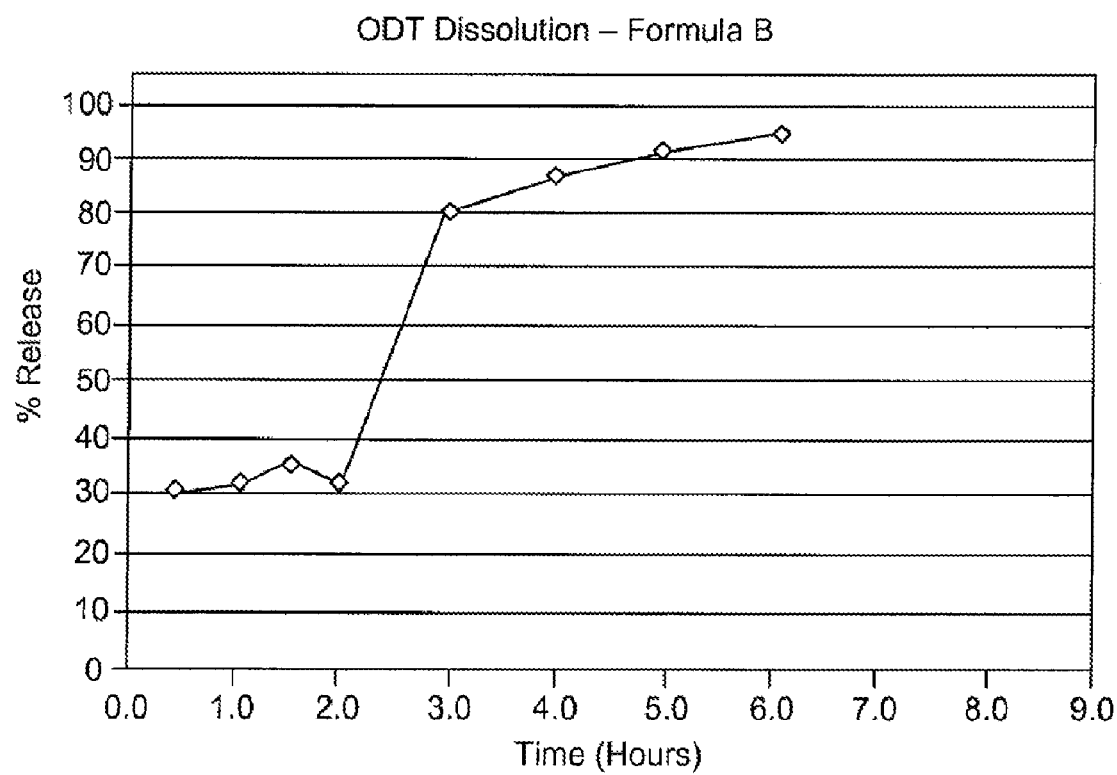
FIG. 3 shows the dissolution profile of the composition described in Example 5.

Dissolution Profile:

The amount of drug in the filtrate at each time point is determined by HPLC, and the percentage released from the drug-resin is plotted in FIG. 3.

The same profile was obtained without the use of the HPMC overcoat.

Example 6

Orally Disintegrating Tablet with 45% IR and 55% DR (Formula C)

An orally disintegrating tablet was formulated with 45% of the amphetamine from immediate release resin complex and 55% of the amphetamine from a delayed release resin complex. This formulation did not include an HPMC overcoat. The formula is presented in Table 3.

TABLE 3

ODT amphetamine formulation with 45% IR and 55% DR
IR—34.17% base assay & DR—8.53% base assay: (These values will be variable.)

|  | Formula C (no HPMC overcoat) (45% active from IR Resin & 55% active from DR Resin) | | |
|---|---|---|---|
|  | mg/dose | Notes | % |
| Uncoated (IR) AMP Resin | 24.76 | The 24.76 mg/dose quantity is the actual amount of IR resin (at a 34.17% assay value) that went into each tablet. | 3.75 |
| Amphetamine (base) | 4.23 | | |
| Dextroamphetamine (base) | 4.23 | | |
| AMBERLITE IRP069 Resin | 13.82 | | |
| Humectant | 1.24 | The values in the gray area are the quantities of each material that compromise the IR material. | |
| Purified Water | 1.24 | | |
| Coated (DR) AMP Resin | 121.16 | The 121.16 mg/dose quantity is the actual amount of DR resin (at an 8.53% assay value) that went into each tablet. | 18.36 |
| Amphetamine (base) | 5.17 | | |
| Dextroamphetamine (base) | 5.17 | | |
| AMBERLITE IRP069 Resin | 16.89 | | |
| Humectant | 1.51 | The IR resin material was used to make the 121.16 mg/dose DR material. | |
| Purified Water | 1.51 | | |
| HPMC 20% overcoat | — | | |
| EUDRAGIT L100 | 77.27 | The values in the gray area are the quantities of each material that compromise the DR material. | |
| Plasticizer | 13.64 | | |
| Excipients | 514.08 | | 77.89 |
| Total | 660.00 mg | | 100% |

The dissolution method is performed as described in Example 4, except that sample pull times are 0.5, 1.0, 1.5, 2.0, 3.0, 4.0, 5.0, 6.0, 7.0, and 8.0 hours.

Figure 4:
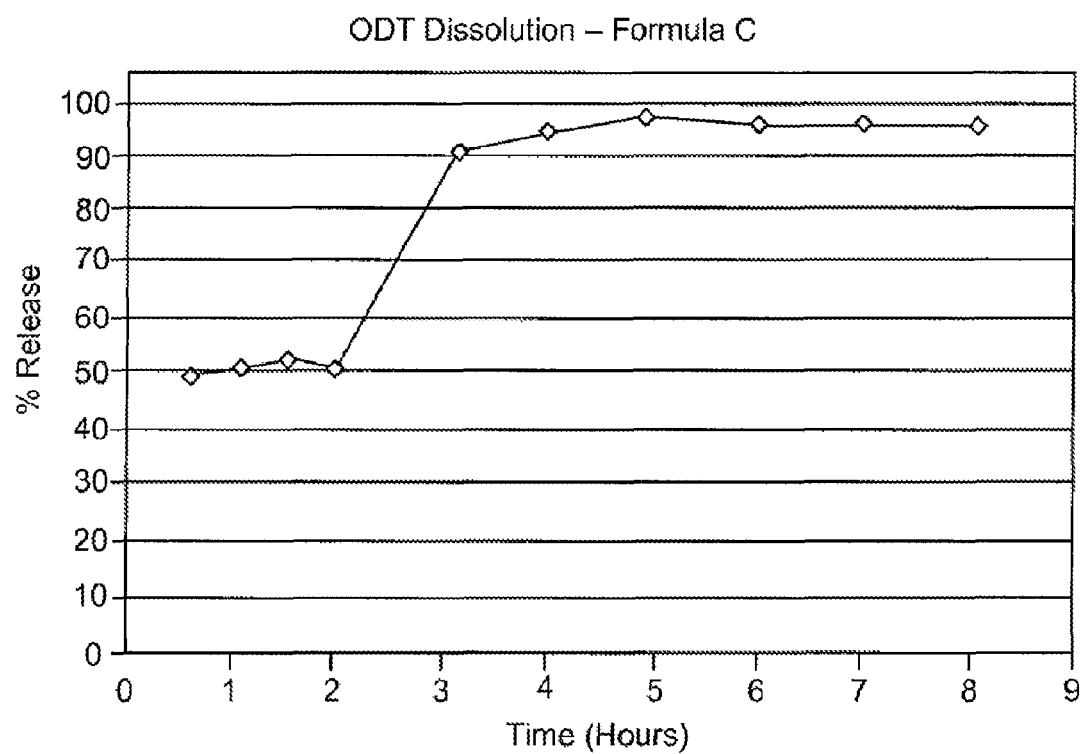
FIG. 4 shows the dissolution profile of the composition described in Example 6.

Dissolution Profile:

The amount of drug in the filtrate at each time point is determined by HPLC, and the percentage released from the drug-resin is plotted in FIG. 4.

Example 7

Suspension with 50% IR and 50% DR (Formula A1)

A suspension was formulated with 50% of the amphetamine from immediate release resin complex and 50% of the amphetamine from a delayed release resin complex. The resin was IRP-69. The delayed release resin complexes coated with 15% TEC, and 70% EUDRAGIT L100. The formulation is presented in Table 4.

TABLE 4

Suspension amphetamine formulation with 50% IR and 50% DR

| Ingredient | Application | Amount per 15 ml |
|---|---|---|
| Purified Water | Diluent | 7.9 g |
| Ascorbic Acid | pH | 6.00 mg |
| Propylene Glycol | Solvent | 525.00 mg |
| Methylparaben | Preservative | 12.00 mg |
| Propylparaben | Preservative | 1.50 mg |
| Polysorbate 80 | Surfactant | 15.00 mg |
| Xanthan Gum | Suspending Agent | 90.00 mg |
| Vegetable (Corn) Oil | Viscosity Agent | 30.00 mg |
| Amphetamine Uncoated Resin | Active Resin | 27.57 mg |
| Amphetamine Coated Resin | Active Resin | 76.19 mg |
| Sucrose | Sweetener | 2250.00 mg |
| High Fructose Corn Syrup | Sweetener | 6750.00 mg |

The dissolution method was performed as described in Example 4, except that the samples were pulled at different time points: 0.5, 1.0, 1.5, 2.0, 2.5, 3.0, 4.0, and 6.0 hours.

Figure 5:
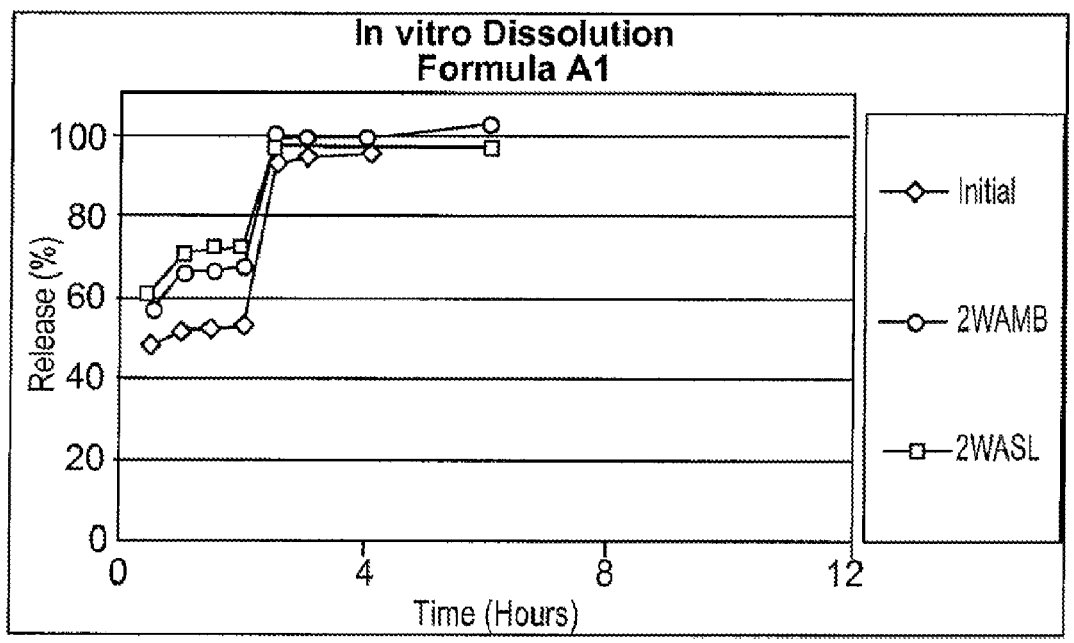
FIG. 5 shows the dissolution profile of the composition described in Example 7.

Dissolution Profile:

The amount of drug in the filtrate at each time point was determined by HPLC, and the percentage released from the drug-resin is plotted in FIG. 5 and reflected below.

| Leakage | Initial | 2 W AMB[1] | 2 W ASL[2] |
|---|---|---|---|
| 30 Mins (% Release): | 47.9 | 56.8 | 60.3 |
| @ 2 Hours (% Release): | 51.5 | 67.2 | 72.4 |
| Profile (% Release) Hours | | | |
| 0.5 | 47.9 | 56.8 | 60.3 |
| 1 | 51.5 | 66.7 | 70.5 |
| 1.5 | 52.2 | 66.1 | 72.5 |
| 2 | 52.8 | 67.2 | 72.4 |
| 2.5 | 93.4 | 100.2 | 97.8 |
| 3 | 94.9 | 99.9 | 97.8 |
| 4 | 95.6 | 100.1 | 98.1 |
| 6 | | 102.5 | 98.2 |

[1]Two weeks under ambient conditions.
[2]Two weeks under accelerated shelf life conditions.

Example 8

ODT with 50% IR and 50% DR (Formula D)

An orally disintegrating tablet was formulated with 50% of the amphetamine from immediate release resin complex and 50% of the amphetamine from a delayed release resin complex. This formulation was similar to Examples 4-6 and is reflected in Table 5. The resin was IRP-69. The delayed release coated resin comprised 15% TEC, and 70% EUDRAGIT L100.

TABLE 5

ODT amphetamine formulation with 50% IR and 50% DR.

| Ingredient | Application | Amount per tablet |
|---|---|---|
| Amphetamine Resin IR | Active Resin I (Assay - 16.9%) | 38.10 mg |
| Amphetamine Resin DR | Active Resin II (Assay - 46.7%) | 13.79 mg |
| Ludiflash | Compressing Agent | 371.11 mg |
| Croscarmellose Sodium | Disintegrant | 22.50 mg |
| Magnesium Stearate | Lubricant | 4.50 mg |

The dissolution method was performed as described in Example 4, except that the samples were pulled at different time points.

Figure 6:
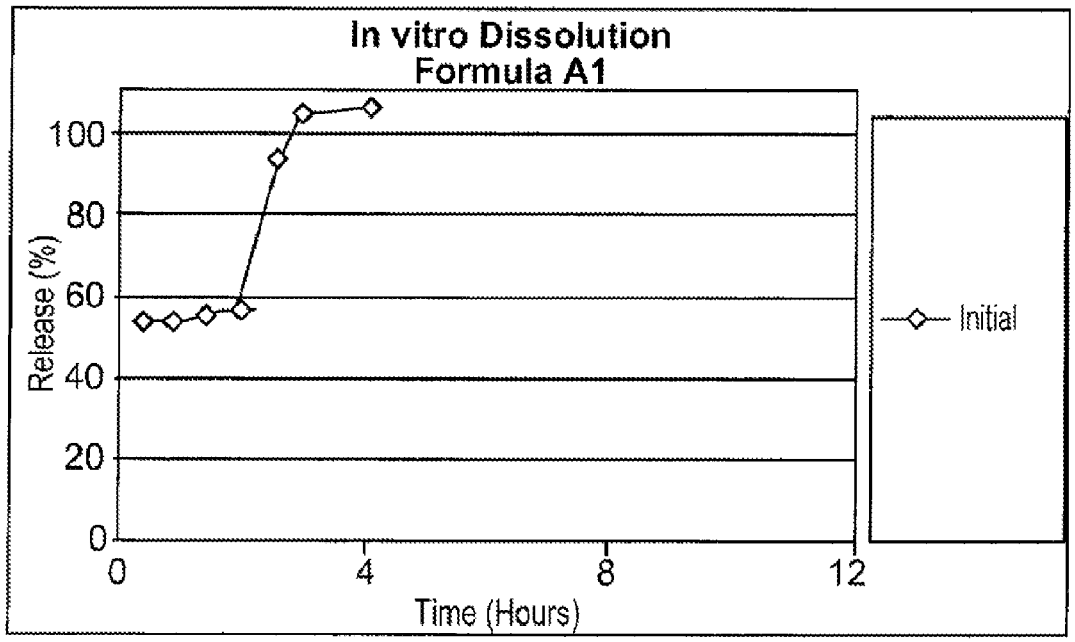
FIG. 6 shows the dissolution profile of the composition described in Example 8.

Dissolution Profile:

The amount of drug in the filtrate at each time point was determined by HPLC, and the percentage released from the drug-resin is plotted in FIG. 6 and reflected below.

| Profile (% Release) Hours | |
|---|---|
| 0.5 | 50.5 |
| 1 | 51.0 |
| 1.5 | 51.5 |
| 2 | 52.4 |
| 2.5 | 85.3 |
| 3 | 96.0 |
| 4 | 96.9 |

Example 9

ODT with 35% IR and 65% DR (Formula E)

An orally disintegrating tablet was formulated with 35% of the amphetamine from immediate release resin complex and 65% of the amphetamine from a delayed release resin complex. This formulation was similar to Examples 4-6 and is reflected in Table 6. Unlike these examples, however, the resin was an IRP-64 resin. The delayed release coated resin comprised 15% HPMC, 15% TEC, and 110% EUDRAGIT L100.

TABLE 6

ODT amphetamine formulation with 35% IR and 65% DR with HPMC Overcoat

| Ingredient | Application | Amount per tablet |
|---|---|---|
| Amphetamine Resin DR | Active Resin I (Assay - 6.5%) | 128.8 mg[1] |
| Amphetamine Resin IR | Active Resin II (Assay - 63.73%) | 7.07 mg[2] |
| Ludiflash | Compressing Agent | 287.13 mg |
| Croscarmellose Sodium | Disintegrant | 22.50 mg |
| Magnesium Stearate | Lubricant | 4.50 mg |

The dissolution method was performed as described in Example 4, except that the samples were pulled at different time points.

Dissolution Profile

Figure 7:
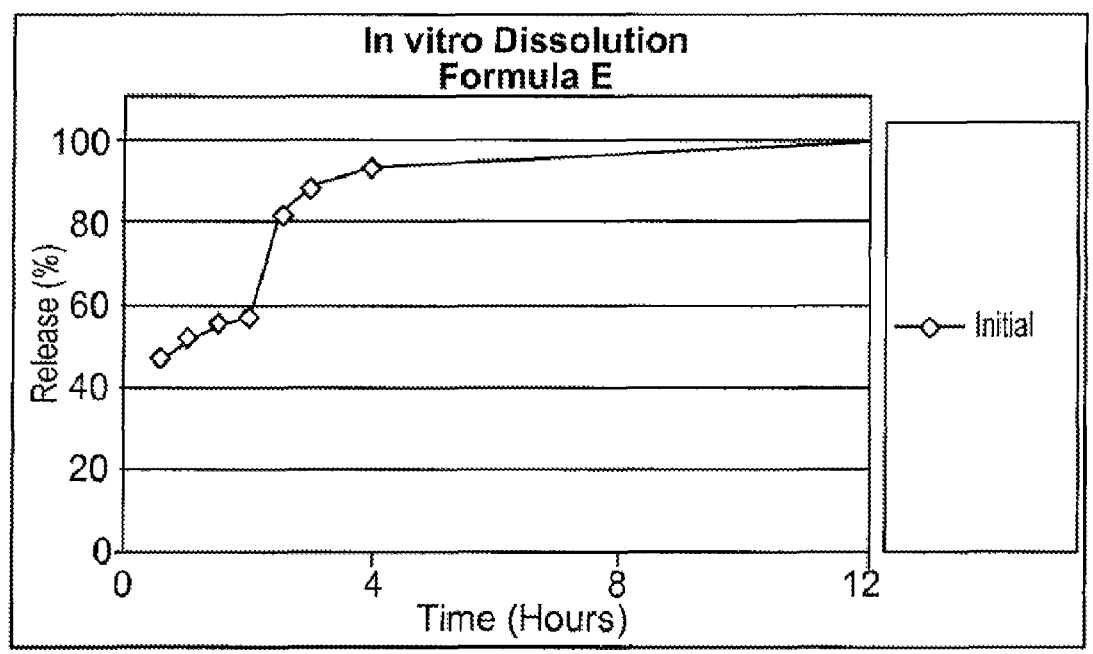
FIG. 7 shows the dissolution profile of the composition described in Example 9.

The amount of drug in the filtrate at each time point was determined by HPLC, and the percentage released from the drug-resin is plotted in FIG. 7 and reflected below.

| Hours | Profile (% Release) |
|---|---|
| 0.5 | 47.6 |
| 1 | 52.4 |
| 1.5 | 56 |
| 2 | 58.2 |
| 2.5 | 81.8 |
| 3 | 88.9 |
| 4 | 93.4 |
| 24 | 108.3 |

Example 10 pH Study

A pH study was also conducted to compare a control and four different coated drug-resin particles prepared according to the methods described in Examples 1 and 2 for the following coatings and resins: (1) 70% EUDRAGIT L100/IRP69; (2) 110% EUDRAGIT L100/IRP 64; (3) 40% EUDRAGIT L100-55/IRP 69; (4) 70% EUDRAGIT L100-55/IRP 64.

pH Study Protocol:

The medium for the dissolution assay is 0.1N HCl. pH change buffer described in the previous examples is added, drop wise, until a pH of 2.0, 3.0, 4.0, 5.0, 5.2, 5.3, 5.4, 5.5, 5.6, 5.7, 5.8, 5.9, 6.0, 6.1, 6.2, and 6.5 is reached. At each pH point, 2 mL of sample was removed and then pH change buffer solution is added to adjust pH to next pH target. The next sample is taken 10 minutes after adjusted pH.

Figure 8:
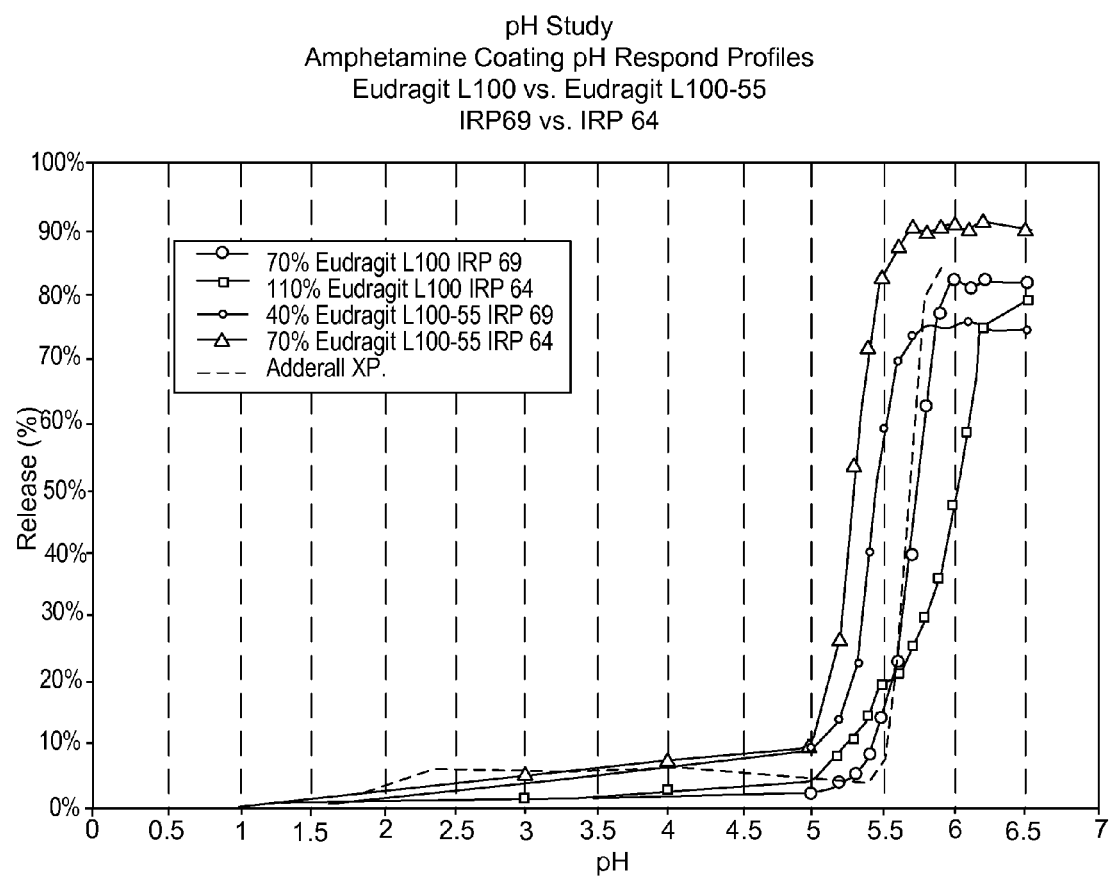
FIG. 8 shows the results of a pH study on different coated resins described in Example 10.

Varying the coating and the resin composition shifted the release curve as shown in FIG. 8. EUDRAGIT L100 and IRP69 gave results closest to the pH for release observed with ADDERALL XR.

Example 11

Pig Study Using Pharmaceutical Compositions

This study is an open-label, random order, crossover comparison study of three test formulations (two tablets and one liquid suspension) and the currently marketed reference drug (ADDERALL XR). In vivo studies are performed using pigs. A total of 12 animals are initially assigned to study (3 males per group×4 groups). All animals are fasted overnight prior to dosing and through the first 4 hours of blood sample collection (total fasting time not to exceed 24 hours). Water is available ad libitum. Animals are dosed on days 1, 4, 8, and 15).

Phase 1: Each animal in Groups 1 and 2 receives a 2 tablet dose of the appropriate test article formulation as outlined in the study design in Table 7 below. Each animal in Group 4 receives a 1 capsule dose of the reference formulation as outlined in Table 7. A balling gun may be used, if appropriate, to facilitate dosing. Whether animals are hand-dosed or a balling gun is used for dosing, a subsequent 10 mL tap water rinse is administered orally following dosing. Each animal in Group 3 receives a single oral gavage (PO) dose of the appropriate test article formulation as outlined in the study design table below. The dosing syringes are weighed when loaded with the test formulation and then again following dose administration for each animal (i.e. loaded and delivered syringe weights). Oral gavage dosing formulations will be continuously stirred throughout dosing. The gavage tube should be rinsed with approximately 10 mL of tap water following dosing (prior to removal of the gavage tube).

Phase 2: Following a washout at least 3 days, each animal in Groups 2 and 3 receives a 2 tablet dose of the appropriate test article formulation as outlined in Table 7. Each animal in Group 1 receives a 1 capsule dose of the reference formulation as outlined in Table 7. A balling gun may be used, if appropriate, to facilitate dosing. Whether animals are hand-dosed or a balling gun is used for dosing, a subsequent 10 mL tap water rinse is administered orally following dosing. Each animal in Group 4 receives a single oral gavage (PO) dose of the appropriate test article formulation as outlined in the study design table below. The dosing syringes should be weighed when loaded and then again following dose administration for each animal (i.e. loaded and delivered syringe weights). Oral gavage dosing formulations should be continuously stirred throughout dosing. The gavage tube should be rinsed with approximately 10 mL of tap water following dosing (prior to removal of the gavage tube).

Phase 3: Following a washout of at least 3 days, each animal in Groups 3 and 4 receives a 2 tablet dose of the appropriate test article formulation as outlined in Table 7. Each animal in Group 2 receives a 1 capsule dose of the reference formulation as outlined in Table 7. A balling gun may be used, if appropriate, to facilitate dosing. Whether animals are hand-dosed or a balling gun is used for dosing, a subsequent 10 mL tap water rinse is administered orally following dosing. Each animal in Group 1 receives a single oral gavage (PO) dose of the appropriate test article formulation as outlined in the study design table below. The dosing syringes are weighed when loaded and then again following dose administration for each animal (i.e. loaded and delivered syringe weights). Oral gavage dosing formulations are continuously stirred throughout dosing. The gavage tube is rinsed with approximately 10 mL of tap water following dosing (prior to removal of the gavage tube).

Phase 4: Following a washout of at least 3 days, each animal in Groups 1 and 4 receives a 2 tablet dose of the appropriate test article formulation as outlined in Table 7. Each animal in Group 3 receives a 1 capsule dose of the reference formulation as outlined in Table 7. A balling gun may be used, if appropriate, to facilitate dosing. Whether animals are hand-dosed or a balling gun is used for dosing, a subsequent 10 mL tap water rinse is administered orally following dosing. Each animal in Group 2 receives a single oral gavage (PO) dose of the appropriate test article formulation as outlined in the study design table below. The dosing syringes are weighed when and then again following dose administration for each animal (i.e. loaded and delivered syringe weights). Oral gavage dosing formulations are continuously stirred throughout dosing. The gavage tube is rinsed with approximately 10 mL of tap water following dosing (prior to removal of the gavage tube).

TABLE 7

Pig study design.

| Group | Test Article | Number of Males* | Dose Route | Dose Level (mg) | Dose Volume/ Amount | Matrix Collected |
|---|---|---|---|---|---|---|
| | | | PHASE 1 | | | |
| 1 | Neos 2 Formulation #1 | 3 | Oral, tablet | 30 | 2 tablets (15 mg/tablet) | Blood[E] |
| 2 | Neos 2 Formulation #2 | 3 | Oral, tablet | 30 | 2 tablets (15 mg/tablet) | Blood[E] |
| 3 | Neos 2 Formulation #3 | 3 | PO, Liquid suspension | 30 | 15 mL | Blood[E] |
| 4 | Reference Drug (ADDERALL XR) Formulation | 3 | Oral, capsule | 30 | 1 capsule (30 mg/capsule) | Blood[E] |
| | | | PHASE 2 | | | |
| 1 | Reference Drug (ADDERALL XR) Formulation | 3 | Oral, capsule | 30 | 1 capsule (30 mg/capsule) | Blood[E] |
| 2 | Neos 2 Formulation #1 | 3 | Oral, tablet | 30 | 2 tablets (15 mg/tablet) | Blood[E] |
| 3 | Neos 2 Formulation #2 | 3 | Oral, tablet | 30 | 2 tablets (15 mg/tablet) | Blood[E] |
| 4 | Neos 2 Formulation #3 | 3 | PO, Liquid suspension | 30 | 15 mL | Blood[E] |
| | | | PHASE 3 | | | |
| 1 | Neos 2 Formulation #3 | 3 | PO, Liquid suspension | 30 | 15 mL | Blood[E] |
| 2 | Reference Drug (ADDERALL XR) Formulation | 3 | Oral, capsule | 30 | 1 capsule (30 mg/capsule) | Blood[E] |
| 3 | Neos 2 Formulation #1 | 3 | Oral, tablet | 30 | 2 tablets (15 mg/tablet) | Blood[E] |
| 4 | Neos 2 Formulation #2 | 3 | Oral, tablet | 30 | 2 tablets (15 mg/tablet) | Blood[E] |
| | | | PHASE 4 | | | |
| 1 | Neos 2 Formulation #2 | 3 | Oral, tablet | 30 | 2 tablets (15 mg/tablet) | Blood[E] |
| 2 | Neos 2 Formulation #3 | 3 | PO, Liquid suspension | 30 | 15 mL | Blood[E] |
| 3 | Reference (ADDERALL XR) Formulation | 3 | Oral, capsule | 30 | 1 capsule (30 mg/capsule) | Blood[E] |
| 4 | Neos 2 Formulation #1 | 3 | Oral, tablet | 30 | 2 tablets (15 mg/tablet) | Blood[E] |

[D] Reference Formulation is a Marketed Product. All capsules and tablets will be used as received.
[E] Blood samples will be collected predose and at approximately 1, 2, 3, 4, 5, 6, 7, 8, 9, 12, 16, and 24 hours postdose.
*The same animals will be used for each phase following a washout of at least 3 days.

For each phase, blood samples (approximately 2 mL/sample) are collected from the thoracic inlet (jugular vein, or other suitable vein) predose and at approximately 1, 2, 3, 4, 5, 6, 7, 8, 9, 12, 16, and 24 hours postdose and placed into tubes containing $K_2EDTA$. All blood samples are placed on an ice block (or wet ice) following collection. The samples are centrifuged and the resulting plasma is separated and stored frozen at approximately −70° C. until analyzed (following separation; the plasma may be initially placed on dry ice prior to being stored in the −70° C. freezer). Any clotted samples should be noted.

Plasma samples are analyzed for amphetamine over the range of 0.1 ng/mL to 200 ng/mL. Control plasma procured from a commercial source is used for all analyses. Each analysis batch includes duplicate calibration samples (one set run at beginning of batch and one at the end of batch) with a minimum of 6 non-zero levels, and duplicate QC samples prepared at 4 concentration levels. The calibration and QC samples are prepared from separate stocks. Acceptance criteria for each batch is that at least 75% of individual calibration points and 62.5% of the QC samples must be within +/−30% of the target concentration.

Example 12

In Vivo Study

Drug samples from Examples 4 and 5 were administered to pigs as described in Example 11. Capsules of ADDERALL XR were administered as controls under the same conditions.

Figure 9:
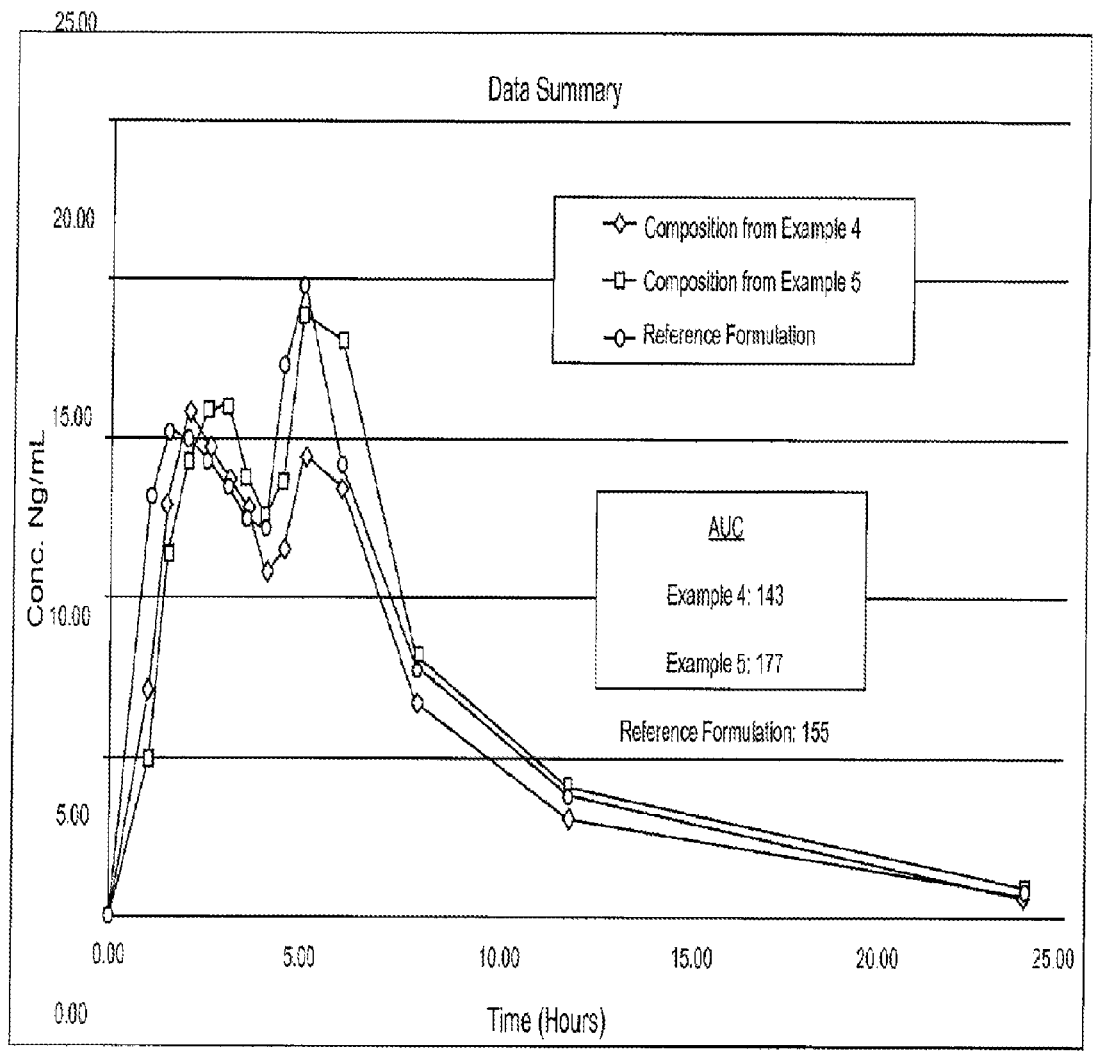
FIG. 9 shows the plasma concentrations of amphetamine released from two different amphetamine formulations compared to ADDERALL XR (i.e., the reference formulation) in the pig study described in Example 12.

Results of the pig study are depicted in FIG. 9. Outliers were excluded. FIG. 9 shows the plasma concentrations of drug released from the formulas in Examples 4 and 5 compared to ADDERALL XR (i.e., the reference formulation). The relative amounts of coated and uncoated particles differed between Examples 4 and 5; both compositions showed two peaks in the in vivo release profile, but with the composition having relatively more coated particles, the $T_{max}$ for both peaks is later, and the $C_{max}$ for the second peak is higher.

Thus, the skilled person can adjust the relative $C_{max}$ and AUC for each of the two peaks by adjusting the relative amounts of coated and uncoated drug-resin particles in the composition.

Example 13

Ethanol Study

A. In Vivo Study

The effects of ethanol were also tested. In vivo studies were carried out using drug samples similar to that from Example 6 administered to pigs as described in Example 11. The drug formulations were administered to pigs as described in Example 11, except that alcohol (240 ml of 20% ethanol) was also administered to the pigs contemporaneously. Capsules of ADDERALL XR were administered under the same conditions as controls.

Figure 10A:
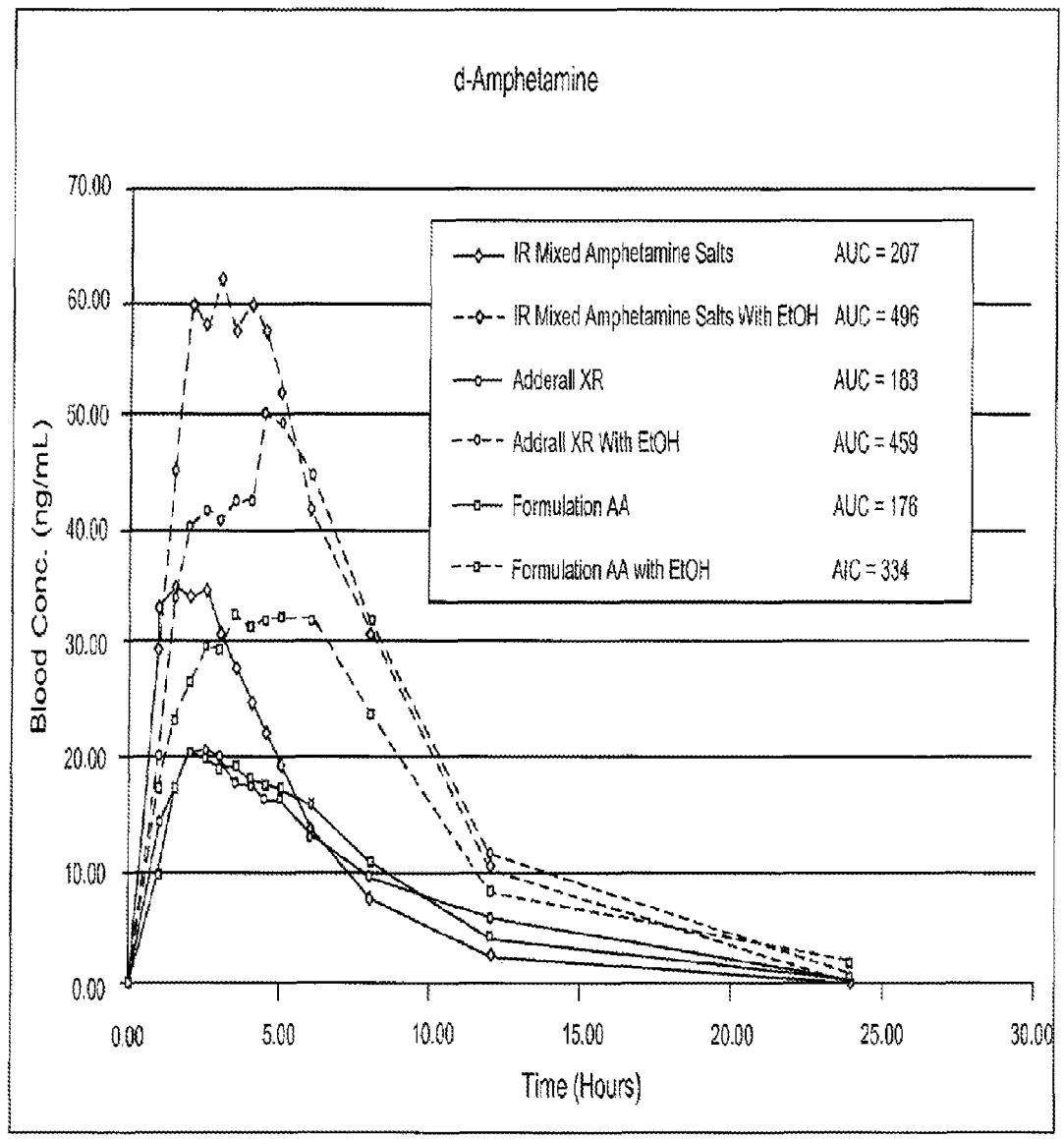
FIGS. 10A and 10B shows the plasma concentrations of exemplary amphetamine formulations compared to ADDERALL XR (i.e., the reference formulation) with alcohol and without alcohol as described in Example 13A.
Figure 10B:
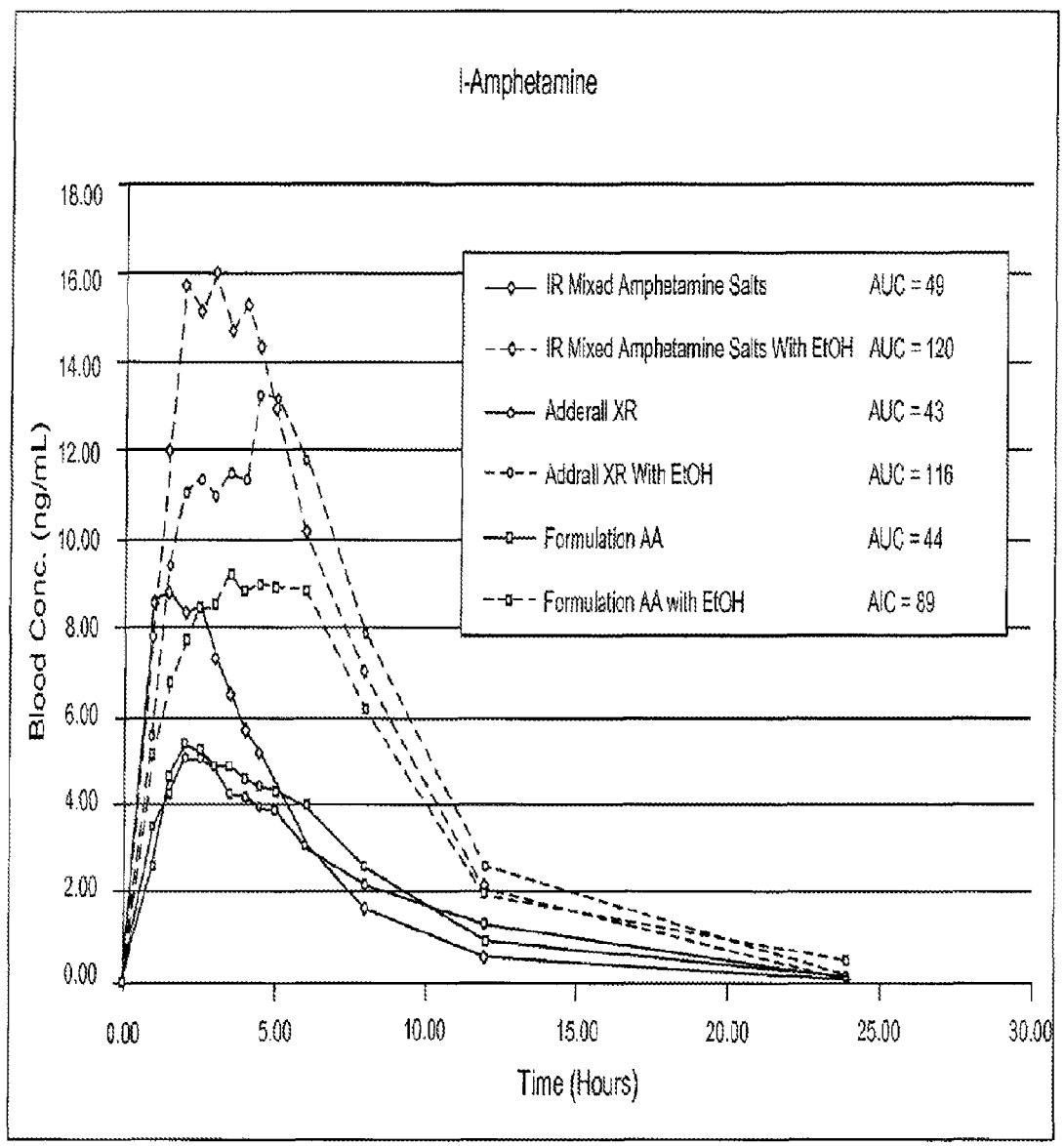

Results of the pig study are depicted in FIGS. 10A and 10B. Outliers were excluded. FIGS. 3A and 3B show the plasma concentrations of drug released from the resin formulas similar to that in Example 6 compared to ADDERALL XR (i.e., the reference formulation) and IR mixed amphetamines in the presence and absence of alcohol. The figures show (1) an increased exposure of amphetamines in the presence of alcohol; and (2) in the present of ethanol, formulations of the invention have a significantly reduced exposure level of amphetamines as compared to ADDERALL XR as demonstrated by comparison between the curves shown.

Often drugs products exhibit dose dumping in the presence of ethanol. This is one of the reason that the FDA asks for ethanol interaction studies on controlled release formulations. If a drug product showed dose dumping, all of the drug that is to be administered over time would become immediately available and adverse events could be seen. In contrast, the graph clearly shows that the integrity of the controlled release mechanism remains intact and two peaks can be distinguished. The first peak being the immediate release portion and the second peak being the still intact delayed release portion. The increased exposure, approximately 3 times the area under the curve (AUC), for both peaks is due to another physiological effect in the presence of ethanol such as impairment of the liver metabolism by the ethanol and thus lower first pass metabolism of the drug in the liver or other mechanism resulting in greater than expected blood levels for a given dose.

B. In Vitro Study

Figure 11:
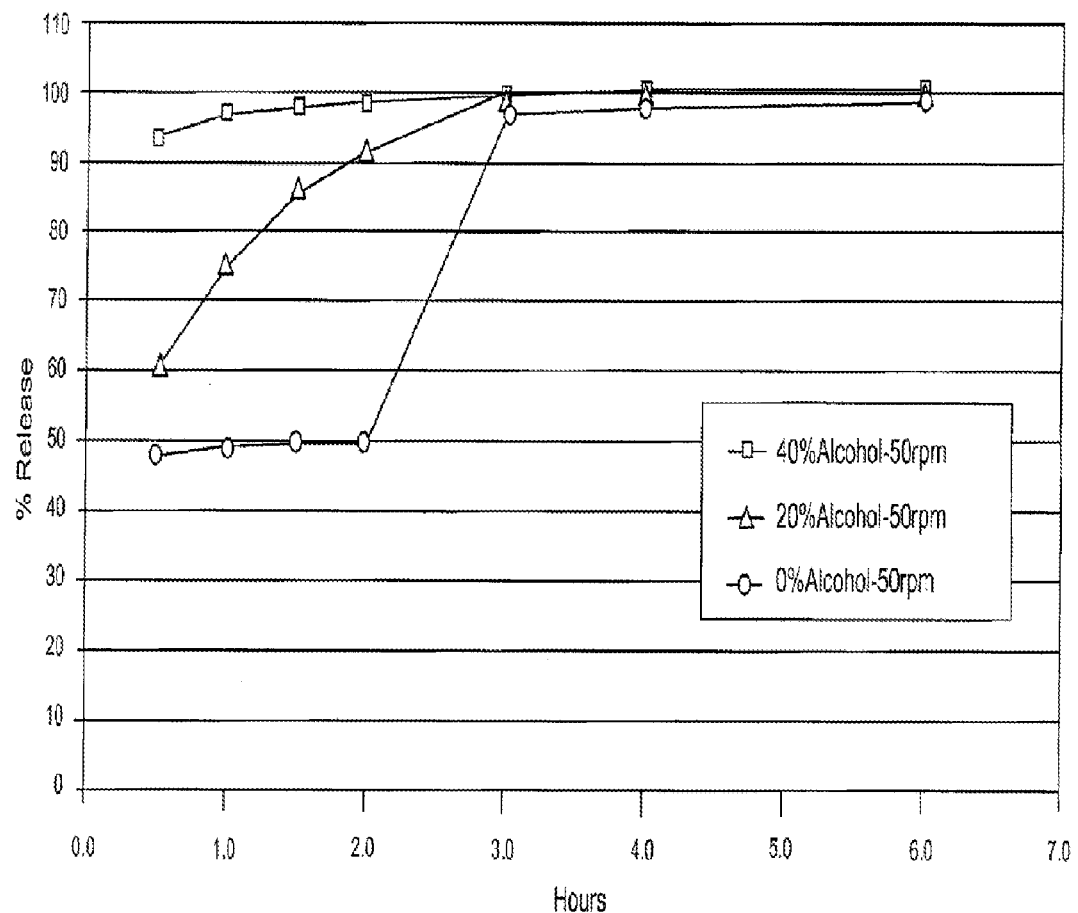
FIG. 11 shows in vitro release profiles of ADDERALL XR (i.e., the reference formulation) with the addition of 0%, 20%, and 40% alcohol as described in Example 13B.

In vitro dissolution studies using amphetamine compositions in the presence or absence of ethanol were also carried out. Drug compositions to be tested were introduced into USP dissolution Apparatus 2 as described above, except that the media started with alcoholic 0.1N HCl and samples were taken at different time points. FIG. 11 shows the release profiles of the ADDERALL XR reference formulation with 0%, 20%, and 40% ethanol. These results demonstrate that the addition of 20% or 40% ethanol substantially increases the amount of drug released in the reference formulation, i.e., there is a substantial increase in drug released through dose dumping in the presence of ethanol. This dose dumping may exacerbate the exposure of the subject to amphetamines which increases in vivo approximately 3 times in the presence of ethanol.

Figure 12:
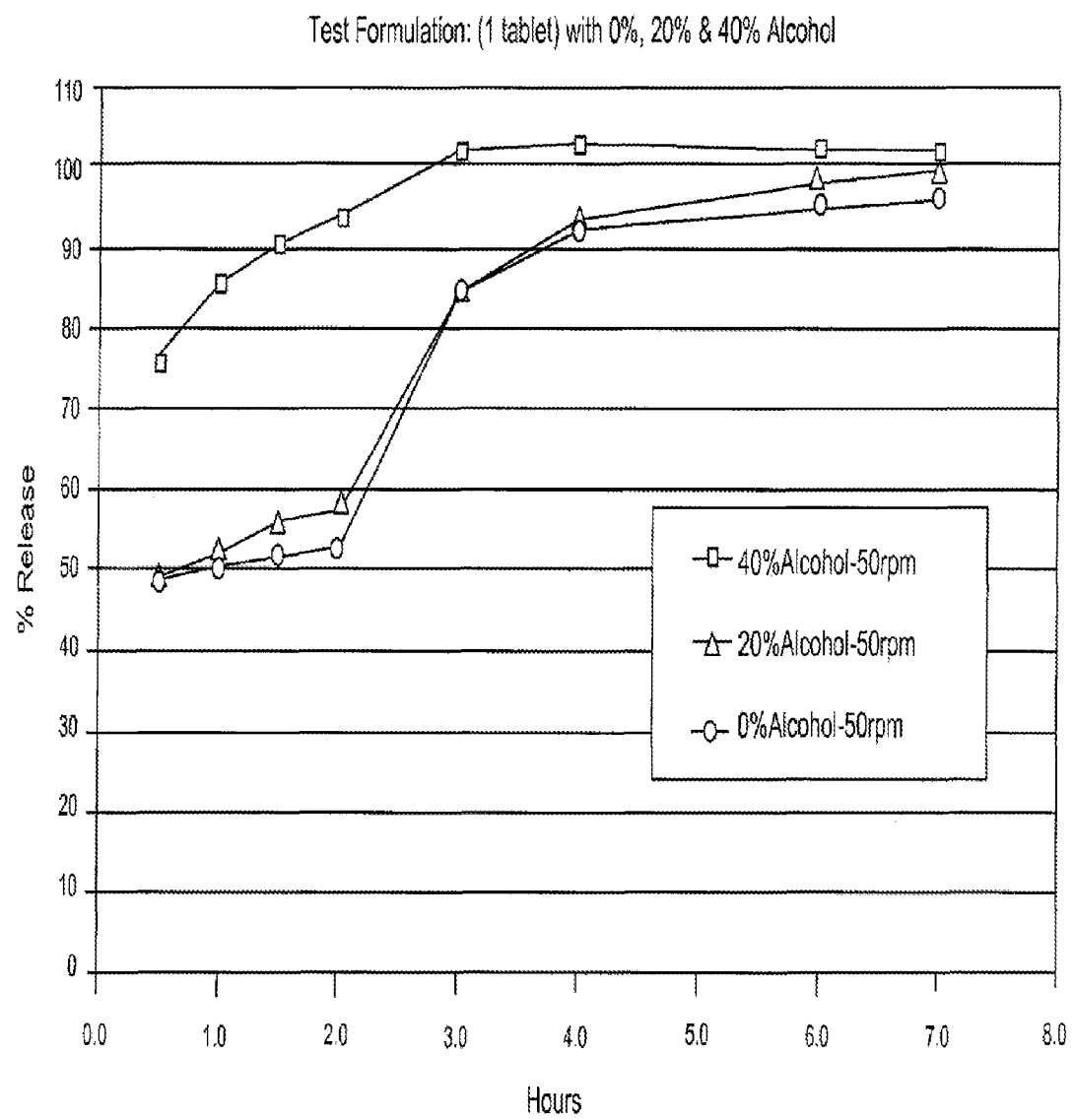
FIG. 12 shows the in vitro release profiles of the drug sample similar to that in Example 6 with the addition of 0%, 20%, and 40% alcohol as described in Example 13B.

FIG. 12 shows the release profiles of the drug sample similar to that from Example 6 with 0%, 20%, and 40% ethanol. These results demonstrate that the addition 20% ethanol does not substantially increase the amount of drug released. Moreover, the addition of 40% ethanol increases the amount of drug released but to a lesser extent than in the reference formulation. As such, the ethanol study's results show that, in the presence of ethanol, the formulations of the invention have a reduced exposure level of amphetamines as compared to the reference formulation. This prevents or substantially reduces the likelihood of dose dumping when the formulations of the invention and ethanol are ingested by a subject.

Example 14 pH Study

Figure 13:
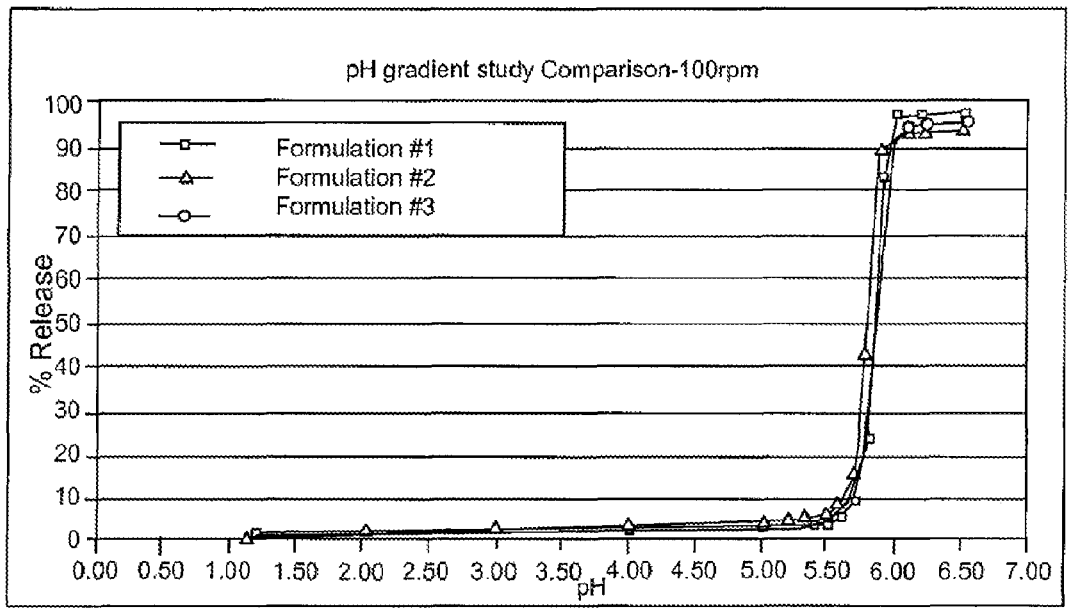
FIG. 13 shows the amount of drug released over a range of pHs for three different lots of the delayed release product described in Example 6.

A pH study was also conducted on the compositions administered to the pigs in Example 13. The dissolution and pH protocols are the same as described in Example 10. The results of the pH study on three different lots of the delayed release particles from Example 6 are depicted in FIG. 13.

Example 15

Human Pharmacokinetic Study Using ODT Pharmaceutical Compositions

This example describes a single-dose, open-label, randomized, three-period, three-treatment crossover study comparing the rate of absorption and oral bioavailability of two controlled release ODT preparations of mixed amphetamine polistirex (equivalent to 30 mg mixed amphetamines) to an equivalent 30 mg oral dose of the commercially available reference product, ADDERALL XR, (Shire US Inc.) following an overnight fast of at least 10 hours. Subjects were randomly assigned to a treatment sequence and received three, separate single-dose administrations of study medication, one treatment per period, according to the randomization schedule. Dosing days were separated by a washout period of at least 7 days.

Subjects received each of the treatments listed below during the three treatment periods:

Treatment A: Test Formulation #1 (mixed amphetamine resins) controlled-release ODT. Test Formulation #1 is substantially similar to Formula C in Example 6. Dose=1×mixed amphetamine polistirex ODT equivalent to 30 mg mixed amphetamine salts.

Treatment B: Test Formulation #2 (mixed amphetamine resins) controlled-release ODT. Test Formulation #2 is substantially similar to Formula C in Example 6. Dose=1×mixed amphetamine polistirex ODT equivalent to 30 mg mixed amphetamine salts Treatment C: Reference Product ADDERALL XR Shire US, Inc. Dose=1×30 mg capsule Clinical Procedures Summary During each study period, 4 mL blood samples were obtained prior to each dosing and following each dose at selected times through 60 hours post-dose. A total of 60 pharmacokinetic blood samples were collected from each subject, 20 samples in each study period. In addition, blood was drawn and urine was collected for clinical laboratory testing at screening and study exit.

In each study period, subjects were admitted to the study unit in the evening prior to the scheduled dose. Subjects were confined to the research center during each study period until completion of the 36-hour blood collection and other study procedures. Subjects returned to the study unit for outpatient pharmacokinetic blood samples at 48 and 60 hours. Thirty-three (33) of the 36 subjects enrolled completed the study.

Procedures for Collecting Samples for Pharmacokinetic Analysis

Blood samples (1×4 mL) were collected in vacutainer tubes containing $K_2$-EDTA as a preservative at pre-dose (0) and at 1.0, 2.0, 3.0, 4.0, 5.0, 5.5, 6.0, 6.5, 7.0, 7.5, 8.0, 9.0, 10.0, 12.0, 16.0, 24.0, 36.0, 48.0, and 60.0 hours after dosing.

Bioanalytical Summary

Plasma samples were analyzed for d-amphetamine and l-amphetamine by a third party laboratory using a validated LC MS MS procedure. The method was validated for a range of 0.500 to 80.0 ng/mL for d-amphetamine and 0.200 to 32.0 ng/mL for l-amphetamine, based on the analysis of 0.150 mL of human EDTA plasma.

Pharmacokinetic Analysis

Concentration time data were analyzed by noncompartmental methods in WinNonlin. Concentration time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Full precision concentration data (not rounded to three significant figures) and actual sample times were used for all pharmacokinetic and statistical analyses.

The following pharmacokinetic parameters were calculated: peak concentration in plasma ($C_{max}$), time to peak concentration ($T_{max}$), elimination rate constant ($\lambda z$), terminal half-life (T½), area under the concentration-time curve from time-zero to the time of the last quantifiable concentration ($AUC_{last}$), and area under the plasma concentration time curve from time-zero extrapolated to infinity ($AUC_{inf}$). Secondary pharmacokinetic endpoints included partial AUCs.

The following partial AUCs were calculated using the linear trapezoidal method: $AUC_{0-4}$, $AUC_{4-12}$, and $AUC_{0-24}$.

Analysis of variance (ANOVA) and the Schuirmann's two one sided t test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals of the log-transformed parameters were within 80% to 125%. Comparisons of partial $AUC_{0-4}$, $AUC_{4-12}$, and $AUC_{0-24}$ across treatments were performed as supportive evidence of equivalence.

Results

Data from 33 subjects who completed the study were included in the pharmacokinetic and statistical analyses. Mean concentration-time data are shown in FIGS. 14 and 15. Results of the pharmacokinetic and statistical analyses are shown below in Tables 8 through 11.

The results show that the d- and l-amphetamine enantiomers of Test Formulations #1 and #2 were bioequivalent to the Reference Product. In particular, nearly all of the partial AUCs ($AUC_{4-12}$ and $AUC_{0-24}$) of the d- and l-amphetamine enantiomers of Test Formulations #1 and #2 were bioequivalent to the Reference Product.

Figure 14A:
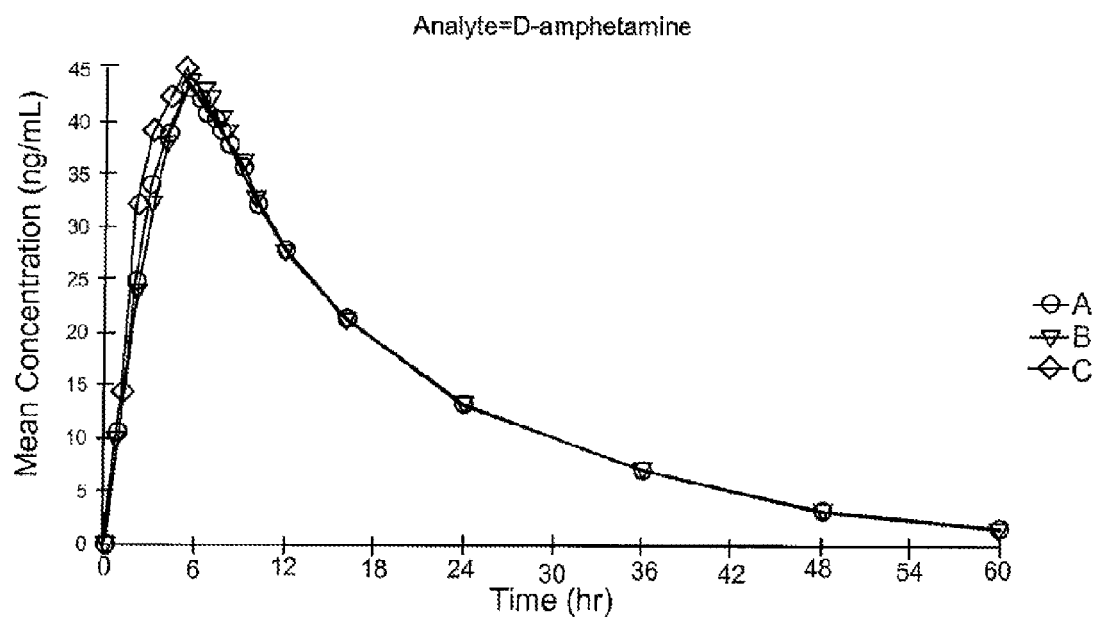
FIGS. 14A and 14B show the mean d-amphetamine concentration-time profiles after administration of Test Formulation #1 (Treatment A), Test Formulation #2 (Treatment B), and Reference Product (Treatment C), as described in Example 15.
Figure 14B:
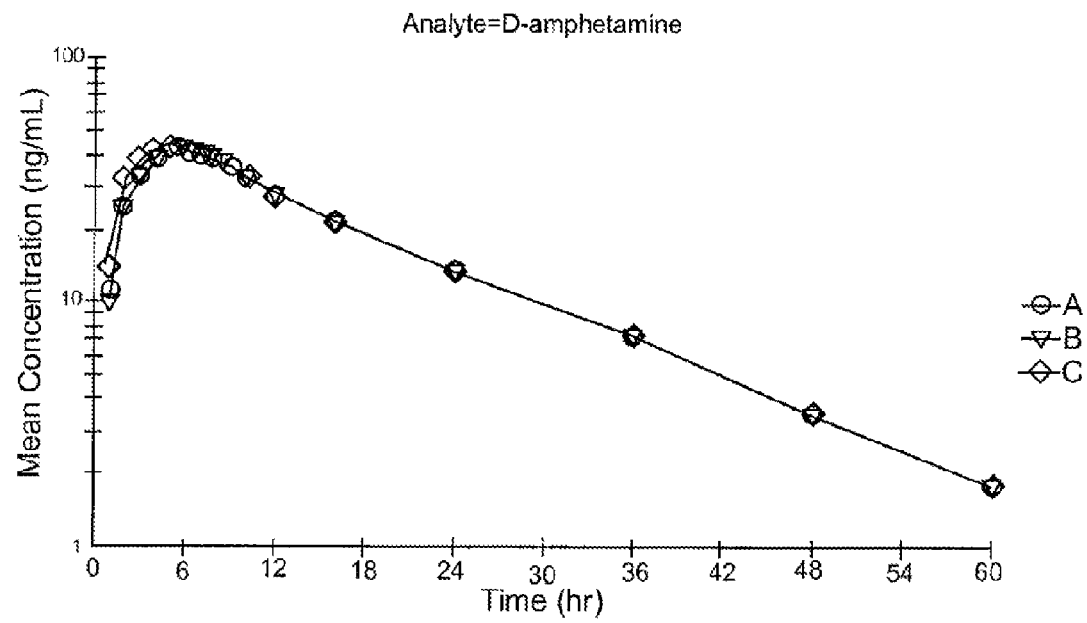

FIGS. 14A and 14B show the mean d-amphetamine concentration-time profiles after administration of Test Formulation #1 (Treatment A), Test Formulation #2 (Treatment B), and Reference Product (Treatment C).

Figure 15A:
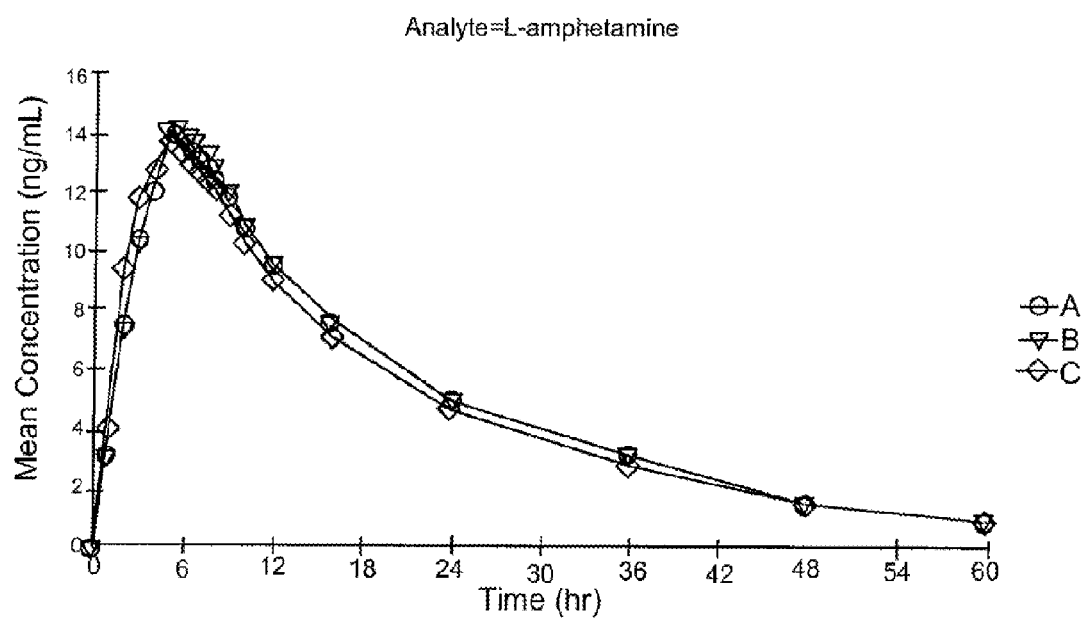
FIGS. 15A and 15B show the mean l-amphetamine concentration-time profiles after administration of test formulation #1 (Treatment A), test formulation #2 (Treatment B), and reference product (Treatment C), as described in Example 15.
Figure 15B:
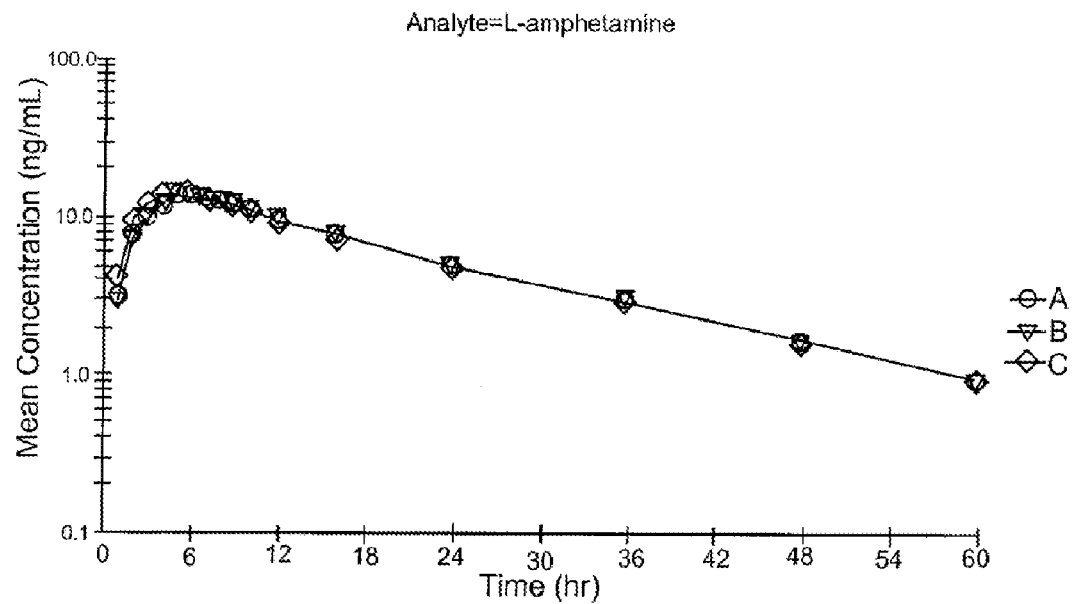
Figure 16:
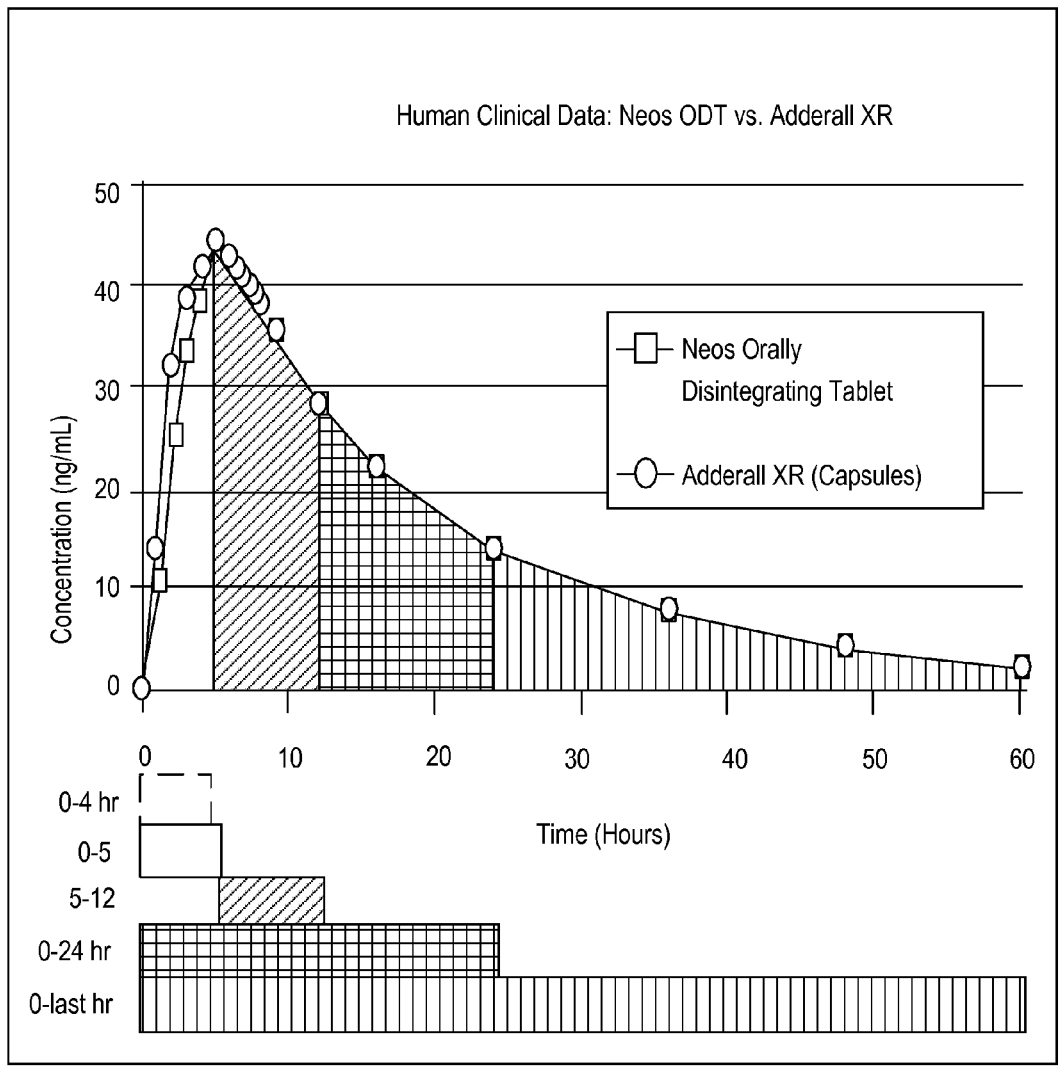
FIG. 16 shows the mean d-amphetamine concentration-time profiles after administration of the ODT formulation and Reference Product (ADDERALL XR), as described in Example 16.
Figure 17:
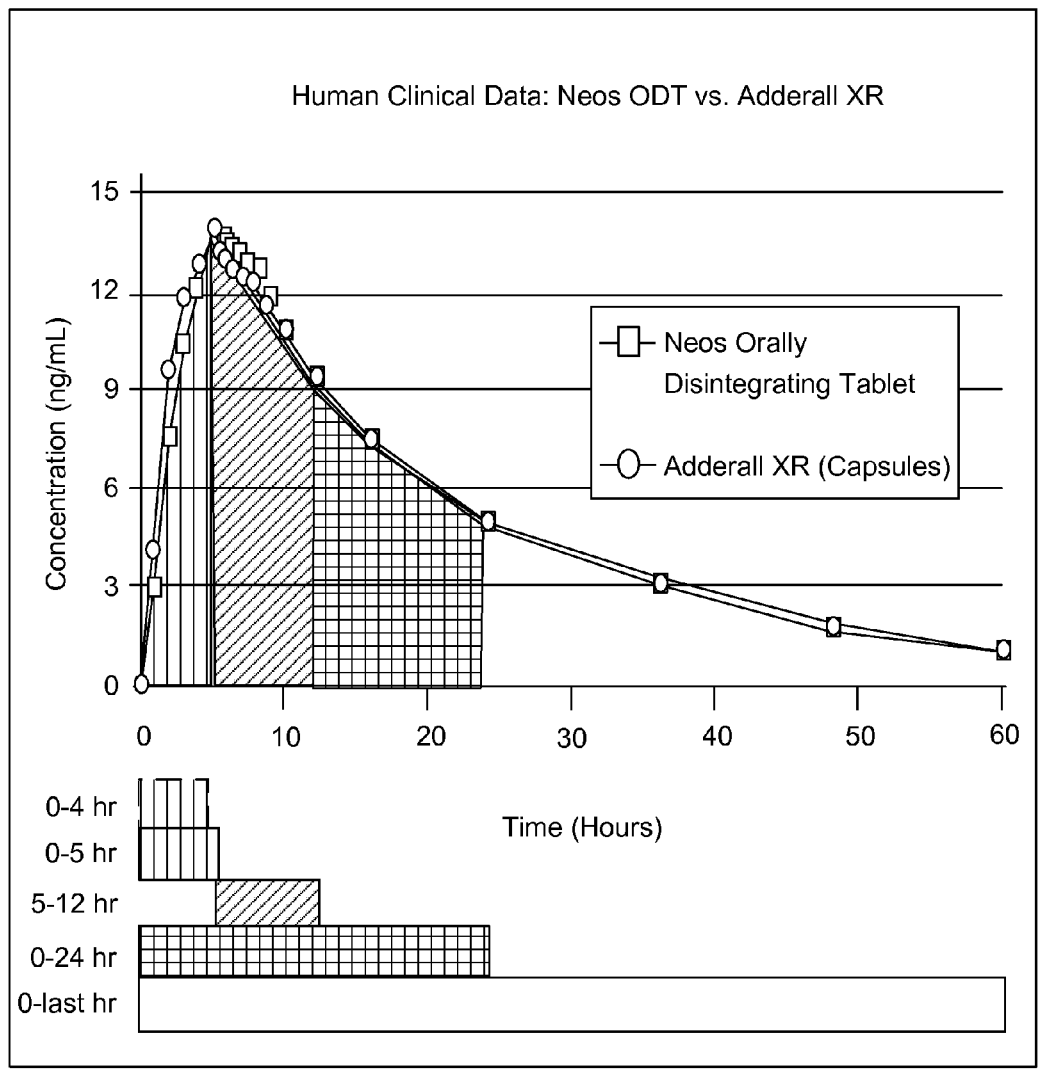
FIG. 17 shows the mean l-amphetamine concentration-time profiles after administration of the ODT formulation and Reference Product (ADDERALL XR), as described in Example 16.
Figure 18:
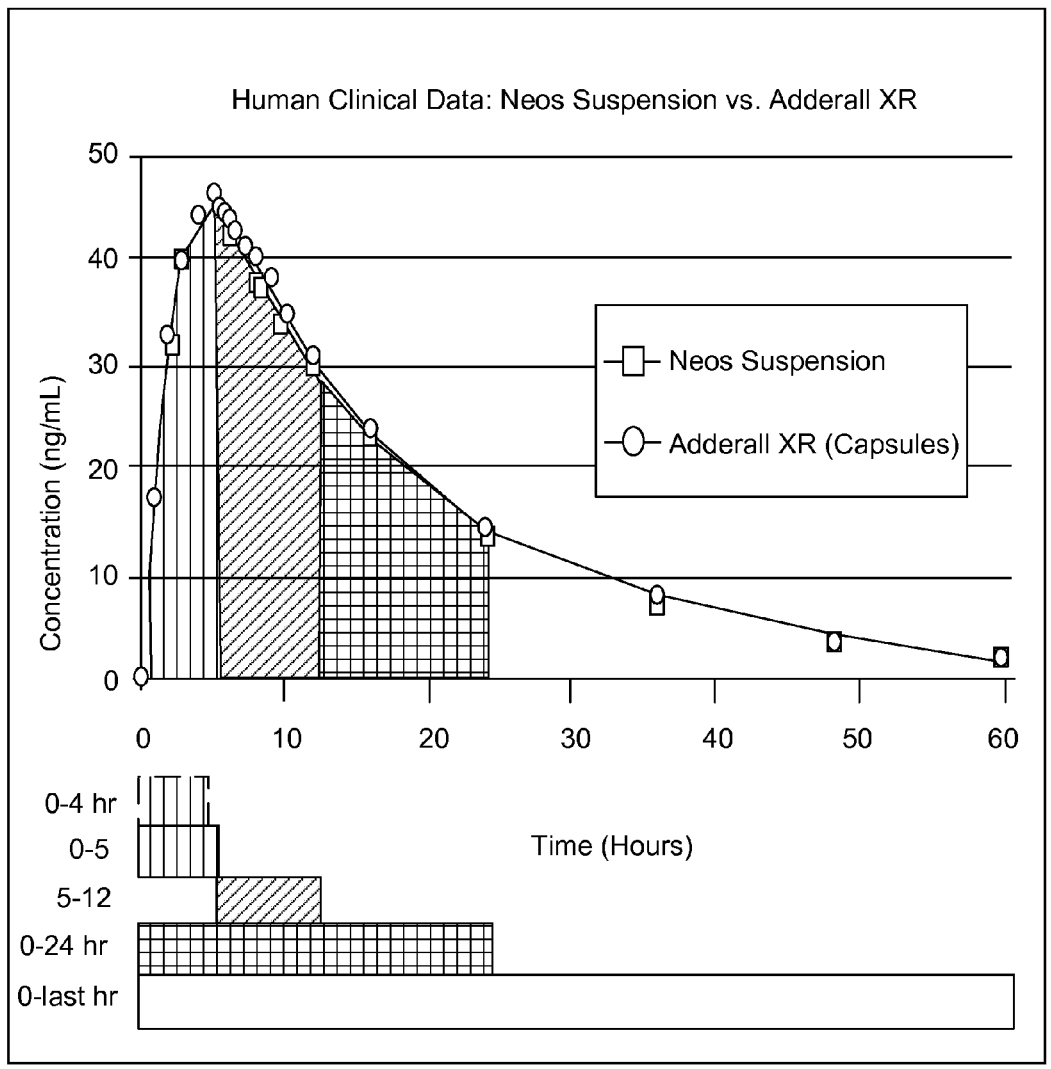
FIG. 18 shows the mean d-amphetamine concentration-time profiles after administration of the suspension formulation and Reference Product (ADDERALL XR), as described in Example 16.
Figure 19:
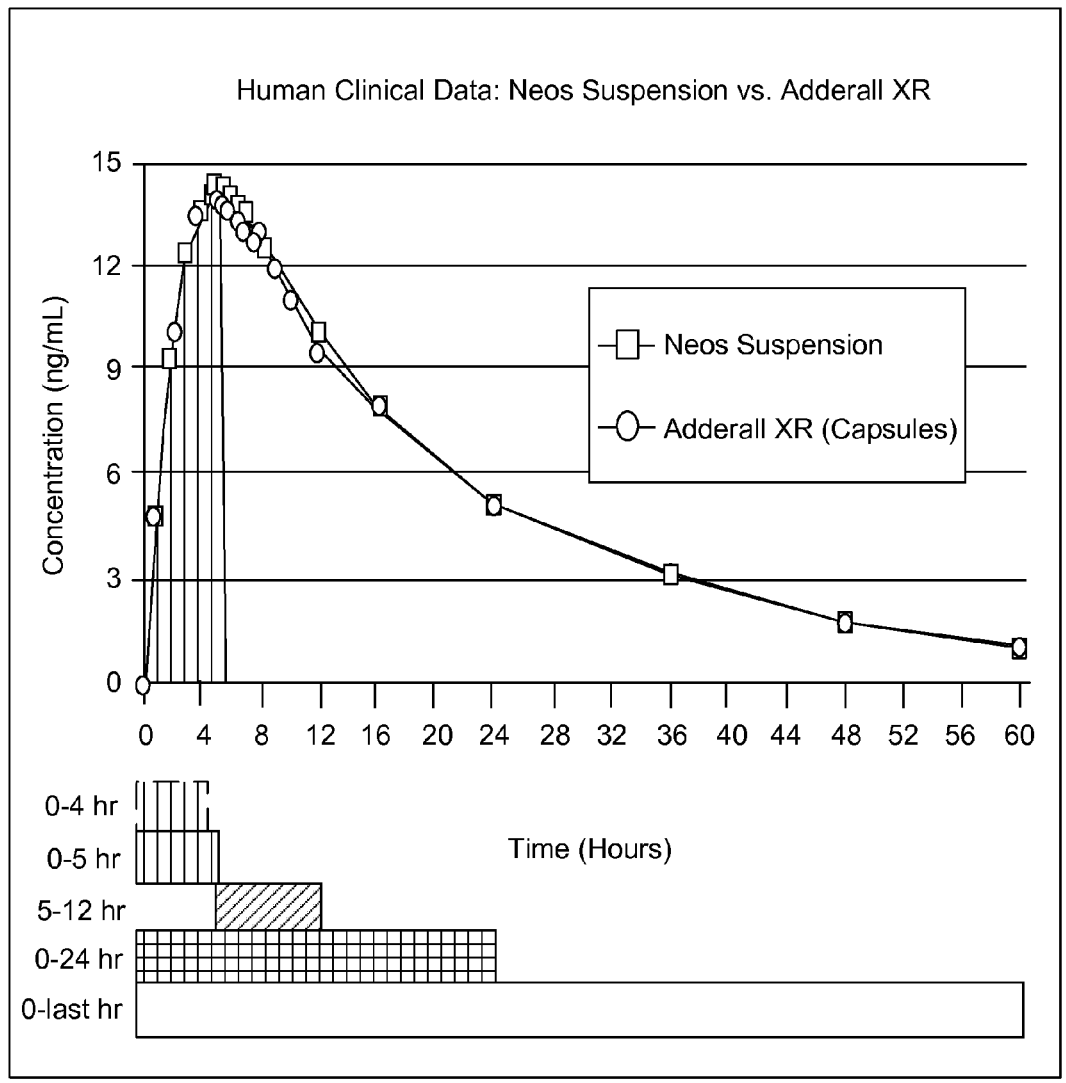
FIG. 19 shows the mean l-amphetamine concentration-time profiles after administration of the suspension formulation and Reference Product (ADDERALL XR), as described in Example 16.

FIGS. 15A and 15B show the mean l-amphetamine concentration-time profiles after administration of test formulation #1 (Treatment A), test formulation #2 (Treatment B), and reference product (Treatment C).

TABLE 8

Statistical analysis of the log-transformed systemic exposure parameters of d-amphetamine comparing Test Formulation #1 (Treatment A) to the Reference Product (Treatment C).

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 44.5370 | 45.9975 | 96.82 | 94.62 | 99.08 | 1.0000 | 5.61 |
| $\ln(AUC_{0-4})$ | 85.9326 | 100.9418 | 85.13 | 78.30 | 92.56 | 0.9965 | 20.54 |
| $\ln(AUC_{4-12})$ | 290.8805 | 294.3597 | 98.82 | 96.85 | 100.82 | 1.0000 | 4.89 |
| $\ln(AUC_{0-24})$ | 613.2608 | 631.8461 | 97.06 | 94.84 | 99.32 | 1.0000 | 5.61 |
| $\ln(AUC_{last})$ | 825.7531 | 843.4700 | 97.90 | 94.99 | 100.90 | 1.0000 | 7.34 |
| $\ln(AUC_{inf})$ | 848.3149 | 866.4947 | 97.90 | 94.73 | 101.18 | 1.0000 | 7.88 |

[a]Geometric Mean for the Test Formulation #1 (Test) and Reference Product (Ref) based on Least Squares Mean of log-transformed parameter values
[b]Ratio (%) = Geometric Mean (Test)/Geometric Mean (Ref)
[c]90% Confidence Interval Note:

$T_{1/2}$ and parameters based on extrapolation could not be calculated for all subjects; statistical analysis is based on n = 33 for $C_{max}$, $AUC_{0-4}$, $AUC_{4-12}$, $AUC_{0-24}$, $AUC_{last}$ and n = 32 for $AUC_{inf}$

TABLE 9

Statistical analysis of the log-transformed systemic exposure parameters of d-amphetamine comparing Test Formulation #2 (Treatment B) to the Reference Product (Treatment C).

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 45.2664 | 45.9975 | 98.41 | 96.17 | 100.70 | 1.0000 | 5.61 |
| $\ln(AUC_{0-4})$ | 80.8609 | 100.9418 | 80.11 | 73.68 | 87.09 | 0.9965 | 20.54 |
| $\ln(AUC_{4-12})$ | 295.5819 | 294.3597 | 100.42 | 98.42 | 102.45 | 1.0000 | 4.89 |
| $\ln(AUC_{0-24})$ | 616.5054 | 631.8461 | 97.57 | 95.35 | 99.85 | 1.0000 | 5.61 |

TABLE 9-continued

Statistical analysis of the log-transformed systemic exposure parameters of d-amphetamine comparing Test Formulation #2 (Treatment B) to the Reference Product (Treatment C).

| Dependent Variable | Geometric Mean[a] Test | Ref | Ratio (%)[b] (Test/Ref) | 90% CI[c] Lower | Upper | Power | ANOVA CV % |
|---|---|---|---|---|---|---|---|
| ln(AUC$_{last}$) | 830.7075 | 843.4700 | 98.49 | 95.56 | 101.50 | 1.0000 | 7.34 |
| ln(AUC$_{inf}$) | 851.1774 | 866.4947 | 98.23 | 95.05 | 101.52 | 1.0000 | 7.88 |

[a]Geometric Mean for the Test Formulation #2 (Test) and Reference Product (Ref) based on Least Squares Mean of log-transformed parameter values
[b]Ratio (%) = Geometric Mean (Test)/Geometric Mean (Ref)
[c]90% Confidence Interval Note:
$T_{1/2}$ and parameters based on extrapolation could not be calculated for all subjects; statistical analysis is based on n = 33 for $C_{max}$, $AUC_{0-4}$, $AUC_{4-12}$, $AUC_{0-24}$, $AUC_{last}$, and n = 32 for $AUC_{inf}$

TABLE 10

Statistical analysis of the log-transformed systemic exposure parameters of l-amphetamine comparing Test Formulation #1 (Treatment A) to the Reference Product (Treatment C).

| Dependent Variable | Geometric Mean[a] Test | Ref | Ratio (%)[b] (Test/Ref) | 90% CI[c] Lower | Upper | Power | ANOVA CV % |
|---|---|---|---|---|---|---|---|
| ln(C$_{max}$) | 14.2494 | 14.1857 | 100.45 | 98.07 | 102.89 | 1.0000 | 5.85 |
| ln(AUC$_{0-4}$) | 26.3537 | 30.0286 | 87.76 | 80.53 | 95.64 | 0.9951 | 21.14 |
| ln(AUC$_{4-12}$) | 95.1124 | 93.0132 | 102.26 | 100.09 | 104.47 | 1.0000 | 5.20 |
| ln(AUC$_{0-24}$) | 204.9113 | 203.7331 | 100.58 | 98.07 | 103.15 | 1.0000 | 6.14 |
| ln(AUC$_{last}$) | 295.5590 | 290.6272 | 101.70 | 98.33 | 105.18 | 1.0000 | 8.21 |
| ln(AUC$_{inf}$) | 312.0976 | 307.0441 | 101.65 | 97.80 | 105.64 | 1.0000 | 9.24 |

[a]Geometric Mean for the Test Formulation #1 (Test) and Reference Product (Ref) based on Least Squares Mean of log-transformed parameter values
[b]Ratio (%) = Geometric Mean (Test)/Geometric Mean (Ref)
[c]90% Confidence Interval Note:
$T_{1/2}$ and parameters based on extrapolation could not be calculated for all subjects; statistical analysis is based on n = 33 for $C_{max}$, $AUC_{0-4}$, $AUC_{4-12}$, $AUC_{0-24}$, $AUC_{last}$, and n = 32 for $AUC_{inf}$

TABLE 11

Statistical analysis of the log-transformed systemic exposure parameters of l-amphetamine comparing Test Formulation #2 (Treatment B) to the Reference Product (Treatment C).

| Dependent Variable | Geometric Mean[a] Test | Ref | Ratio (%)[b] (Test/Ref) | 90% CI[c] Lower | Upper | Power | ANOVA CV % |
|---|---|---|---|---|---|---|---|
| ln(C$_{max}$) | 14.6051 | 14.1857 | 102.96 | 100.51 | 105.46 | 1.0000 | 5.85 |
| ln(AUC$_{0-4}$) | 24.9270 | 30.0286 | 83.01 | 76.17 | 90.46 | 0.9951 | 21.14 |
| ln(AUC$_{4-12}$) | 96.8135 | 93.0132 | 104.09 | 101.88 | 106.34 | 1.0000 | 5.20 |
| ln(AUC$_{0-24}$) | 206.6684 | 203.7331 | 101.44 | 98.91 | 104.03 | 1.0000 | 6.14 |
| ln(AUC$_{last}$) | 297.5544 | 290.6272 | 102.38 | 98.99 | 105.89 | 1.0000 | 8.21 |
| ln(AUC$_{inf}$) | 313.3883 | 307.0441 | 102.07 | 98.21 | 106.07 | 1.0000 | 9.24 |

[a]Geometric Mean for the Test Formulation #2 (Test) and Reference Product (Ref) based on Least Squares Mean of log-transformed parameter values
[b]Ratio(%) = Geometric Mean (Test)/Geometric Mean (Ref)
[c]90% Confidence Interval Note:
$T_{1/2}$ and parameters based on extrapolation could not be calculated for all subjects; statistical analysis is based on n = 33 for $C_{max}$, $AUC_{0-4}$, $AUC_{4-12}$, $AUC_{0-24}$, $AUC_{last}$, and n = 32 for $AUC_{inf}$ Example 16

Human Pharmacokinetic Study Comparing ODT to Suspension Formulations

This example compared the rate of absorption and oral bioavailability of a controlled release ODT preparation of mixed amphetamine polistirex (equivalent to 30 mg mixed amphetamine salts) and a controlled release liquid suspension of mixed amphetamine polistirex (equivalent to 30 mg mixed amphetamine salts) to an equivalent 30 mg oral dose of the commercially available reference product, ADDERALL XR (Shire US Inc.) following an overnight fast of at least 10 hours. Subjects were randomly assigned to a treatment sequence and received three separate single-dose administrations of study medication, one treatment per period, according to the randomization schedule as described in the previous Example. Dosing days were separated by a washout period of at least 7 days.

Subjects received each of the treatments listed below during the three treatment periods:

Treatment A: Test Formulation #3 (mixed amphetamine resins) controlled-release ODT. Dose=1×mixed amphetamine polistirex ODT equivalent to 30 mg mixed amphetamine salts.

Treatment B: Test Formulation #4 (mixed amphetamine resins) controlled-release suspension. Dose=1×mixed amphetamine polistirex suspension equivalent to 30 mg mixed amphetamine salts.

Treatment C: Reference Product ADDERALL XR, Shire US, Inc. Dose=1×30 mg capsule.

TABLE 12

Test Formulation #3 (ODT amphetamine with 45% IR and 55% DR)
IR Resin - 34.08% base assay & DR Resin - 7.28% base assay: These values will be variable

| | Formula #3 (45% active from IR Resin & 55% active from DR Resin) | | |
|---|---|---|---|
| | mg/dose | Notes | % |
| Uncoated (IR) AMP Resin | 24.82 | | 3.76 |
| Amphetamine (base) | 4.23 | | |
| Dextroamphetamine (base) | 4.23 | | |
| AMBERLITE IRP069 Resin | 13.88 | | |
| Polyethylene Glycol | 1.24 | | |
| Purified Water | 1.24 | | |
| Coated (DR) AMP Resin | 142.03 | | 21.52 |
| Amphetamine (base) | 5.17 | | |
| Dextroamphetamine (base) | 5.17 | | |
| AMBERLITE IRP069 Resin | 16.96 | | |
| Polyethylene Glycol | 1.52 | | |
| Purified Water | 1.52 | | |
| EUDRAGIT L100 | 97.21 | | |
| Triethyl Citrate | 14.48 | | |
| Prosolv ODT | 323.20 | | 48.97 |
| Crospovidone | 105.60 | | 16.00 |
| Flavorings | 65.35 | | 9.75 |
| Total | 660.00 mg | | 100% |

TABLE 13

Test Formulation #4 (Suspension amphetamine with 45% IR and 55% DR)
IR Resin - 34.08% base assay & DR Resin - 7.28% base assay:

| | Formula #4 (45% active from IR Resin & 55% active from DR Resin) | | |
|---|---|---|---|
| | mg per 15 mL dose | Notes | % |
| Uncoated (IR) AMP Resin | 24.82 | | 0.14 |
| Amphetamine (base) | 4.23 | | |
| Dextroamphetamine (base) | 4.23 | | |
| AMBERLITE IRP069 Resin | 13.88 | | |
| Polyethylene Glycol | 1.24 | | |
| Purified Water | 1.24 | | |
| Coated (DR) AMP Resin | 142.03 | | 0.79 |
| Amphetamine (base) | 5.17 | | |
| Dextroamphetamine (base) | 5.17 | | |
| AMBERLITE IRP069 Resin | 16.96 | | |
| Polyethylene Glycol | 1.52 | | |
| Purified Water | 1.52 | | |
| EUDRAGIT L100 | 97.21 | | |
| Triethyl Citrate | 14.48 | | |
| Purified Water | 8123.2 | Each 15 mL dose of suspension is | 45.13 |
| Ascorbic Acid | 6.00 | equivalent to 18 grams at the | 0.03 |
| Propylene Glycol | 525.00 | theoretical suspension specific | 2.92 |
| Preservative | 3.75 | gravity of 1.2. | 0.03 |
| Polysorbate 80 | 15.00 | | 0.08 |
| Xanthan Gum | 90.00 | | 0.50 |
| Vegetable Oil | 30.00 | | 0.17 |
| Color & Flavor | 40.20 | | <0.23 |
| Sucrose | 2250.00 | | 12.50 |
| High Fructose Corn Syrup | 6750.00 | | 37.50 |
| Total | 18,000.00 mg | | 100% |

Administration, data collection and analysis were carried out as described in the previous Example. Data from subjects who completed the study were included in the pharmacokinetic and statistical analyses. Mean concentration-time data are shown in FIGS. 16-19. Results of the pharmacokinetic and statistical analyses are shown below in Tables 14 through 17.

TABLE 14

Statistical Analysis of Human Bioequivalence Studies: ODT Data (D-Isomer)

| | Mean | | Ratio(%) | 90% CI | |
|---|---|---|---|---|---|
| Dependent Variable | Test | Ref | (Test/Ref) | Lower | Upper |
| $\ln(C_{max})$ | 44.5 | 46.0 | 96.7 | 94.6 | 99.1 |
| $\ln(AUC_{0-4})$ | 85.9 | 100.9 | 85.1 | 78.3 | 92.6 |
| $\ln(AUC_{0-5})$ | 126.3 | 46.0 (?) | 87.7 | 82.1 | 93.7 |
| $\ln(AUC_{4-12})$ | 290.9 | 294.4 | 98.8 | 96.9 | 100.8 |
| $\ln(AUC_{5-12})$ | 250.5 | 251.6 | 99.5 | 97.3 | 101.8 |
| $\ln(AUC_{0-24})$ | 613.3 | 631.8 | 97.1 | 94.8 | 99.3 |
| $\ln(AUC_{last})$ | 825.8 | 843.5 | 97.9 | 95.0 | 100.9 |
| $\ln(AUC_{inf})$ | 848.3 | 866.5 | 97.9 | 94.7 | 101.2 |
| $T_{max}$ | 5.26 | 4.53 | | | |

TABLE 15

Statistical Analysis of Human Bioequivalence Studies: ODT Data (L-Isomer)

| | Mean | | Ratio (%) | 90% CI | |
|---|---|---|---|---|---|
| Dependent Variable | Test | Ref | (Test/Ref) | Lower | Upper |
| $\ln(C_{max})$ | 14.2 | 14.2 | 100.5 | 98.1 | 102.9 |
| $\ln(AUC_{0-4})$ | 26.4 | 30.0 | 87.8 | 80.5 | 95.6 |
| $\ln(AUC_{0-5})$ | 39.2 | 43.2 | 90.7 | 84.6 | 97.1 |
| $\ln(AUC_{4-12})$ | 95.1 | 93.0 | 102.3 | 100.1 | 104.5 |
| $\ln(AUC_{5-12})$ | 82.3 | 79.9 | 103.0 | 100.5 | 105.5 |
| $\ln(AUC_{0-24})$ | 204.9 | 203.7 | 100.6 | 98.1 | 103.2 |
| $\ln(AUC_{last})$ | 295.6 | 290.6 | 101.7 | 98.3 | 105.2 |
| $\ln(AUC_{inf})$ | 312.1 | 307.0 | 101.7 | 97.8 | 105.6 |
| $T_{max}$ | 5.70 | 4.59 | | | |

TABLE 16

Statistical Analysis of Human Bioequivalence Studies: Suspension Data (D-Isomer)

| | Mean | | Ratio (%) | 90% CI | |
|---|---|---|---|---|---|
| Dependent Variable | Test | Ref | (Test/Ref) | Lower | Upper |
| $\ln(C_{max})$ | 46.3 | 49.1 | 94.2 | 91.4 | 97.0 |
| $\ln(AUC_{0-4})$ | 104.7 | 107.4 | 97.5 | 88.7 | 107.0 |
| $\ln(AUC_{0-5})$ | 148.6 | 152.4 | 97.5 | 90.7 | 104.9 |
| $\ln(AUC_{4-12})$ | 300.4 | 313.8 | 95.7 | 92.7 | 98.9 |
| $\ln(AUC_{5-12})$ | 256.9 | 269.1 | 95.5 | 92.1 | 98.9 |
| $\ln(AUC_{0-24})$ | 651.8 | 680.2 | 95.8 | 92.6 | 99.2 |
| $\ln(AUC_{last})$ | 861.2 | 904.5 | 95.2 | 91.0 | 99.6 |
| $\ln(AUC_{inf})$ | 892.8 | 935.4 | 95.4 | 91.0 | 100.1 |
| $T_{max}$ | 4.61 | 4.96 | | | |

TABLE 17

Statistical Analysis of Human Bioequivalence Studies: Suspension Data (L-Isomer)

| | Mean | | Ratio (%) | 90% CI | |
|---|---|---|---|---|---|
| Dependent Variable | Test | Ref | (Test/Ref) | Lower | Upper |
| $\ln(C_{max})$ | 14.6 | 14.8 | 98.9 | 96.3 | 101.6 |
| $\ln(AUC_{0-4})$ | 31.8 | 31.6 | 100.8 | 91.6 | 110.8 |
| $\ln(AUC_{0-5})$ | 45.7 | 45.2 | 101.1 | 93.8 | 108.9 |
| $\ln(AUC_{4-12})$ | 96.8 | 97.1 | 99.7 | 96.4 | 103.2 |
| $\ln(AUC_{5-12})$ | 83.2 | 83.6 | 99.5 | 95.9 | 103.2 |
| $\ln(AUC_{0-24})$ | 215.2 | 215.5 | 99.9 | 96.3 | 103.6 |
| $\ln(AUC_{last})$ | 304.8 | 306.8 | 99.3 | 94.6 | 104.4 |
| $\ln(AUC_{inf})$ | 325.3 | 327.0 | 99.5 | 94.0 | 105.2 |
| $T_{max}$ | 5.09 | 5.27 | | | |

Example 17

Orally Disintegrating Tablet with 25% IR and 75% ER/DR

An orally disintegrating tablet was formulated with 25% of methylphenidate from immediate release resin complex and 75% of the methylphenidate from an extended release (ER)/delayed release (DR) resin complex. In the ER/DR coating, ethylcellulose overlays EUDRAGIT. The formula is presented below.

TABLE 18

ODT methylphenidate Formulation A with 25% IR and 75% ER/DR.
IR Resin—36.98% base assay & ER/DR Resin—13.11% base assay: These values are variable

| | Formula A (25% active from IR Resin & 75% active from ER/DR Resin) | | |
|---|---|---|---|
| | mg/dose | Notes | % |
| Uncoated (IR) MPH Resin | 17.65 | The 17.65 mg/dose quantity is the actual amount of IR resin (at a 36.98% assay value) that goes into each tablet. The values in the gray area are the quantities of each material that compromise the IR material. | 2.67 |
| Methylphenidate (base) | 6.525 | | |
| AMBERLITE IRP069 Resin | 10.24 | | |
| Polyethylene Glycol | 0.441 | | |
| Purified Water | 0.441 | | |
| Coated (ER/DR) MPH Resin | 149.37 | The 149.37 mg/dose quantity is the actual amount of ER/DR resin (at a 13.11% assay value) that goes into each tablet The IR resin material was used to make the 149.37 mg/dose ER/DR material. The values in the gray area are the quantities of each material that compromise the ER/DR material. | 22.63 |
| Methylphenidate (base) | 19.575 | | |
| AMBERLITE IRP069 Resin | 30.72 | | |
| Polyethylene Glycol | 1.32 | | |
| Purified Water | 1.32 | | |
| Ethylcellulose N-10 | 11.505 | | |
| EUDRAGIT L100 | 73.37 | | |
| Triethyl Citrate | 11.56 | | |
| Prosolv ODT | 369.83 | The Prosolv ODT quantity will be variable to account for the variable assay value of the IR and DR resin. | 56.03 |
| Crospovidone | 66.00 | | 10.00 |
| Sucralose Powder | 23.00 | | 3.48 |
| Citric Acid | 10.00 | | 1.52 |
| Flavor & Color | 17.55 | | 2.66 |
| Magnesium Stearate | 6.60 | | 1.00 |
| Total | 660.00 mg | | 100% |

TABLE 19

ODT methylphenidate Formulation B with 25% IR and 75% ER/DR.

| | Formula B (25% active from IR Resin & 75% active from ER/DR Resin) | | |
|---|---|---|---|
| | mg/dose | Notes | % |
| Uncoated (IR) MPH Resin | 17.65 | The 17.65 mg/dose quantity is the actual amount of IR resin (at a 36.98% assay value) that goes into each tablet. The values in the gray area are the quantities of each material that compromise the IR material. | 2.67 |
| Methylphenidate (base) | 6.525 | | |
| AMBERLITE IRP069 Resin | 10.24 | | |
| Polyethylene Glycol | 0.441 | | |
| Purified Water | 0.441 | | |
| Coated (ER/DR) MPH Resin | 153.32 | The 153.32 mg/dose quantity is the actual amount of ER/DR resin (at a 12.77% assay value) that goes into each tablet. The IR resin material was used to make the 153.32 mg/dose ER/DR material. The values in the gray area are the quantities of each material that compromise the ER/DR material. | 23.23 |
| Methylphenidate (base) | 19.575 | | |
| AMBERLITE IRP069 Resin | 30.72 | | |
| Polyethylene Glycol | 1.32 | | |
| Purified Water | 1.32 | | |
| Ethylcellulose N-10 | 13.13 | | |
| EUDRAGIT L100 | 75.31 | | |
| Triethyl Citrate | 11.945 | | |
| Prosolv ODT | 365.88 | The Prosolv ODT quantity will be variable to account for the variable assay value of the IR and DR resin. | 55.44 |
| Crospovidone | 66.00 | | 10.00 |
| Sucralose Powder | 23.00 | | 3.48 |
| Citric Acid | 10.00 | | 1.52 |
| Flavor & Color | 17.55 | | 2.66 |
| Magnesium Stearate | 6.60 | | 1.00 |
| Total | 660.00 mg | | 100% |

IR Resin - 36.98% base assay & ER/DR Resin - 12.77% base assay: These values are variable.

These formulas are exactly the same except for the level of actual ethylcellulose coating (as determined by assay). Formula "A" has 18.6% ethylcellulose coating and "B" has 20.7%. These are the calculated coating levels of ethylcellulose prior to the EUDRAGIT coating.

Dissolution Method

Dissolution testing is carried out using an Apparatus 2 with cannulas and cannula filters (Quality Lab Accessories, Porus Micron full flow filters 20 micron); paddle speed—100 rpm; kettle size—1000 mL; temperature—37.0±0.5° C.; filter—25 mm 0.45 um PTFE; syringe—B-D10 mL Luer-Lok.

Dissolution Media:

The medium for the dissolution assay is 900 mL of 0.1N HCl for the first hour; after 2 hour time point~100 mL of potassium phosphate/sodium hydroxide solution is added to bring to pH~6.8.

The sample is weighed and is placed into the corresponding kettle, and the dissolution timing started.

Sampling pull times are 30 minutes, 2 hours, 4 hours and 8 hours. For each sample pull time and each kettle, 10 mL of sample are pulled into a B-D 10 mL Luer-Lok syringe and returned to the kettles before the sample pull to flush out the cannula from the prior pulls. 4 ml are then pulled for filtration, discarding the first 2 ml to waste and the remaining sample into an HPLC vial. Non-media replacement and volume changes from the two media changes are calculated.

Figure 26:
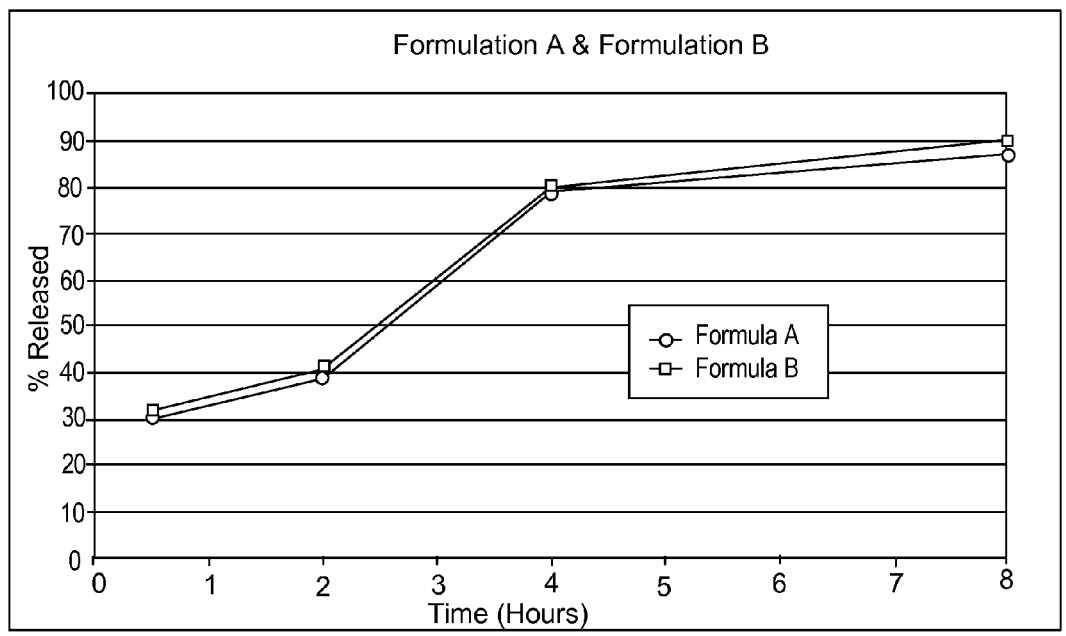
FIG. 26 shows the dissolution profile of compositions A and B described in Example 17.

Dissolution Profile:

The amount of drug in the filtrate at each time point is determined by HPLC, and the percentage released from Formulae A and B, respectively, are shown below and in FIG. 26.

| Formula A Profile | |
|---|---|
| Hours | Profile (% Release) |
| 0.5 | 31% |
| 2 | 39% |
| 4 | 79% |
| 8 | 87% |
| 24 | 87% |

| Formula B Profile | |
|---|---|
| Hours | Profile (% Release) |
| 0.5 | 32% |
| 2 | 41% |
| 4 | 80% |
| 8 | 90% |
| 24 | 90% |

Example 18

Human Pharmacokinetic Study Using ODT Pharmaceutical Compositions

This example describes a single-dose, open-label, randomized, three-period, three-treatment crossover study comparing the rate of absorption and oral bioavailability of two controlled release ODT preparations of methylphenidate polistirex (equivalent to 60 mg methylphenidate) to an equivalent 60 mg oral dose of the commercially available reference product, METADATE CD, (UCB, Inc.) following an overnight fast of at least 10 hours. Subjects were randomly assigned to a treatment sequence and received three, separate single-dose administrations of study medication, one treatment per period, according to the randomization schedule. Dosing days were separated by a washout period of at least 7 days.

Subjects received each of the treatments listed below during the three treatment periods:

Treatment A: Test Formulation #1 (methylphenidate resins) controlled-release ODT. Test Formulation #1 is substantially similar to the formulation A described in Example 17. Dose=2×methylphenidate polistirex ODT containing 26.1 mg methylphenidate base, equivalent to 60 mg methylphenidate HCl.

Treatment B: Test Formulation #2 (methylphenidate resins) controlled-release ODT. Test Formulation #2 is substantially similar to the formulation B described in Example 17. Dose=2×methylphenidate polistirex ODT containing 26.1 mg methylphenidate base, equivalent to 60 mg methylphenidate HCl.

Treatment C: Reference Product METADATE CD UCB, Inc. Dose=1×60 mg capsule

Clinical Procedures Summary

During each study period, 6 mL blood samples were obtained prior to each dosing and following each dose at selected times through 36 hours post-dose. A total of 63 pharmacokinetic blood samples were collected from each subject, 21 samples in each study period. In addition, blood was drawn and urine was collected for clinical laboratory testing at screening and study exit.

In each study period, subjects were admitted to the study unit in the evening prior to the scheduled dose. Subjects were confined to the research center during each study period until completion of the 24-hour blood collection and other study procedures. Subjects returned to the study unit for outpatient pharmacokinetic blood samples at 36 hours. Thirty-eight (38) of the 42 subjects enrolled completed the study.

Procedures for Collecting Samples for Pharmacokinetic Analysis

Blood samples (1×6 mL) were collected in vacutainer tubes containing $K_2$-EDTA as a preservative at pre-dose (0) and at 0.5, 1.0, 1.5, 2.0, 2.5, 3.0, 3.5, 4.0, 4.5, 5.0, 5.5, 6.0, 6.5, 7.0, 8.0, 10.0, 12.0, 18.0, 24.0, and 36.0 hours after dosing.

Bioanalytical Summary

Plasma samples were analyzed for d-methylphenidate and l-methylphenidate by a third party laboratory using a validated LC-MS-MS procedure. The method was validated for a range of 0.250 to 50.0 ng/mL for d-methylphenidate and 0.0100 to 2.00 ng/mL for l-methylphenidate, based on the analysis of 0.100 mL of human EDTA plasma.

Pharmacokinetic Analysis

Concentration time data were analyzed by noncompartmental methods in WinNonlin. Concentration time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Full precision concentration data (not rounded to three significant figures) and actual sample times were used for all pharmacokinetic and statistical analyses.

The following pharmacokinetic parameters were calculated for d-methylphenidate, l-methylphenidate, and total methylphenidate (d+l): peak concentration in plasma ($C_{max}$), time to peak concentration ($T_{max}$), elimination rate constant ($\lambda z$), terminal half-life ($T\frac{1}{2}$), area under the concentration-time curve from time-zero to the time of the last quantifiable concentration ($AUC_{last}$), and area under the plasma concentration time curve from time-zero extrapolated to infinity ($AUC_{inf}$). Secondary pharmacokinetic endpoints included partial AUCs. The following partial AUCs were calculated using the linear trapezoidal method: $AUC_{0-3}$, $AUC0\text{-}_{tmax}$ ($AUC_{0-5}$), $AUC_{tmax-24}$ ($AUC_{5-24}$), $AUC_{0-24}$, and $AUC_{tmax-tlast}$.

Test Formulations #1 and #2 were compared to the reference product. Analysis of variance (ANOVA) and the Schuirmann's two one sided t test procedures at the 5% significance level were applied to the log-transformed pharmacokinetic exposure parameters, $C_{max}$, $AUC_{last}$, and $AUC_{inf}$ d-methylphenidate, l-methylphenidate, and total methylphenidate (d+l). The 90% confidence interval for the ratio of the geometric means (Test/Reference) was calculated. Bioequivalence was declared if the lower and upper confidence intervals of the log-transformed parameters were within 80% to 125%. mComparisons of partial AUCs, $AUC_{0-3}$, $AUC0_{-tmax}$ ($AUC_{0-5}$), $AUC_{tmax-24}$ ($AUC_{5-24}$), $AUC_{0-24}$, and $AUC_{tmax-tlast}$ across treatments were performed as supportive evidence of equivalence.

Results

Data from 38 subjects who completed the study were included in the pharmacokinetic and statistical analyses.

Figure 20A:
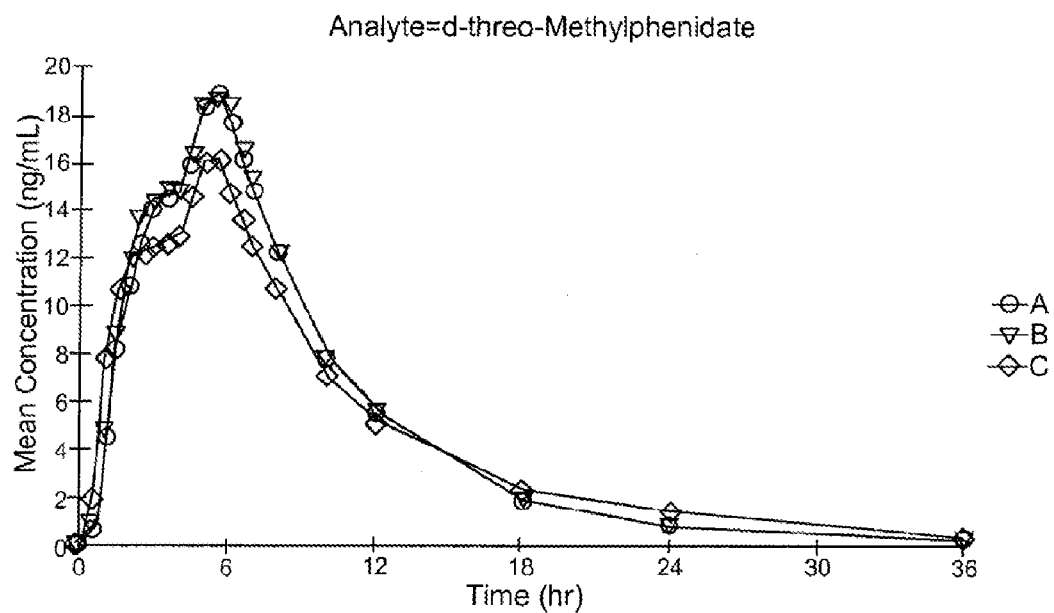
FIGS. 20A and 20B show the mean d-methylphenidate concentration-time profiles after administration of Test Formulation #1 (Treatment A), Test Formulation #2 (Treatment B), and Reference Product (Treatment C), as described in Example 18.
Figure 20B:
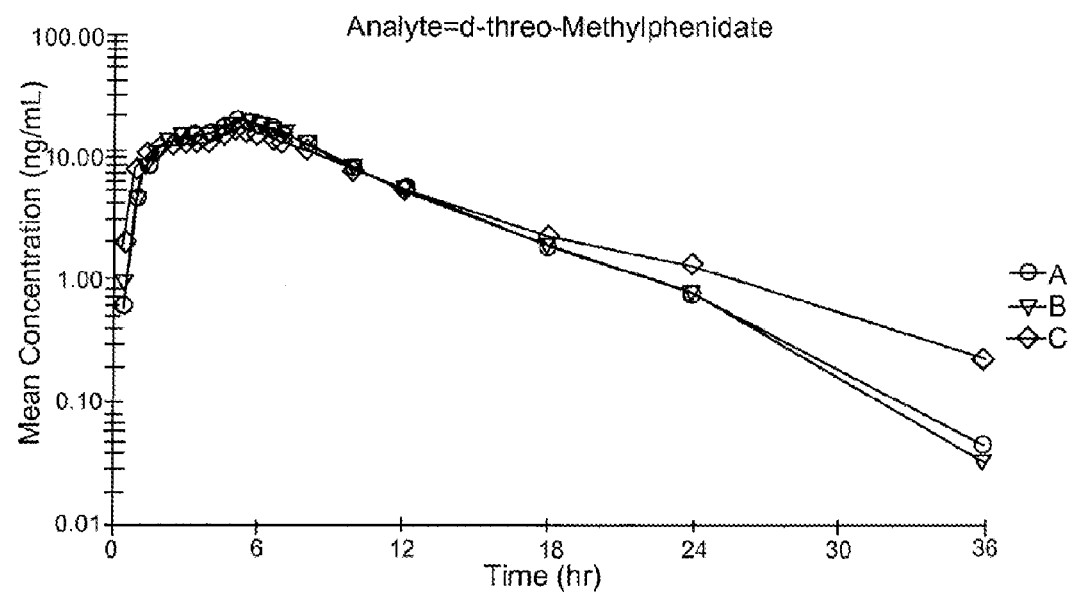

FIGS. 20A and 20B show the mean linear and log d-methylphenidate concentration-time profiles after administration of Test Formulation #1 (Treatment A), Test Formulation #2 (Treatment B), and Reference Product (Treatment C).

Figure 21A:
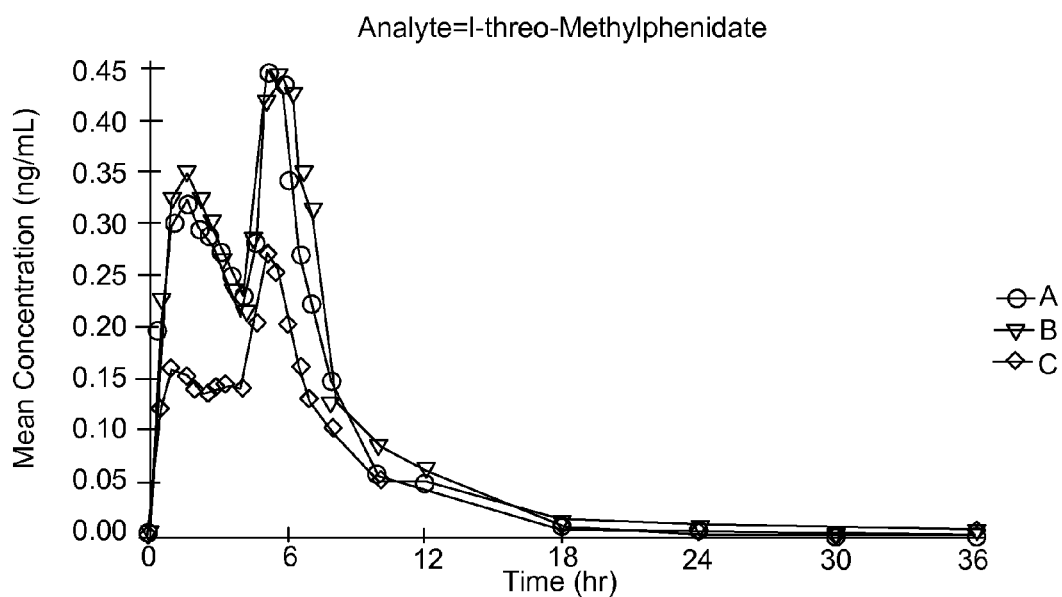
FIGS. 21A and 21B show the mean l-methylphenidate concentration-time profiles after administration of Test Formulation #1 (Treatment A), Test Formulation #2 (Treatment B), and Reference Product (Treatment C), as described in Example 18.
Figure 21B:
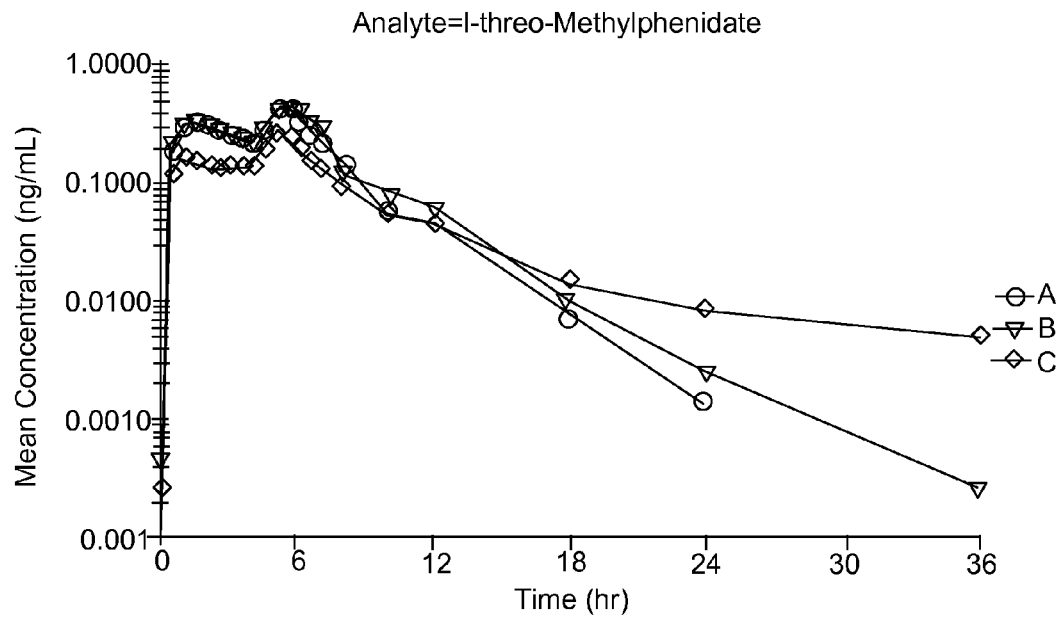

FIGS. 21A and 21B show the mean linear and log l-methylphenidate concentration-time profiles after administration of Test Formulation #1 (Treatment A), Test Formulation #2 (Treatment B), and Reference Product (Treatment C).

Figure 22A:
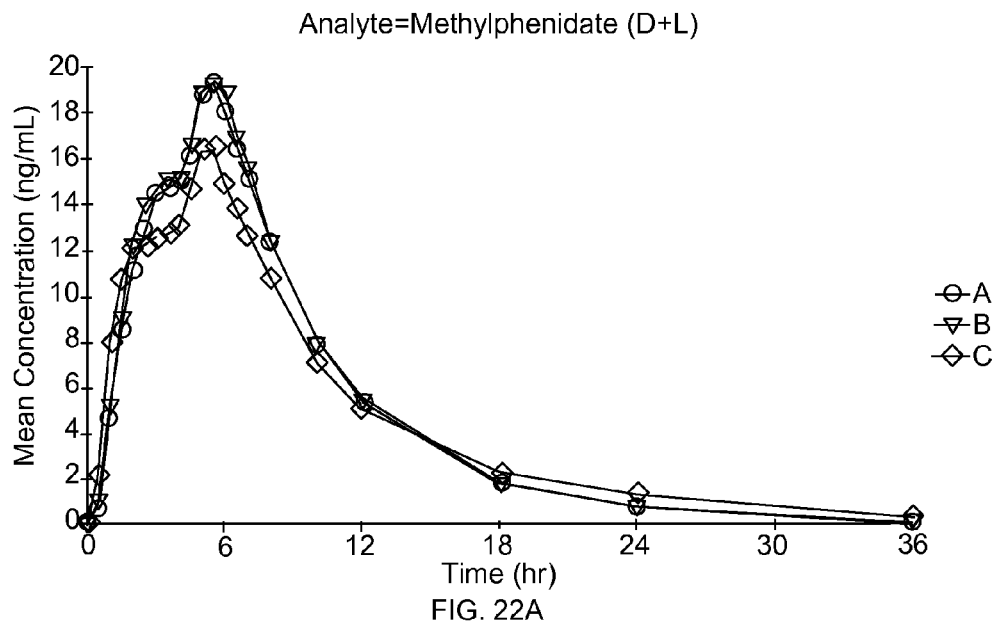
FIGS. 22A and 22B show the mean total methylphenidate (d+l) concentration-time profiles after administration of Test Formulation #1 (Treatment A), Test Formulation #2 (Treatment B), and Reference Product (Treatment C), as described in Example 18.
Figure 22B:
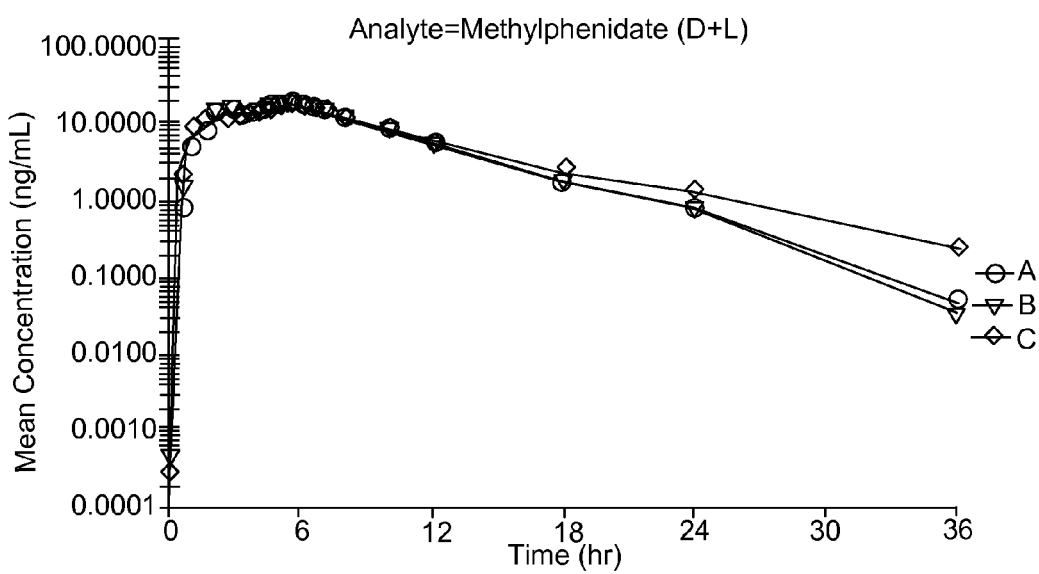

FIGS. 22A and 22B show the mean linear and log total methylphenidate (d+l) concentration-time profiles after administration of Test Formulation #1 (Treatment A), Test Formulation #2 (Treatment B), and Reference Product (Treatment C).

TABLE 20

Statistical Analysis of the Log-Transformed Systemic Exposure Parameters of d-Methylphenidate Comparing Test Formulation 1 (Treatment A) to the Reference Product (Treatment C)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 20.1714 | 16.3095 | 123.68 | 117.21 | 130.50 | 1.0000 | 14.10 |
| $\ln(AUC_{0-3})$ | 20.5344 | 23.7682 | 86.39 | 79.10 | 94.36 | 0.9935 | 23.36 |
| $\ln(AUC_{0-tmax})^d$ | 50.1624 | 50.0850 | 100.15 | 93.53 | 107.25 | 0.9998 | 18.03 |
| $\ln(AUC_{tmax-24})^d$ | 103.8409 | 95.3024 | 108.96 | 104.11 | 114.04 | 1.0000 | 11.94 |
| $\ln(AUC_{0-24})$ | 156.7217 | 146.3987 | 107.05 | 103.73 | 110.48 | 1.0000 | 8.25 |
| $\ln(AUC_{tmax-tlast})^d$ | 104.3909 | 100.4459 | 103.93 | 98.76 | 109.37 | 1.0000 | 13.39 |
| $\ln(AUC_{last})$ | 157.4500 | 151.7064 | 103.79 | 100.26 | 107.44 | 1.0000 | 9.05 |
| $\ln(AUC_{inf})$ | 161.1557 | 157.9722 | 102.02 | 98.78 | 105.35 | 1.0000 | 8.43 |

[a]Geometric Mean for the Test Formulation 1 (Test) and Reference Product (Ref) based on Least Squares Mean of log-transformed parameter values
[b]Ratio(%) = Geometric Mean (Test)/Geometric Mean (Ref)
[c]90% Confidence Interval
[d]The median $T_{max}$ of the Reference Product (5.00 hr) was used

TABLE 21

Statistical Analysis of the Log-Transformed Systemic Exposure Parameters of d-Methylphenidate Comparing Test Formulation 2 (Treatment B) to the Reference Product (Treatment C).

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 20.4113 | 16.3095 | 125.15 | 118.62 | 132.04 | 1.0000 | 14.10 |
| $\ln(AUC_{0-3})$ | 21.7843 | 23.7682 | 91.65 | 83.92 | 100.10 | 0.9936 | 23.36 |
| $\ln(AUC_{0-tmax})^d$ | 51.9061 | 50.0850 | 103.64 | 96.79 | 110.97 | 0.9998 | 18.03 |
| $\ln(AUC_{tmax-24})^d$ | 105.8856 | 95.3024 | 111.10 | 106.16 | 116.27 | 1.0000 | 11.94 |
| $\ln(AUC_{0-24})$ | 160.7525 | 146.3987 | 109.80 | 106.40 | 113.31 | 1.0000 | 8.25 |
| $\ln(AUC_{tmax-tlast})^d$ | 106.3546 | 100.4459 | 105.88 | 100.62 | 111.42 | 1.0000 | 13.39 |
| $\ln(AUC_{last})$ | 161.3617 | 151.7064 | 106.36 | 102.75 | 110.10 | 1.0000 | 9.05 |
| $\ln(AUC_{inf})$ | 165.4229 | 157.9722 | 104.72 | 101.40 | 108.14 | 1.0000 | 8.43 |

[a]Geometric Mean for the Test Formulation 2 (Test) and Reference Product (Ref) based on Least Squares Mean of log-transformed parameter values
[b]Ratio(%) = Geometric Mean (Test)/Geometric Mean (Ref)
[c]90% Confidence Interval
[d]The median $T_{max}$ of the Reference Product (5.00 hr) was used

TABLE 22

Statistical Analysis of the Log-Transformed Systemic Exposure Parameters of l-Methylphenidate Comparing Test Formulation 1 (Treatment A) to the Reference Product (Treatment C).

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 0.4471 | 0.2224 | 201.01 | 167.90 | 240.64 | 0.6550 | 49.75 |
| $\ln(AUC_{0-3})$ | 0.6292 | 0.2691 | 233.82 | 198.86 | 274.92 | 0.7346 | 44.29 |
| $\ln(AUC_{0-tmax})$[d] | 1.0739 | 0.5281 | 203.35 | 175.47 | 235.66 | 0.8024 | 40.01 |
| $\ln(AUC_{tmax-24})$[d] | 0.9649 | 0.7668 | 125.84 | 108.56 | 145.87 | 0.8013 | 40.08 |
| $\ln(AUC_{0-24})$ | 2.1909 | 1.3404 | 163.45 | 143.93 | 185.62 | 0.8936 | 34.18 |
| $\ln(AUC_{tmax-tlast})$[d] | 0.8821 | 0.7435 | 118.64 | 101.75 | 138.33 | 0.7736 | 41.81 |
| $\ln(AUC_{last})$ | 2.1125 | 1.3231 | 159.66 | 140.14 | 181.90 | 0.8801 | 35.09 |
| $\ln(AUC_{inf})$ | 2.2098 | 1.5598 | 141.68 | 122.06 | 164.44 | 0.7952 | 40.46 |

[a] Geometric Mean for the Test Formulation 1 (Test) and Reference Product (Ref) based on Least Squares Mean of log-transformed parameter values
[b] Ratio(%) = Geometric Mean (Test)/Geometric Mean (Ref)
[c] 90% Confidence Interval
[d] The median $T_{max}$ of the Reference Product (5.00 hr) was used

TABLE 23

Statistical Analysis of the Log-Transformed Systemic Exposure Parameters of l-Methylphenidate Comparing Test Formulation 2 (Treatment B) to the Reference Product (Treatment C)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 0.5092 | 0.2224 | 228.93 | 191.26 | 274.02 | 0.6557 | 49.75 |
| $\ln(AUC_{0-3})$ | 0.6798 | 0.2691 | 252.63 | 214.89 | 296.99 | 0.7354 | 44.29 |
| $\ln(AUC_{0-tmax})$[d] | 1.1261 | 0.5281 | 213.23 | 184.02 | 247.07 | 0.8031 | 40.01 |
| $\ln(AUC_{tmax-24})$[d] | 1.1095 | 0.7668 | 144.70 | 124.85 | 167.70 | 0.8021 | 40.08 |
| $\ln(AUC_{0-24})$ | 2.4426 | 1.3404 | 182.23 | 160.49 | 206.92 | 0.8942 | 34.18 |
| $\ln(AUC_{tmax-tlast})$[d] | 1.0239 | 0.7435 | 137.71 | 118.13 | 160.55 | 0.7744 | 41.81 |
| $\ln(AUC_{last})$ | 2.3641 | 1.3231 | 178.68 | 156.86 | 203.54 | 0.8807 | 35.09 |
| $\ln(AUC_{inf})$ | 2.4774 | 1.5598 | 158.83 | 136.87 | 184.32 | 0.7959 | 40.46 |

[a] Geometric Mean for the Test Formulation 2 (Test) and Reference Product (Ref) based on Least Squares Mean of log-transformed parameter values
[b] Ratio(%) = Geometric Mean (Test)/Geometric Mean (Ref)
[c] 90% Confidence Interval
[d] The median $T_{max}$ of the Reference Product (5.00 hr) was used

TABLE 24

Statistical Analysis of the Log-Transformed Systemic Exposure Parameters of Total Methylphenidate (d + l) Comparing Test Formulation 1 (Treatment A) to the Reference Product (Treatment C)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 20.6080 | 16.5477 | 124.54 | 117.98 | 131.46 | 1.0000 | 14.21 |
| $\ln(AUC_{0-3})$ | 21.2961 | 24.1188 | 88.30 | 80.92 | 96.35 | 0.9943 | 23.10 |
| $\ln(AUC_{0-tmax})$[d] | 51.4307 | 50.7312 | 101.38 | 94.67 | 108.56 | 0.9998 | 18.02 |
| $\ln(AUC_{tmax-24})$[d] | 105.0763 | 96.2603 | 109.16 | 104.30 | 114.24 | 1.0000 | 11.94 |
| $\ln(AUC_{0-24})$ | 159.2597 | 148.0008 | 107.61 | 104.29 | 111.03 | 1.0000 | 8.20 |
| $\ln(AUC_{tmax-tlast})$[d] | 105.6235 | 102.0912 | 103.46 | 98.33 | 108.86 | 1.0000 | 13.35 |
| $\ln(AUC_{last})$ | 159.9855 | 153.9687 | 103.91 | 100.39 | 107.55 | 1.0000 | 9.03 |
| $\ln(AUC_{inf})$ | 163.6833 | 159.5401 | 102.60 | 99.37 | 105.93 | 1.0000 | 8.36 |

[a] Geometric Mean for the Test Formulation 1 (Test) and Reference Product (Ref) based on Least Squares Mean of log-transformed parameter values
[b] Ratio(%) = Geometric Mean (Test)/Geometric Mean (Ref)
[c] 90% Confidence Interval
[d] The median $T_{max}$ of the Reference Product (5.00 hr) was used

TABLE 25

Statistical Analysis of the Log-Transformed Systemic Exposure Parameters of Total Methylphenidate (d + l) Comparing Test Formulation 2 (Treatment B) to the Reference Product (Treatment C).

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 20.8467 | 16.5477 | 125.98 | 119.35 | 132.97 | 1.0000 | 14.21 |
| $\ln(AUC_{0-3})$ | 22.5591 | 24.1188 | 93.53 | 85.73 | 102.05 | 0.9944 | 23.10 |
| $\ln(AUC_{0-tmax})$[d] | 53.1774 | 50.7312 | 104.82 | 97.90 | 112.24 | 0.9998 | 18.02 |
| $\ln(AUC_{tmax-24})$[d] | 107.4905 | 96.2603 | 111.67 | 106.70 | 116.86 | 1.0000 | 11.94 |
| $\ln(AUC_{0-24})$ | 163.6952 | 148.0008 | 110.60 | 107.20 | 114.12 | 1.0000 | 8.20 |
| $\ln(AUC_{tmax-tlast})$[d] | 108.1238 | 102.0912 | 105.91 | 100.66 | 111.43 | 1.0000 | 13.35 |
| $\ln(AUC_{last})$ | 164.4747 | 153.9687 | 106.82 | 103.21 | 110.57 | 1.0000 | 9.03 |
| $\ln(AUC_{inf})$ | 168.3659 | 159.5401 | 105.53 | 102.22 | 108.95 | 1.0000 | 8.36 |

[a] Geometric Mean for the Test Formulation 2 (Test) and Reference Product (Ref) based on Least Squares Mean of log-transformed parameter values
[b] Ratio(%) = Geometric Mean (Test)/Geometric Mean (Ref)
[c] 90% Confidence Interval
[d] The median $T_{max}$ of the Reference Product (5.00 hr) was used Conclusions Based on $C_{max}$, the peak exposure to d-methylphenidate is higher after administration of Test Formulations 1 and 2 relative to that after METADATE CD and the 90% confidence intervals about the ratios for $C_{max}$ (Test Formulation 1/Reference and Test Formulation 2/Reference) are not within the 80% to 125% range necessary to establish traditional bioequivalence. However, based on $AUC_{last}$ and $AUC_{inf}$, the overall systemic exposure to d-methylphenidate after administration of Test Formulations 1 and 2 is comparable to that after METADATE CD and the 90% confidence intervals about the ratios for $AUC_{last}$ and $AUC_{inf}$ are within the 80% to 125% range, indicating no significant difference in bioavailability. Except for $AUC_{0-3}$ after Test Formulation 1 (ratio: 86.39%; 90% confidence interval: 79.10%-94.36%), the 90% confidence intervals about the Test/Reference ratios for all partial AUCs are within the 80% to 125% range, indicating comparable early systemic exposure through $T_{max}$ (5.00 hr) and 24 hours after Test Formulations 1 and 2 relative to METADATE CD.

Based on $C_{max}$, $AUC_{last}$, and $AUC_{inf}$, peak and overall systemic exposure to l-methylphenidate is higher after administration of Test Formulations 1 and 2 relative to that after METADATE CD and the 90% confidence intervals about the Test/Reference ratios (Test Formulation 1/Reference and Test Formulation 2/Reference) are not within the 80% to 125% range necessary to establish traditional bioequivalence. Similarly, based on partial AUCs, early systemic exposure to l-methylphenidate is higher after administration of Test Formulations 1 and 2 relative to that after METADATE CD and the 90% confidence intervals about the Test/Reference ratios for all partial AUCs are not within the 80% to 125% range.

Based on $AUC_{last}$ and $AUC_{inf}$ the overall systemic exposure to total methylphenidate (d+l) after administration of Test Formulations 1 and 2 is comparable to that after METADATE CD and the 90% confidence intervals about the ratios for $AUC_{last}$ and $AUC_{inf}$ are within the 80% to 125% range, indicating no significant difference in bioavailability. In addition, the 90% confidence intervals about the Test/Reference ratios for all partial AUCs are within the 80% to 125% range, indicating comparable early systemic exposure through 3 hours, $T_{max}$ (5.00 hr), and 24 hours after Test Formulations 1 and 2 relative to METADATE CD.

Example 19

Ethanol Study

In vitro dissolution studies using methylphenidate compositions in the presence or absence of ethanol were also carried out. One 60 mg capsule of METADATE CD, and separately, two (30 mg) tablets of a formulation similar to Example 17, were introduced into USP dissolution Apparatus 2. The dissolution media started with alcoholic 0.1N HCl with various amounts of ethanol (0%, 5%, 10%, 20%, and 40%). Appropriate amounts of pH change buffer were added to the media at 2 hours (after the sample was introduced) to make the pH of the media to 6.8. Samples were taken at different time points. The results are shown in FIGS. 25A (METADATE CD), 25B (test formulation) and 25C (METADATE CD and test formulation).

Figure 25A:
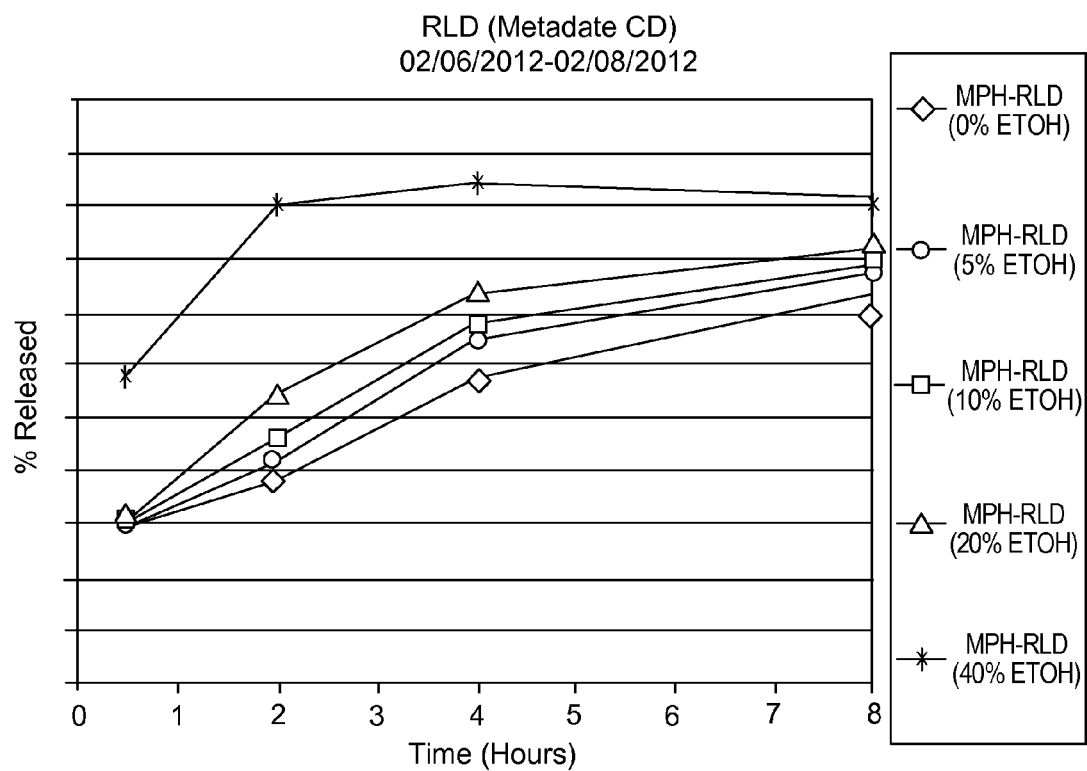
FIGS. 25A-25C show in vitro release profiles of METADATE CD (i.e., the reference drug) with the addition of 0%, 5%, 10%, 20%, and 40% alcohol (FIG. 25A), the in vitro release profiles of a formulation similar to those formulations described in Example 17 with the addition of 0%, 5%, 10%, 20%, and 40% alcohol (FIG. 25B), and the in vitro release profiles of METADATE CD and a formulation similar to those described in Example 17 with the addition of 0%, 5%, 10%, 20%, and 40% alcohol (FIG. 25C).

FIG. 25A shows that the addition of 40% ethanol substantially increases the amount of drug released in the reference formulation, i.e., there is a substantial increase in drug released through dose dumping in the presence of ethanol.

Figure 25B:
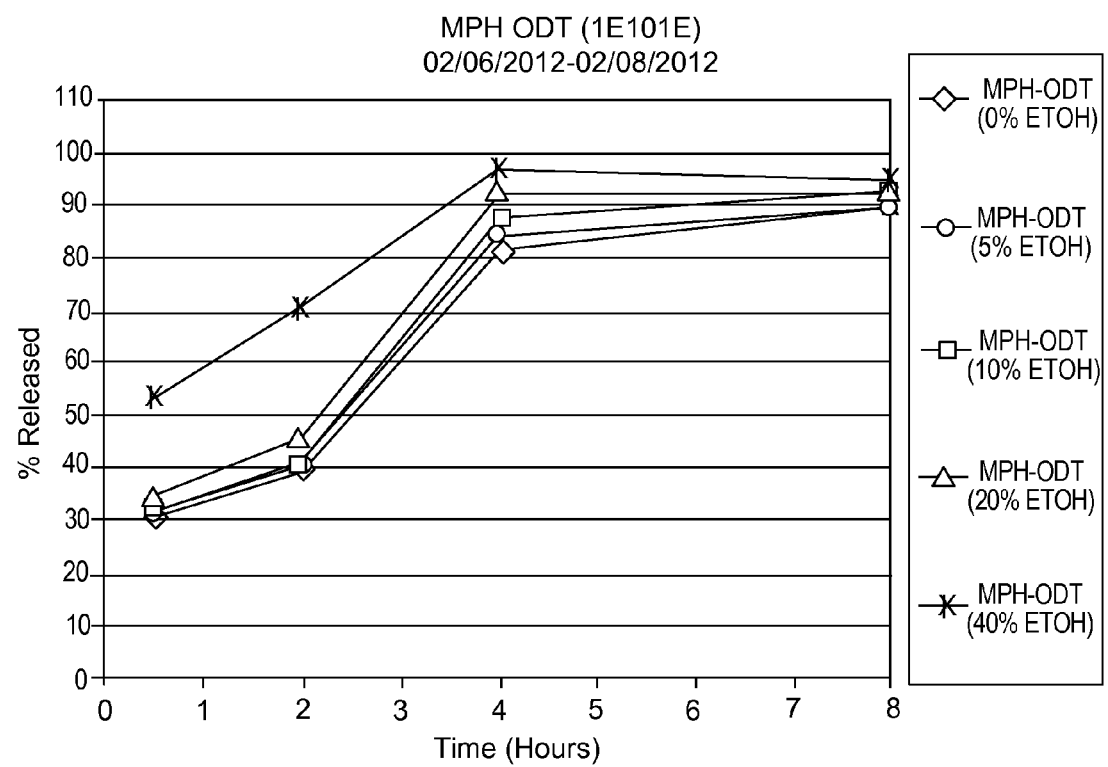
Figure 25C:
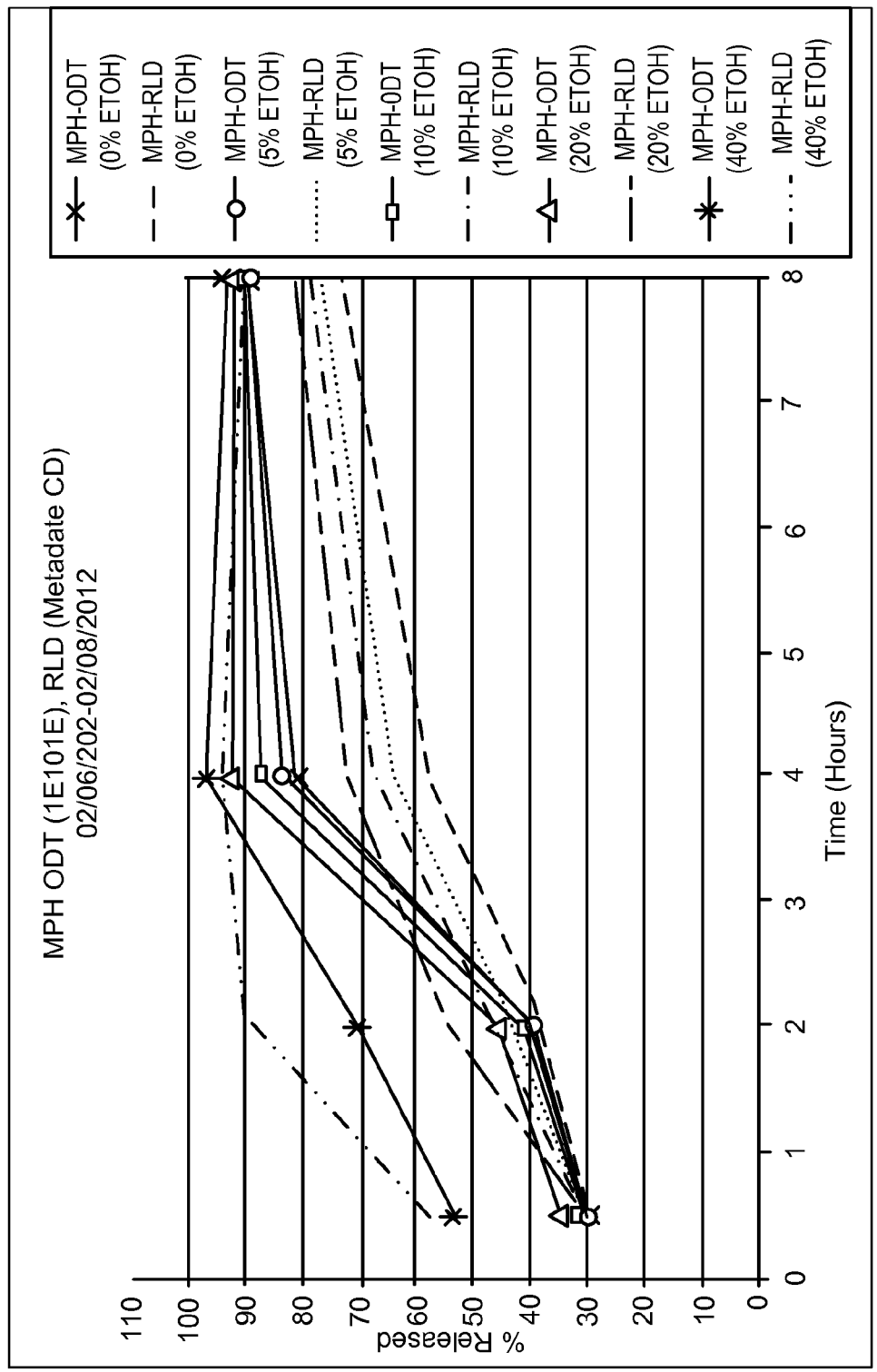

FIG. 25B shows that the addition 40% ethanol increases the amount of drug released but to a lesser extent than in the reference formulation. As such, the ethanol study's results show that, in the presence of ethanol, the formulations of the invention have a reduced exposure level of methylphenidate as compared to the reference formulation. This prevents or substantially reduces the likelihood of dose dumping when the formulations of the invention and ethanol are ingested by a subject.

Example 20

Food-Effect Study of an Extended Release Methylphenidate ODT Formulation in Healthy Subjects This example describes a single-dose, open-label, randomized, two-period crossover study that assessed the effect of food on the rate of absorption and oral bioavailability of a single dose (two ODTs) of a methylphenidate extended release ODT (equivalent to 60 mg methylphenidate HCl), under fed and fasted conditions.

Subjects in both treatment conditions fasted overnight for at least 10 hours. Subjects in the fed condition were dosed 5 minutes after completing consumption of a Food and Drug Administration (FDA) standard high-calorie, high-fat breakfast meal. Consumption of the FDA standard high-calorie, high-fat breakfast began 30 minutes prior to dosing. Subjects in the fasted condition continued to fast up until the time that they were dosed. Each drug administration was separated by a washout period of 7 days.

Subjects were administered a single 2 ODT dose of each of the treatments in a randomized, sequenced fashion. Immediately prior to dose, each subject was given 60 mL of room temperature water in a cup and instructed to swish the water around in the mouth and to spit it out in order to wet the mouth.

Treatment A (Fasted): Test Formulation #102 (shown below) was orally administered following a 10-hour overnight fast. Dose=2×methylphenidate polistirex ODT containing 26.1 mg methylphenidate base Formulation #102, equivalent to 60 mg of methylphenidate HCl.

Treatment B (Fed): Test Formulation #102 (shown below) was orally administered following a 10-hour overnight fast and consumption of an FDA standard high-fat, high-calorie breakfast beginning 30 minutes prior to dose. Dose=2×methylphenidate polistirex ODT, each containing 26.1 mg methylphenidate base Formulation #102; this dose is equivalent to 60 mg of methylphenidate HCl.

The subjects fasted for 4 hours thereafter. Standard meals were provided at approximately 4 and 10 hours after drug administration and at appropriate times thereafter.

Except for the 60 mL mouth rinse given immediately prior to each dose (and which the subjects spit out), no water was allowed for 1 hour prior through 1 hour after dose. Each subject was required to drink approximately 360 mL of fluid with each snack or meal administered during confinement after dosing on Day 1. Each subject was required to drink 120 mL of water at approximately 1, 2, and 3 hours after dose administration. Subjects were provided approximately 700 mL of water that was required to be consumed between lunch and snack administrations during confinement on Day 1. After snack administration on Day 1, water was allowed ad lib.

TABLE 26

ODT methylphenidate Formulation #102 with 25% IR and 75% ER/DR
IR Resin - 36.97% base assay & ER/DR Resin - 12.88% base assay

| | Formulation #102 (25% active from IR Resin & 75% active from ER/DR Resin) | | |
|---|---|---|---|
| | mg/dose | Notes | % |
| Uncoated (IR) MPH Resin | 17.65 | The 17.65 mg/dose quantity is the actual amount of IR resin (at a 36.97% assay value) that goes into each tablet. The values in the gray area are the quantities of each material that compromise the IR material. | 2.67 |
| Methylphenidate (base) | 6.525 | | |
| AMBERLITE IRP069 Resin + Water | 11.08 | | |
| Polyethylene Glycol | 0.045 | | |
| Coated (ER/DR) MPH Resin | 151.98 | The 151.98 mg/dose quantity is the actual amount of ER/DR resin (at a 12.88% assay value) that goes into each tablet. The IR resin material was used to make the 151.98 mg/dose ER/DR material. The values in the gray area are the quantities of each material that compromise the ER/DR material. | 23.03 |
| Methylphenidate (base) | 19.575 | | |
| AMBERLITE IRP069 Resin + Water | 32.04 | | |
| Polyethylene Glycol | 0.38 | | |
| Ethylcellulose N-10 | 12.00 | | |
| EUDRAGIT L100 | 75.94 | | |
| Triethyl Citrate | 12.045 | | |
| Prosolv ODT | 367.22 | The Prosolv ODT quantity will be variable to account for the variable assay value of the IR and DR resin. | 55.64 |
| Crospovidone | 66.00 | | 10.00 |
| Sucralose Powder | 23.00 | | 3.48 |
| Citric Acid | 10.00 | | 1.52 |
| Flavor & Color | 17.55 | | 2.66 |
| Magnesium Stearate | 6.60 | | 1.00 |
| Total | 660.00 mg | | 100% |

Data collection and analysis were carried out as similarly as described above. Twenty-three (23) of the 24 subjects enrolled completed the study. Data from 23 subjects were included in the pharmacokinetic and statistical analyses Mean concentration-time data are shown in FIGS. 27-29. Results of the pharmacokinetic and statistical analysis are shown below in Tables 27 through 29.

Figure 27A:
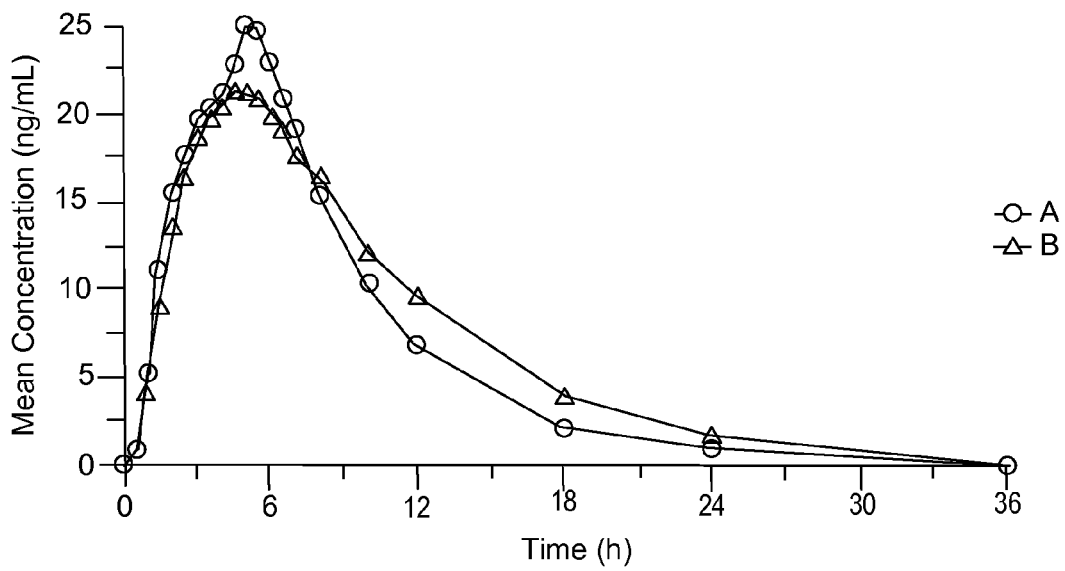
FIGS. 27A and 27B show the mean methylphenidate (d+l) concentration-time profiles after administration of Formulation #102-Fasted (Treatment A) and Formulation #102-Fed (Treatment B), as described in Example 20.
Figure 27B:
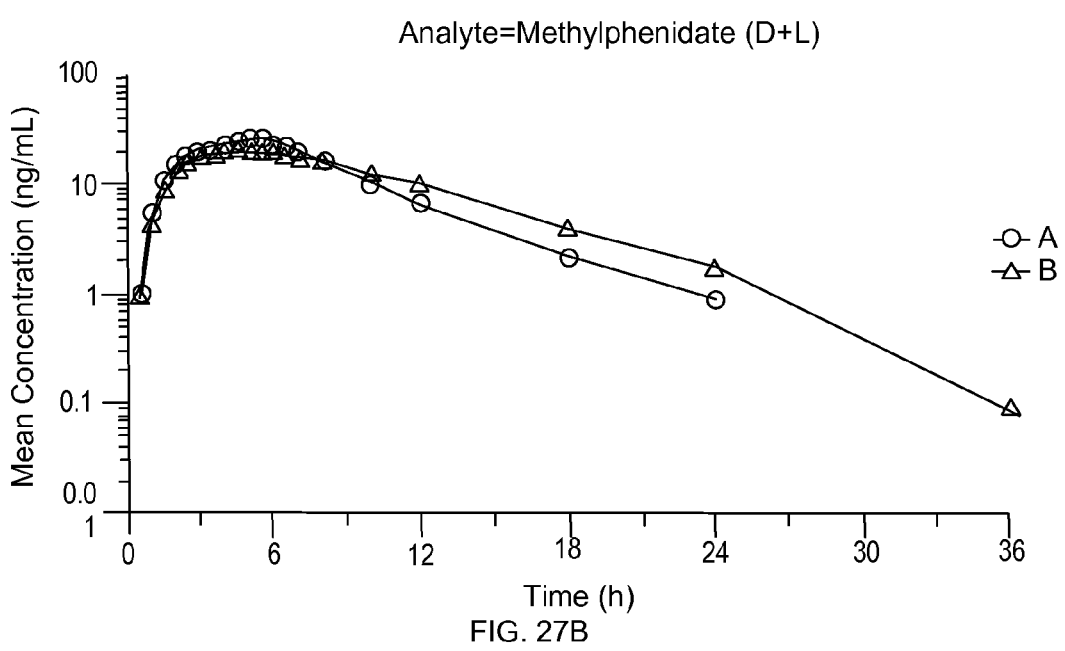

Results:

FIGS. 27A and 27B show the mean methylphenidate (d+l) concentration-time profiles after administration of Formulation #102-Fasted (Treatment A) and Formulation #102-Fed (Treatment B).

Figure 28A:
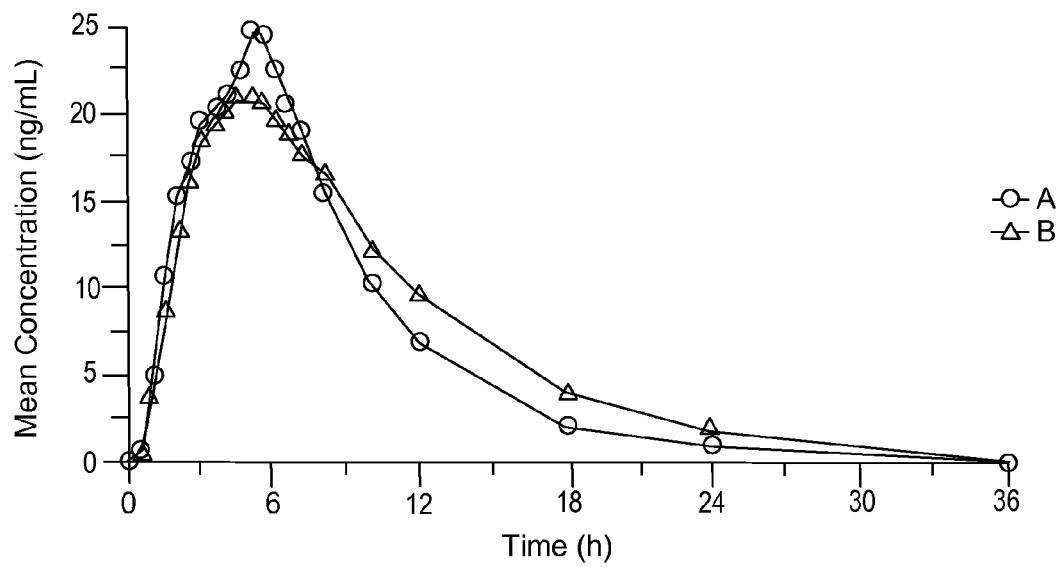
FIGS. 28A and 28B show the mean d-methylphenidate concentration-time profiles after administration of Formulation #102-Fasted (Treatment A) and Formulation #102-Fed (Treatment B), as described in Example 20.
Figure 28B:
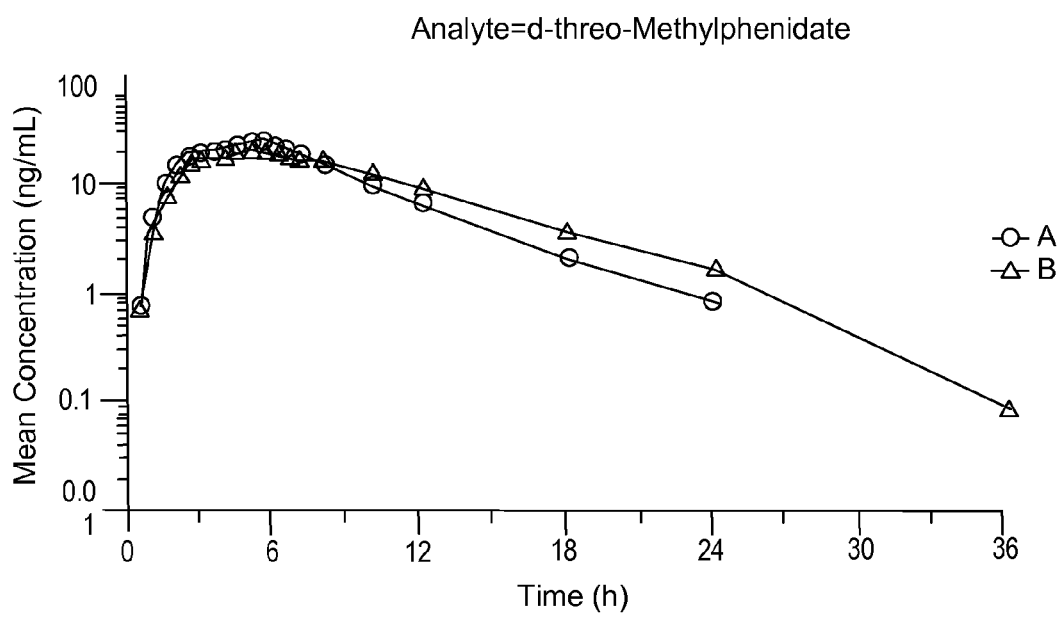

FIGS. 28A and 28B mean d-methylphenidate concentration-time profiles after administration of Formulation #102-Fasted (Treatment A) and Formulation #102-Fed (Treatment B).

Figure 29A:
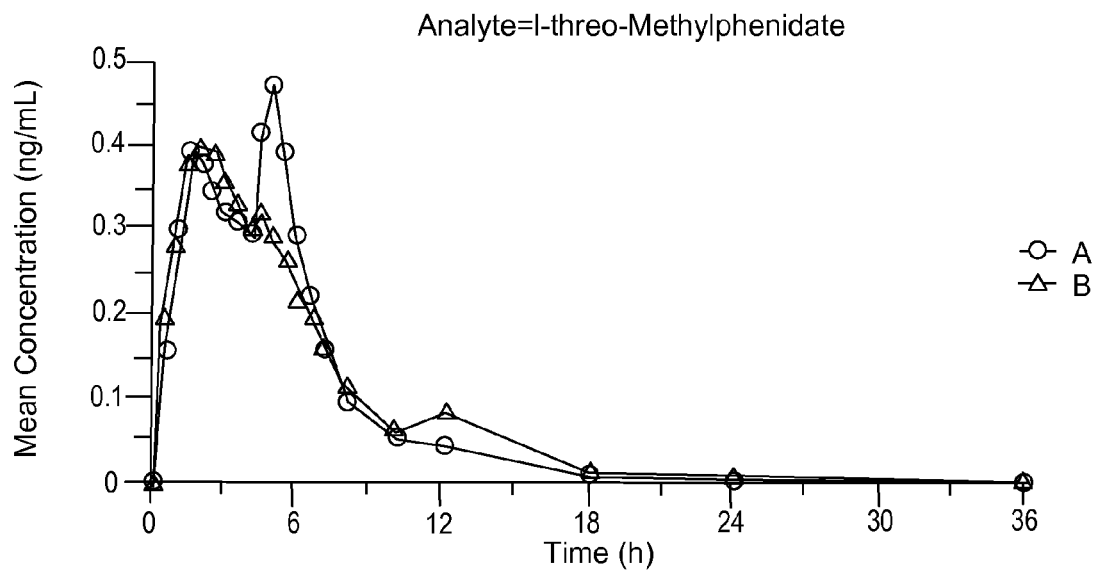
FIGS. 29A and 29B show the mean l-methylphenidate concentration-time profiles after administration of Formulation #102-Fasted (Treatment A) and Formulation #102-Fed (Treatment B), as described in Example 20.
Figure 29B:
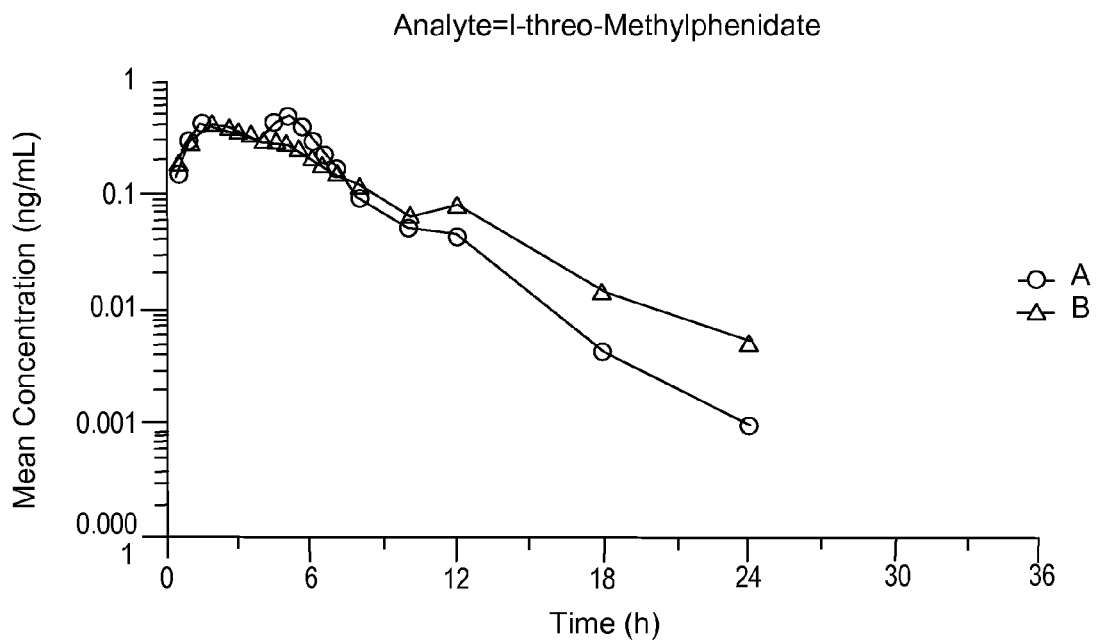

FIGS. 29A and 29B mean l-methylphenidate concentration-time profiles after administration of Formulation #102-Fasted (Treatment A) and Formulation #102-Fed (Treatment B).

TABLE 27

Statistical Analysis of the Log-Transformed Systemic Exposure Parameters of Methylphenidate (d + l)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 22.4817 | 25.9799 | 86.53 | 80.52 | 93.00 | 0.9992 | 14.25 |
| $\ln(AUC_{last})$ | 229.2966 | 205.8759 | 111.38 | 106.74 | 116.21 | 1.0000 | 8.38 |
| $\ln(AUC_{inf})$ | 237.5598 | 211.0504 | 112.56 | 108.18 | 117.11 | 1.0000 | 7.82 |

[a]Geometric Mean for Formulation #102-Fed (Test) and Formulation #102-Fasted (Ref) based on Least Squares Mean of log-transformed parameter values
[b]Ratio(%) = Geometric Mean (Test)/Geometric Mean (Ref)
[c]90% Confidence Interval

TABLE 28

Statistical Analysis of the Log-Transformed Systemic Exposure Parameters of d-Methylphenidate

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 22.1811 | 25.5705 | 86.74 | 80.74 | 93.20 | 0.9992 | 14.20 |
| $\ln(AUC_{last})$ | 226.7299 | 203.5182 | 111.41 | 106.79 | 116.22 | 1.0000 | 8.34 |
| $\ln(AUC_{inf})$ | 234.9939 | 208.7056 | 112.60 | 108.24 | 117.13 | 1.0000 | 7.78 |

[a]Geometric Mean for Formulation #102 -Fed (Test) and Formulation #102 -Fasted (Ref) based on Least Squares Mean of log-transformed parameter values
[b]Ratio(%) = Geometric Mean (Test)/Geometric Mean (Ref)
[c]90% Confidence Interval

TABLE 29

Statistical Analysis of the Log-Transformed Systemic Exposure Parameters of l-Methylphenidate

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 0.3806 | 0.4171 | 91.25 | 74.52 | 111.73 | 0.5695 | 41.51 |
| $\ln(AUC_{last})$ | 2.1957 | 1.9338 | 113.54 | 99.76 | 129.23 | 0.8869 | 25.90 |
| $\ln(AUC_{inf})$ | 2.3594 | 2.0529 | 114.93 | 100.74 | 131.12 | 0.8768 | 26.40 |

[a]Geometric Mean for Formulation #102 -Fed (Test) and Formulation #102 -Fasted (Ref) based on Least Squares Mean of log-transformed parameter values
[b]Ratio(%) = Geometric Mean (Test)/Geometric Mean (Ref)
[c]90% Confidence Interval Conclusions There were no unusual or unexpected adverse events (AEs) related to the study medication. In general, the AE profile was consistent with the mechanism of action for this drug.

The 90% confidence intervals for comparing the log-transformed exposure parameters $\ln(C_{max})$, $\ln(AUC_{last})$, and $\ln(AUC_{inf})$ were within the accepted 80% to 125% limits for the a priori designated endpoint, methylphenidate (d+l).

Therefore, the presence of food did not significantly alter methylphenidate (d+l) exposure following the administration of methylphenidate-polistirex formulated as ODT (equivalent to 60 mg methylphenidate HCl) under fasting and fed conditions.

Example 21

The Effect of Food on the Pharmacokinetics of a Controlled Release Amphetamine ODT in Healthy Subjects This example describes a single-dose, open-label, randomized, two-period, two-treatment crossover study that assessed the effect of food on the rate of absorption and oral bioavailability of a controlled release ODT preparations of mixed amphetamine polistirex (equivalent to 30 mg mixed amphetamines), under fed and fasted conditions.

The protocol was the same as described in Example 20, except subjects received treatment listed below during the two treatment periods:

Treatment A (Fed Conditions): Test Formulation #1002A (mixed amphetamine resins) controlled-release ODT (shown below). Dose=1×mixed amphetamine polistirex ODT equivalent to 30 mg mixed amphetamine salts.

Treatment B (Fasted Conditions): Test Formulation #1002A (mixed amphetamine resins) controlled-release ODT (shown below). Dose=1×mixed amphetamine polistirex ODT equivalent to 30 mg mixed amphetamine salts.

TABLE 30

ODT amphetamine formulation with 45% IR and 55% DR
IR Resin - 34.08% base assay & DR Resin - 7.28% base assay

| | Formula #1002A (45% active from IR Resin & 55% active from DR Resin) | | |
|---|---|---|---|
| | mg/dose | Notes | % |
| Uncoated (IR) AMP Resin | 24.8 | The 24.8 mg/dose quantity is the | 3.76 |
| Amphetamine (base) | 4.23 | actual amount of IR resin (at a 34.08% | |
| Dextroamphetamine (base) | 4.23 | assay value) that goes into each tablet. | |
| AMBERLITE IRP069 Resin + Water | 16.34 | The values in the gray area are the quantities of each material that compromise the IR material. | |
| Coated (DR) AMP Resin | 142.0 | The 142.0 mg/dose quantity is the | 21.52 |
| Amphetamine (base) | 5.17 | actual amount of DR resin (at an 7.28% | |
| Dextroamphetamine (base) | 5.17 | assay value) that goes into each tablet. | |
| AMBERLITE IRP069 Resin + Water | 23.75 | The IR resin material was used to make | |
| Humectant | 0.32 | the 142.0 mg/dose DR material. | |
| EUDRAGIT L100 | 93.72 | The values in the gray area are the | |
| Plasticizer | 13.87 | quantities of each material that compromise the DR material. | |
| Prosolv ODT | 323.3 | The Prosolv ODT quantity will | 48.98 |
| Crospovidone | 105.6 | be variable to account for the variable | 16.00 |
| Sucralose Powder | 20.3 | assay value of the IR and DR resin. | 3.08 |
| Citric Acid | 22.5 | | 3.41 |
| Color and Flavor | 14.9 | | 2.26 |
| Magnesium Stearate | 6.6 | | 1.00 |
| Total | 660.00 mg | | 100% |

Figure 30A:
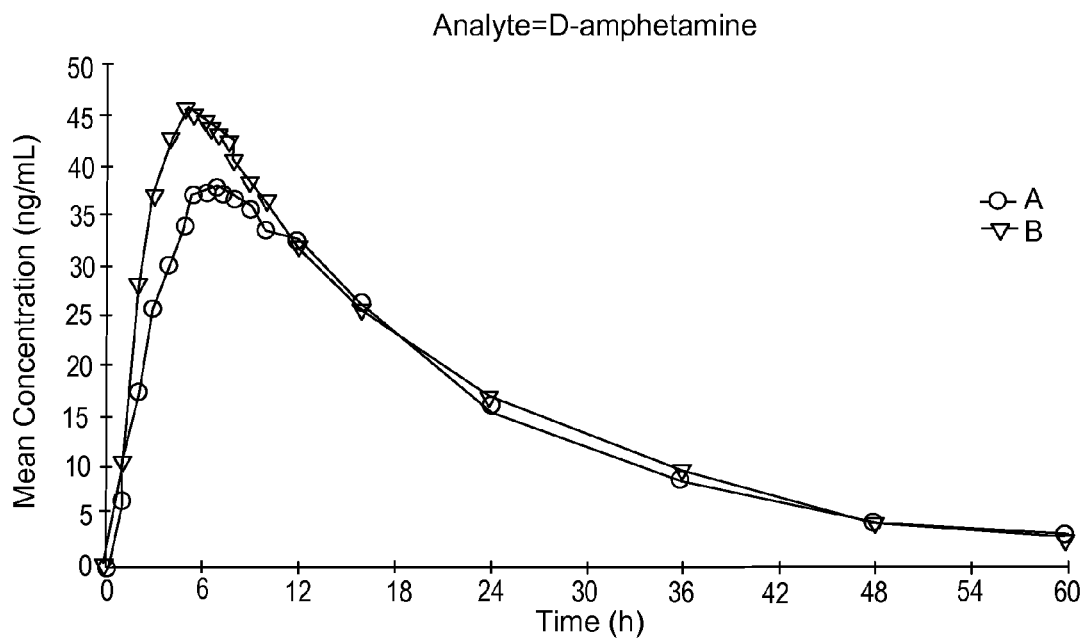
FIGS. 30A and 30B show the mean d-amphetamine concentration-time profiles after administration of test formulation-fed (Treatment A) and test formulation-fasted (Treatment B), as described in Example 21.
Figure 30B:
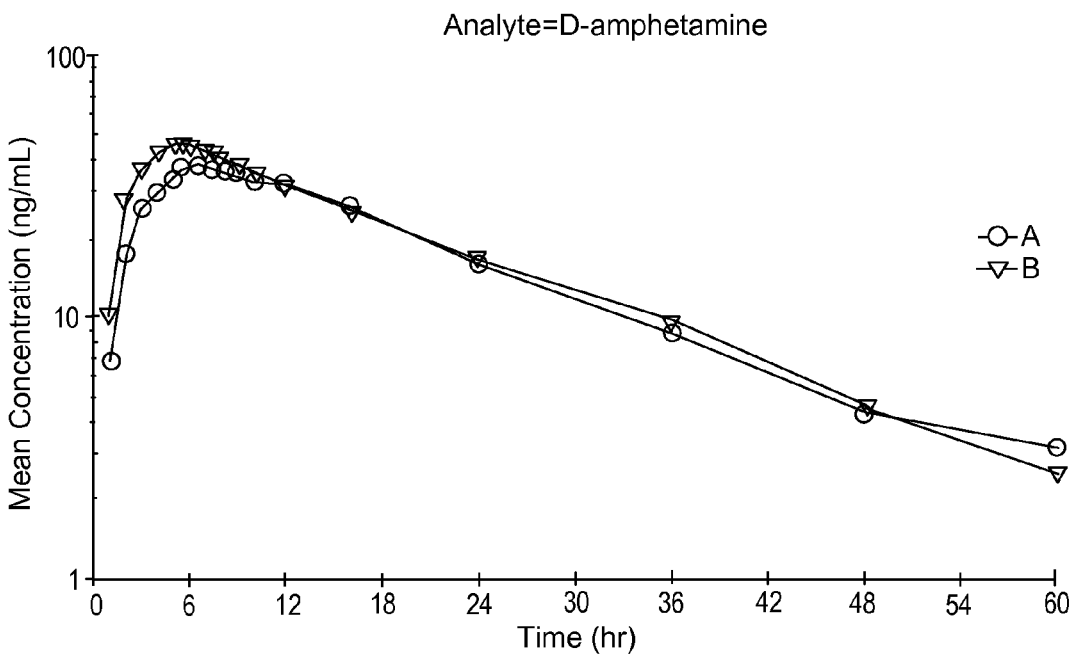
Figure 31A:
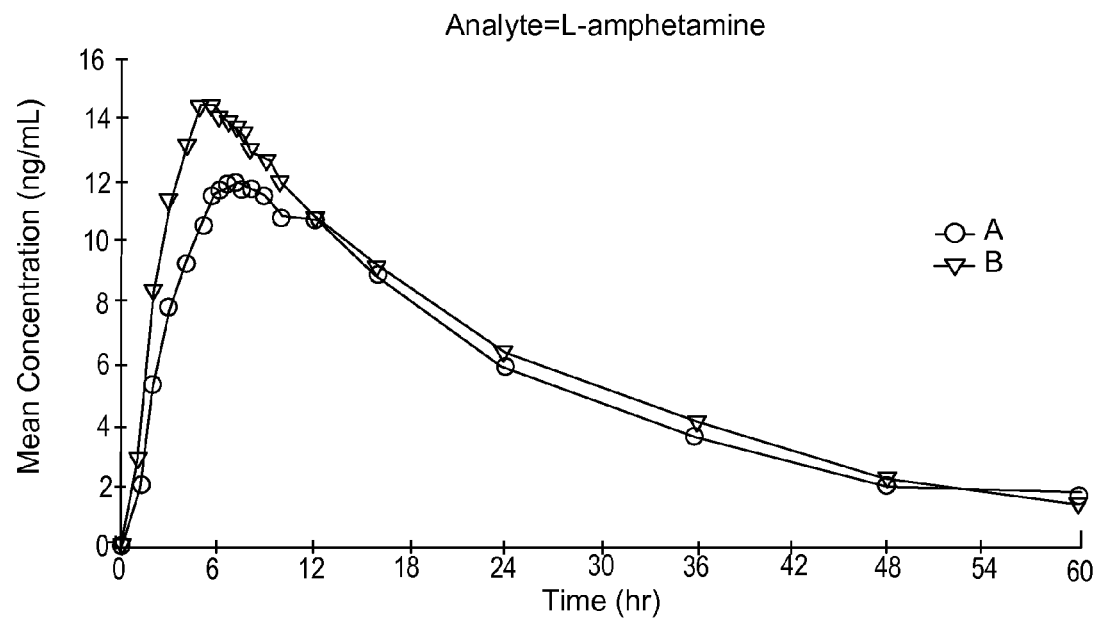
FIGS. 31A and 31B show the mean l-amphetamine concentration-time profiles after administration of test formulation-fed (Treatment A) and test formulation-fasted (Treatment B), as described in Example 21.
Figure 31B:
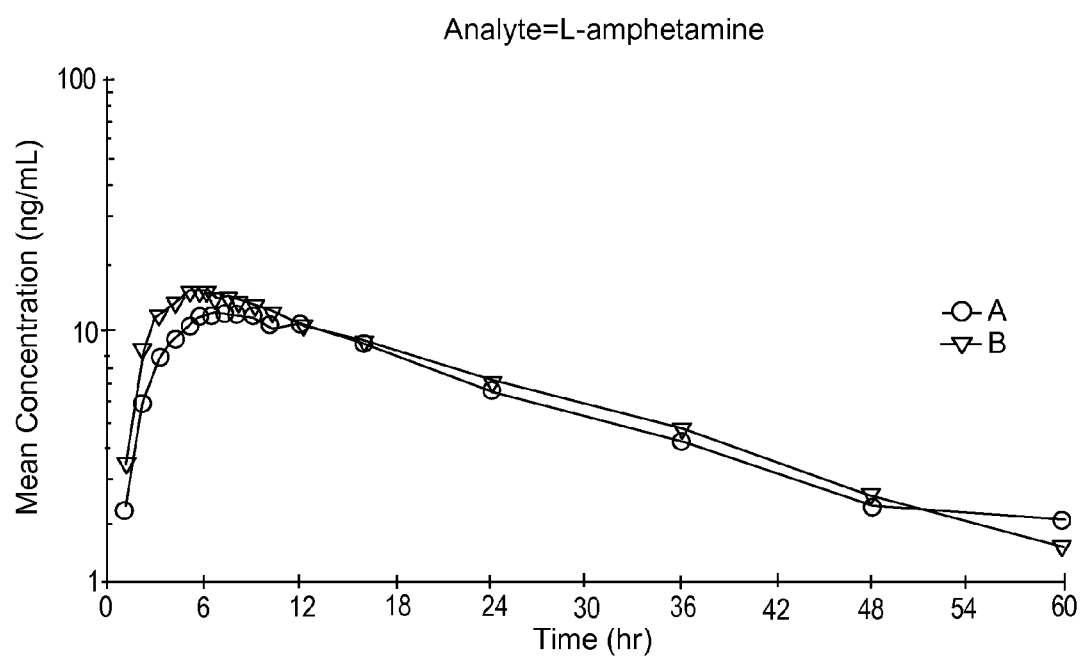

Data collection and analysis were carried out similarly as described above. All 16 subjects enrolled completed the study. Data from the 16 subjects were included in the pharmacokinetic and statistical analyses. Mean concentration-time data are shown in FIGS. 30 and 31. Results of the pharmacokinetic and statistical analysis are shown below in Tables 31 and 32.

Results

TABLE 31

Statistical Analysis of the Log-Transformed Systemic Exposure Parameters of d-amphetamine Comparing Test Formulation-Fed (Treatment A) to Test Formulation-Fasted (Treatment B)

| Dependent Variable | Geometric Mean[a] | | Ratio (%)[b] (Fed/Fasted) | 90% CI[c] | | ANOVA | |
|---|---|---|---|---|---|---|---|
| | Fed | Fasted | | Lower | Upper | Power | CV % |
| $\ln(C_{max})$ | 40.8357 | 47.6112 | 85.77 | 81.34 | 90.44 | 1.0000 | 8.54 |
| $\ln(AUC_{last})$ | 886.6801 | 962.1617 | 92.16 | 88.40 | 96.07 | 1.0000 | 6.68 |
| $\ln(AUC_{inf})$ | 941.2440 | 1018.5933 | 92.41 | 88.11 | 96.91 | 1.0000 | 7.35 |

[a]Geometric Mean for the Test Formulation-Fed and Test Formulation-Fasted based on Least Squares Mean of log-transformed parameter values
[b]Ratio(%) = Geometric Mean (Fed)/Geometric Mean (Fasted)
[c]90% Confidence Interval Note:
$T_{1/2}$ and parameters based on extrapolation could not be calculated for all subjects; statistical analysis is based on n = 16 for $C_{max}$, $AUC_{last}$ and n = 15 for $AUC_{inf}$

TABLE 32

Statistical Analysis of the Log-Transformed Systemic Exposure Parameters of l-amphetamine Comparing Test Formulation-Fed (Treatment A) to Test Formulation-Fasted (Treatment B)

| Dependent Variable | Geometric Mean[a] | | Ratio (%)[b] (Fed/Fasted) | 90% CI[c] | | ANOVA | |
|---|---|---|---|---|---|---|---|
| | Fed | Fasted | | Lower | Upper | Power | CV % |
| $\ln(C_{max})$ | 12.8378 | 14.8236 | 86.60 | 82.37 | 91.06 | 1.0000 | 8.07 |
| $\ln(AUC_{last})$ | 312.5311 | 342.9993 | 91.12 | 86.84 | 95.61 | 1.0000 | 7.74 |
| $\ln(AUC_{inf})$ | 346.2042 | 378.5080 | 91.47 | 86.33 | 96.91 | 0.9999 | 8.94 |

[a]Geometric Mean for the Test Formulation-Fed and Test Formulation-Fasted based on Least Squares Mean of log-transformed parameter values
[b]Ratio(%) = Geometric Mean (Fed)/Geometric Mean (Fasted)
[c]90% Confidence Interval Note:
$T_{1/2}$ and parameters based on extrapolation could not be calculated for all subjects; statistical analysis is based on n = 16 for $C_{max}$, $AUC_{last}$ and n = 15 for $AUC_{inf}$ Conclusions There were no unusual or unexpected adverse events related to the study medication. Study exit clinical laboratory, ECG, and physical examination evaluations were completed with no clinically significant findings. The 90% confidence intervals for comparing the maximum exposure, based on $\ln(C_{max})$, are within 80% to 125% for both d- and l-amphetamine. The 90% confidence intervals for comparing total systemic exposure, based on $\ln(AUC_{last})$ and $\ln(AUC_{inf})$, are within 80% to 125% for both d- and l-amphetamine. On the other hand, $T_{max}$ values were statistically different for the two treatments.

These data confirm that the extended-release characteristics of ODT containing amphetamine polistirex were maintained in the presence of a high-fat meal, and that a high-fat meal does not have a significant effect on the rate of absorption or oral bioavailability of mixed amphetamine resins in controlled-release ODT.

Example 22

The Effect of Alcohol on the Pharmacokinetics of a Controlled Release Amphetamine ODT in Healthy Subjects This example describes a single-dose, open-label, randomized, four-period, four-treatment, four-sequence crossover study that assessed the effect of varying concentrations of alcohol on the rate of absorption and oral bioavailability of a controlled release ODT preparation of mixed amphetamine polistirex (equivalent to 30 mg mixed amphetamines), in healthy adults.

Subjects fasted overnight for at least 10 hours, but were administered intravenous (IV) fluids continuously from approximately 10 hours predose to approximately 2 hours predose. The subjects received dose administrations of a controlled-release ODT preparation of amphetamines followed by varying concentrations of alcohol. Subjects were assigned to one of two cohorts (Group 1 or Group 2), randomly assigned to a treatment sequence, and received four, separate single-dose administrations of study medication, one treatment per period, according to the randomization schedule. Dosing days were separated by a washout period of at least 14 days. Subjects were divided into two groups of 16.

Subjects received the treatments listed below during the four treatment periods:

Treatment A: Test Formulation #1002A (described in Example 21) controlled-release ODT followed by 240 mL of deionized water (0% ethanol).

Treatment B: Test Formulation #1002A (described in Example 21) controlled-release ODT followed by 240 mL of 4% ethanol solution.

Treatment C: Test Formulation #1002A (described in Example 21) controlled-release ODT followed by 240 mL of 20% ethanol solution Treatment D: Test Formulation #1002A (described in Example 21) controlled-release ODT followed by 240 mL of 40% ethanol solution.

Subjects were given a single oral dose of the formulation followed by varying amounts of alcohol at a pre-specified time in each period, after a 10 hour overnight fast that was preceded by a standard meal. The subjects fasted for 4 hours thereafter. Water was allowed ad lib during the study except for 1 hour prior through 1 hour post-dose. Standard meals were provided at approximately 4 and 10 hours after drug administration and at appropriate times thereafter.

The water and/or alcohol solution was administered following confirmation that the ODT formulation had completely disintegrated. The deionized water and/or alcohol solution was consumed within 30 minutes.

Data collection and analysis were carried out as similarly as described above. Twenty seven (27) of the 32 subjects enrolled completed the study. Data from 32 subjects who completed at least one study period were included in the pharmacokinetic and statistical analyses. Mean concentration-time data are showing in FIGS. 32 and 33. Results of the pharmacokinetic and statistical analysis are shown below in Tables 33 through 38.

Results

Figure 32A:
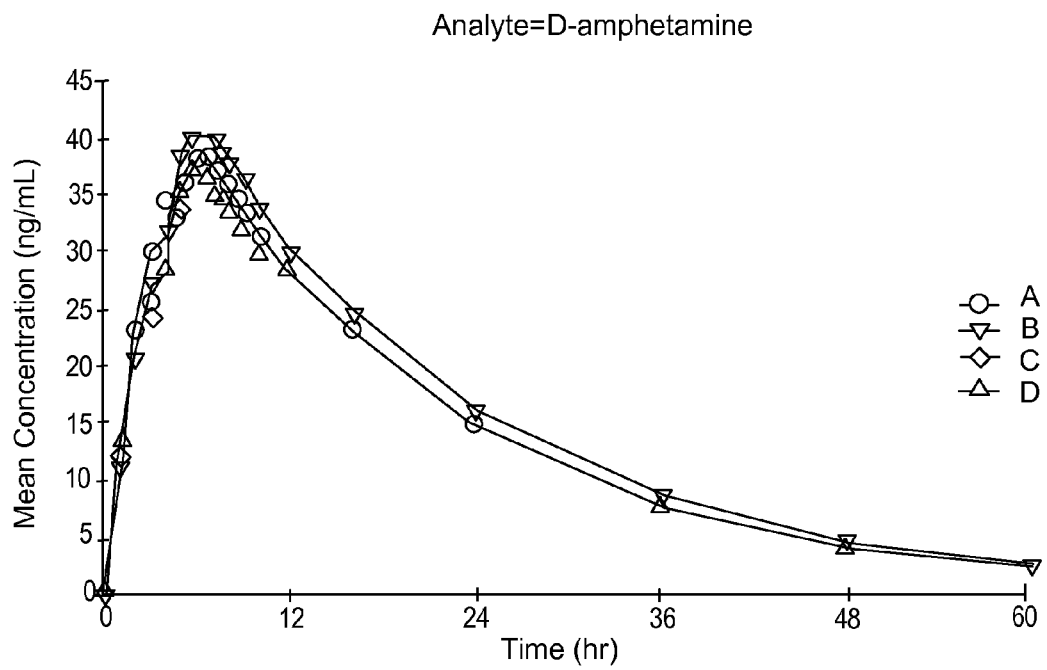
FIGS. 32A and 32B show the mean d-amphetamine concentration-time profiles after administration of controlled release ODT with Deionized Water (0% Ethanol Solution) (Treatment A), 4% ethanol (Treatment B), 20% ethanol (Treatment C) and 40% ethanol (Treatment D) on linear (upper panel) and semi-logarithmic (lower panel) scales, as described in Example 22.
Figure 32B:
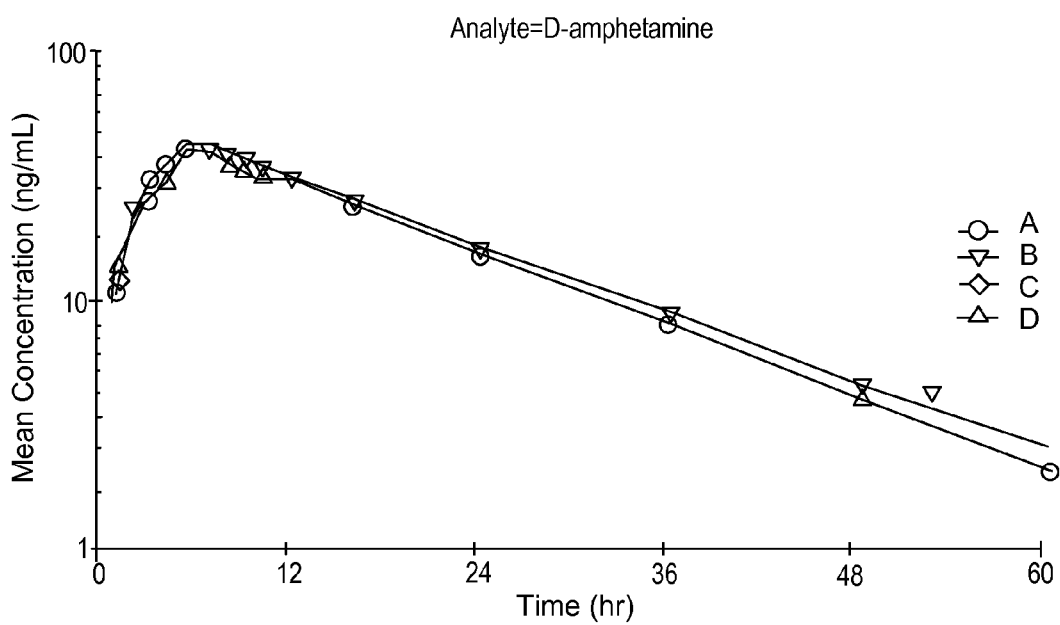

FIGS. 32A and 32B show mean d-amphetamine concentration-time profiles after administration of controlled Release ODT with Deionized Water (0% Ethanol Solution) (Treatment A), 4% ethanol (Treatment B), 20% ethanol (Treatment C) and 40% ethanol (Treatment D) on linear (upper panel) and semi-logarithmic (lower panel) scales.

Figure 33A:
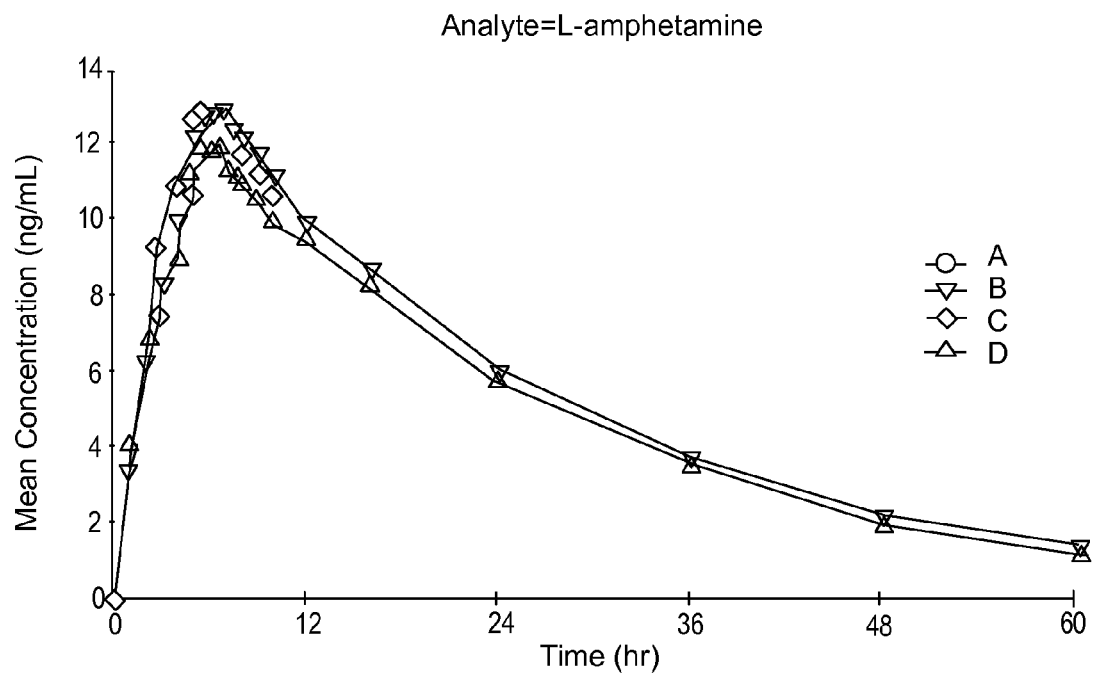
FIGS. 33A and 33B shows the mean l-amphetamine concentration-time profiles after administration of controlled release ODT with Deionized Water (0% Ethanol Solution) (Treatment A), 4% ethanol (Treatment B), 20% ethanol (Treatment C) and 40% ethanol (Treatment D) on linear (upper panel) and semi-logarithmic (lower panel) scales, as described in Example 22.
Figure 33B:
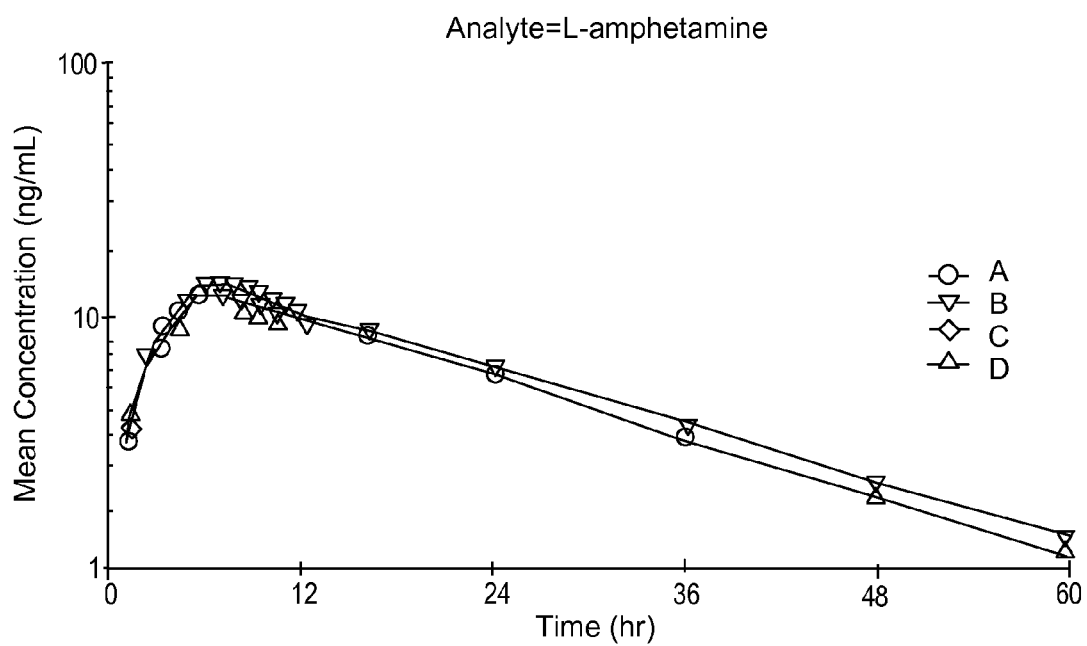

FIGS. 33A and 33B show mean l-amphetamine concentration-time profiles after administration of controlled Release ODT with Deionized Water (0% Ethanol Solution) (Treatment A), 4% ethanol (Treatment B), 20% ethanol (Treatment C) and 40% ethanol (Treatment D) on linear (upper panel) and semi-logarithmic (lower panel) scales.

TABLE 33

Statistical Analysis of the Log-Transformed Systemic Exposure Parameters of d-amphetamine Comparing Formula #1002A + 4% Ethanol (Treatment B) to Formula #1002A + Deionized Water (0% Ethanol Solution) (Treatment A)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 42.6047 | 41.6151 | 102.38 | 98.11 | 106.83 | 1.0000 | 9.88 |
| $\ln(AUC_{last})$ | 880.9005 | 854.9740 | 103.03 | 97.48 | 108.90 | 1.0000 | 12.88 |
| $\ln(AUC_{inf})$ [GRP1] | 1000.2608 | 931.5954 | 107.37 | 102.69 | 112.27 | 1.0000 | 6.96 |
| $\ln(AUC_{inf})$ [GRP2] | 909.5489 | 865.2939 | 105.11 | 100.49 | 109.95 | 1.0000 | 7.39 |

[a]Geometric Mean for Formula #1002A + 4% Ethanol (Test) Formula #1002A + Deionized Water (0% Ethanol Solution) (Ref) based on Least Squares Mean of log-transformed parameter values
[b]Ratio(%) = Geometric Mean (Test)/Geometric Mean (Ref)
[c]90% Confidence Interval
[GRP1/GRP2] = Group 1/Group 2

TABLE 34

Statistical Analysis of the Log-Transformed Systemic Exposure Parameters of d-amphetamine Comparing Formula #1002A + 20% Ethanol (Treatment C) to Formula #1002A + Deionized Water (0% Ethanol Solution) (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 40.0621 | 41.6151 | 96.27 | 92.21 | 100.51 | 1.0000 | 9.88 |
| $\ln(AUC_{last})$ | 841.7095 | 854.9740 | 98.45 | 93.08 | 104.13 | 1.0000 | 12.88 |
| $\ln(AUC_{inf})$ GRP1 | 895.8201 | 931.5954 | 96.16 | 91.85 | 100.67 | 1.0000 | 6.96 |
| $\ln(AUC_{inf})$ GRP2 | 916.3051 | 865.2939 | 105.90 | 101.24 | 110.77 | 1.0000 | 7.39 |

[a]Geometric Mean for Formula #1002A + 20% Ethanol (Test) and Formula #1002A + Deionized Water (0% Ethanol Solution) (Ref) based on Least Squares Mean of log-transformed parameter values
[b]Ratio(%) = Geometric Mean (Test)/Geometric Mean (Ref)
[c]90% Confidence Interval
GRP1/GRP2 = Group 1/Group 2

TABLE 35

Statistical Analysis of the Log-Transformed Systemic Exposure Parameters of d-amphetamine Comparing Formula #1002A + 40% Ethanol (Treatment D) to Formula #1002A + Deionized Water (0% Ethanol Solution) (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 39.5057 | 41.6151 | 94.93 | 90.88 | 99.17 | 1.0000 | 9.88 |
| $\ln(AUC_{last})$ | 848.9149 | 854.9740 | 99.29 | 93.81 | 105.10 | 1.0000 | 12.88 |
| $\ln(AUC_{inf})$ GRP1 | 908.1250 | 931.5954 | 97.48 | 93.18 | 101.98 | 1.0000 | 6.96 |
| $\ln(AUC_{inf})$ GRP2 | 868.8805 | 865.2939 | 100.41 | 95.91 | 105.13 | 1.0000 | 7.39 |

[a]Geometric Mean for Formula #1002A + 40% Ethanol (Test) and Formula #1002A + Deionized Water (0% Ethanol Solution) (Ref) based on Least Squares Mean of log-transformed parameter values
[b]Ratio(%) = Geometric Mean (Test)/Geometric Mean (Ref)
[c]90% Confidence Interval
GRP1/GRP2 = Group 1/Group 2

TABLE 36

Statistical Analysis of the Log-Transformed Systemic Exposure Parameters of l-amphetamine Comparing Formula #1002A + 4% Ethanol (Treatment B) to Formula #1002A + Deionized Water (0% Ethanol Solution) (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 13.6773 | 13.3098 | 102.76 | 98.64 | 107.05 | 1.0000 | 9.50 |
| $\ln(AUC_{last})$ | 316.6826 | 307.3284 | 103.04 | 96.77 | 109.73 | 1.0000 | 14.63 |
| $\ln(AUC_{inf})$ GRP1 | 379.7166 | 345.8712 | 109.79 | 103.92 | 115.98 | 1.0000 | 8.56 |
| $\ln(AUC_{inf})$ GRP2 | 342.6777 | 325.5756 | 105.25 | 100.16 | 110.60 | 1.000 | 8.15 |

[a]Geometric Mean for Formula #1002A + 4% Ethanol (Test) and Formula #1002A + Deionized Water (0% Ethanol Solution) (Ref) based on Least Squares Mean of log-transformed parameter values
[b]Ratio(%) = Geometric Mean (Test)/Geometric Mean (Ref)
[c]90% Confidence Interval
GRP1/GRP2 = Group 1/Group 2

TABLE 37

Statistical Analysis of the Log-Transformed Systemic Exposure Parameters of l-amphetamine Comparing Formula #1002A + 20% Ethanol (Treatment C) to Formula #1002A + Deionized Water (0% Ethanol Solution) (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| $\ln(C_{max})$ | 12.9647 | 13.3098 | 97.41 | 93.45 | 101.53 | 1.0000 | 9.50 |
| $\ln(AUC_{last})$ | 301.3609 | 307.3284 | 98.06 | 92.01 | 104.50 | 1.0000 | 14.63 |
| $\ln(AUC_{inf})$ GRP1 | 333.1404 | 345.8712 | 96.32 | 91.03 | 101.91 | 1.000 | 8.56 |
| $\ln(AUC_{inf})$ GRP2 | 346.3956 | 325.5756 | 106.39 | 101.25 | 111.80 | 1.0000 | 8.15 |

[a]Geometric Mean for Formula #1002A + 20% Ethanol (Test) and Formula #1002A + Deionized Water (0% Ethanol Solution) (Ref) based on Least Squares Mean of log-transformed parameter values TABLE 37-continued Statistical Analysis of the Log-Transformed Systemic Exposure Parameters
of l-amphetamine Comparing Formula #1002A + 20% Ethanol (Treatment
C) to Formula #1002A + Deionized Water (0% Ethanol Solution) (Treatment A)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |

[b]Ratio(%) = Geometric Mean (Test)/Geometric Mean (Ref)
[c]90% Confidence Interval
GRP1/GRP2 = Group 1/Group 2

TABLE 38

Statistical Analysis of the Log-Transformed Systemic Exposure Parameters
of l-amphetamine Comparing Formula #1002A + 40% Ethanol (Treatment
D) to Formula #1002A + Deionized Water (0% Ethanol Solution) (Treatment A)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 12.6112 | 13.3098 | 94.75 | 90.86 | 98.81 | 1.0000 | 9.50 |
| $\ln(AUC_{last})$ | 306.0284 | 307.3284 | 99.58 | 93.36 | 106.21 | 1.0000 | 14.63 |
| $\ln(AUC_{inf})$ GRP1 | 337.9262 | 345.8712 | 97.70 | 92.43 | 103.27 | 1.0000 | 8.56 |
| $\ln(AUC_{inf})$ GRP2 | 328.1746 | 325.5756 | 100.80 | 95.83 | 106.03 | 1.0000 | 8.15 |

[a]Geometric Mean for Formula #1002A + 40% Ethanol (Test) and Formula #1002A + Deionized Water (0% Ethanol Solution) (Ref) based on Least Squares Mean of log-transformed parameter values
[b]Ratio(%) = Geometric Mean (Test)/Geometric Mean (Ref)
[c]90% Confidence Interval
GRP1/GRP2 = Group 1/Group 2

Conclusions:

The 90% confidence intervals for comparing the maximum exposure to d-amphetamine and l-amphetamine, based on $\ln(C_{max})$, are within the accepted 80% to 125% limits across all comparisons The 90% confidence intervals for comparing total systemic exposure to d-amphetamine and l-amphetamine, based on $\ln(AUC_{last})$ and $\ln(AUC_{inf})$, are within the accepted 80% to 125% limits across all comparisons.

Therefore, varying concentrations of alcohol (4%-40% ethanol solution) did not significantly alter the rate and extent of absorption of Formula #1002A amphetamine polistirex (equivalent to 30 mg mixed amphetamine salts), in healthy subjects. The results of this study indicate that the controlled-release properties of formulations according to this invention are maintained in the presence of alcohol.

Example 23

Human Pharmacokinetic Study of a Controlled Release Amphetamine ODT Under Fasted Conditions in Children with ADHD This example describes a single-dose, open-label, single-period, one-treatment study to determine the pharmacokinetic profile of a controlled release ODT preparation of mixed amphetamine polistirex (equivalent to 30 mg mixed amphetamines), in children (6-12 years old). Subjects were children diagnosed with ADHD, and 28 enrolled children were divided into three cohorts (6 of 6-7 years, 11 of 8-9 years, and 11 of 10-12 years).

Following a 10-hour overnight fast, subjects received 1 dose of Test Formulation #1002A (described in Example 21). This dose was administered without water (other than a small mouth rinse (which was not ingested) prior to drug administration) and allowed to disintegrate on the tongue. After dosing, no food was allowed until 4 hours post-dose. No water was to be consumed for 1 hour prior through 1 hour post-dose.

Subjects remained in the research center until completion of the 12-hour blood sampling for the study period and returned for outpatient visits at approximately 24 (Visit 3), 36 (Visit 4), and 48 hours (Visit 5) post-dose in the study period. After the final plasma sample was collected, subjects were permitted to resume taking their usual dose of amphetamines. The final safety visit took place 2 days after dosing as part of Visit 5 (Day 7).

During the study period, 3 mL blood samples were obtained prior to dosing and following the dose at selected times through 48 hours post-dose. Data collection and analysis were carried out as described above. The following PK parameters were determined:

$\lambda Z$: The elimination rate constant ($\lambda Z$) was calculated as the negative of the slope of the terminal log-linear segment of the plasma concentration-time curve; the range of data to be used was determined by visual inspection of a semi-logarithmic plot of concentration versus time.

CL/F: Oral clearance (CL/F) was calculated as:

$$CL/F = D/AUC_{inf},$$

where D was the administered dose.

Vz/F: Volume of distribution in the terminal phase after oral administration (Vz/F) was calculated as:

$$Vz/F = (CL/F)/\lambda Z,$$

Results

Data from 28 enrolled subjects who completed the study were included in the pharmacokinetic and statistical analyses. Mean concentration-time data are showing in FIGS. 34 and 35. Results of the pharmacokinetic and statistical analysis are shown below in Tables 39 and 40.

Figure 34A:
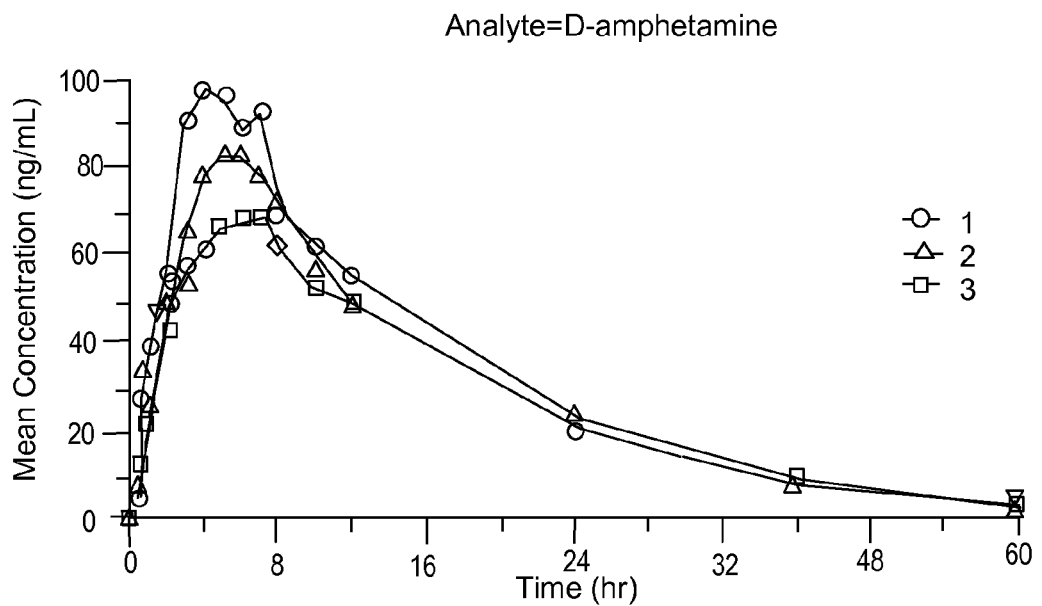
FIGS. 34A and 34B mean d-amphetamine concentration-time profiles after administration of amphetamine-containing ODT for Group 1 (Ages 6-7), Group 2 (Ages 8-9), and Group 3 (Ages 10-12), as described in Example 23.
Figure 34B:
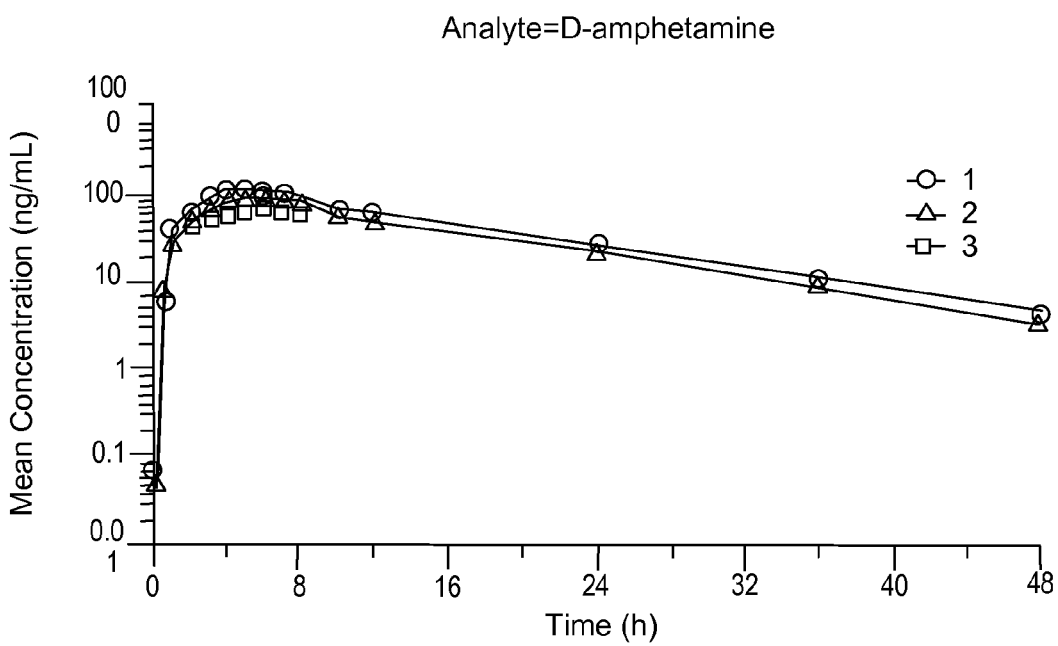

FIGS. 34A and 34B mean d-amphetamine Concentration-Time Profiles after Administration of Formula #1002A ODT for Group 1 (Ages 6-7), Group 2 (Ages 8-9), and Group 3 (Ages 10-12).

Figure 35A:
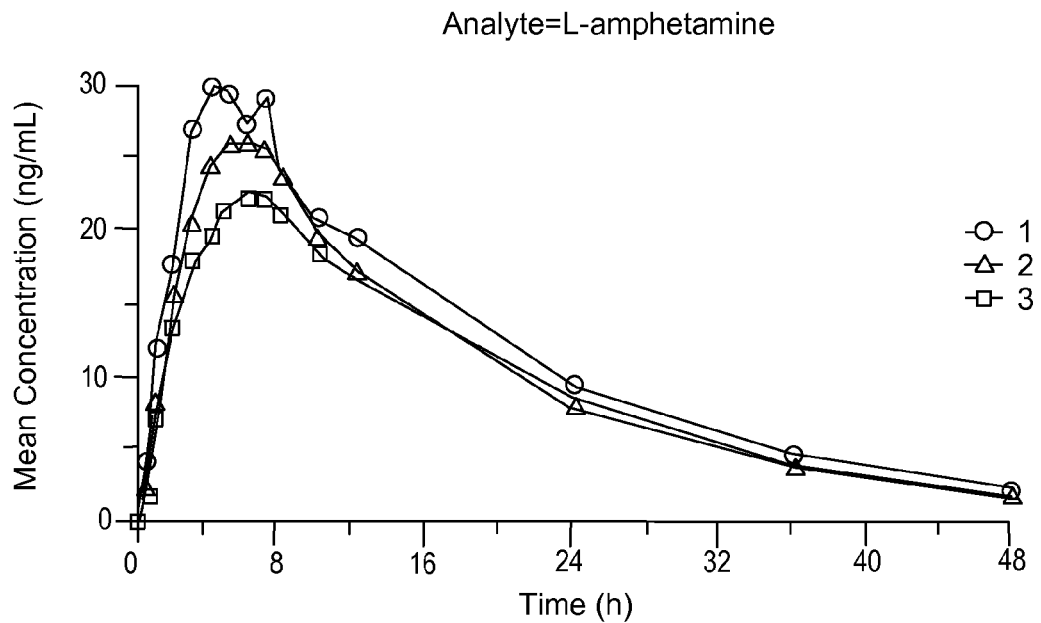
FIGS. 35A and 35B mean d-amphetamine concentration-time profiles after administration of amphetamine-containing ODT for Group 1 (Ages 6-7), Group 2 (Ages 8-9), and Group 3 (Ages 10-12), as described in Example 23.
Figure 35B:
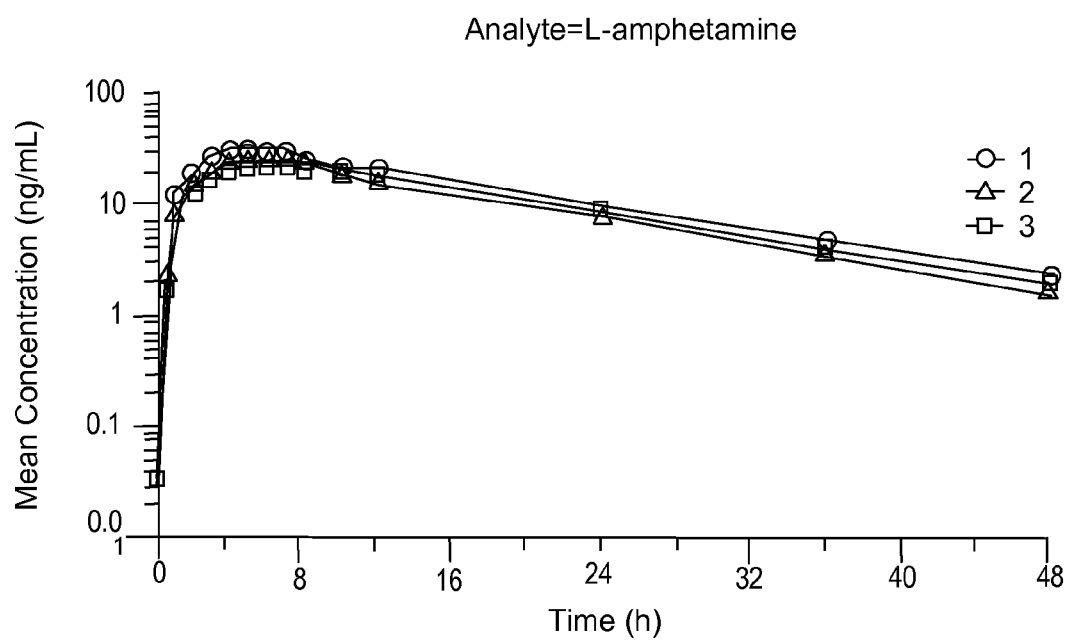

FIGS. 35A and 35B show mean l-amphetamine Concentration-Time Profiles after Administration of Formula #1002A ODT for Group 1 (Ages 6-7), Group 2 (Ages 8-9), and Group 3 (Ages 10-12).

TABLE 39

Statistical Analysis of Weight-Normalized Clearance and Volume of Distribution of d-amphetamine. Supplied as Formula #1002A Age Group 1 (6-7 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 6 | 10.08 | 8.448 | 11.95 | 6.048 | 14.11 |
| CL/F (L/h/kg) | 6 | 0.7619 | 0.6682 | 0.8648 | 0.4571 | 1.067 |

Age Group 2 (8-9 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 11 | 9.177 | 8.284 | 10.28 | 5.506 | 12.85 |
| CL/F (L/h/kg) | 11 | 0.7117 | 0.6371 | 0.8057 | 0.4270 | 0.9964 |

Age Group 3 (10-12 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 11 | 8.678 | 8.064 | 9.396 | 5.207 | 12.15 |
| CL/F (L/h/kg) | 11 | 0.6094 | 0.5349 | 0.7106 | 0.3656 | 0.8532 |

Note:
Target confidence interval range was calculated by multiplying the geometric mean by 0.6 for the 60% lower bound and 1.4 for the 140% upper bound.
Abbreviations: CL/F = oral clearance; CR = controlled release; h = hour; MAR = mixed amphetamine resin; ODT = oral disintegrating tablet; Vz/F = volume of distribution in the terminal phase after oral administration; yrs = years.

TABLE 40

Statistical Analysis of Weight-Normalized Clearance and Volume of Distribution of l-amphetamine Supplied as Formula #1002A Age Group 1 (6-7 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 6 | 32.68 | 26.72 | 39.63 | 19.61 | 45.75 |
| CL/F (L/h/kg) | 6 | 2.137 | 1.840 | 2.466 | 1.282 | 2.992 |

Age Group 2 (8-9 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 11 | 29.63 | 26.46 | 33.65 | 17.78 | 41.48 |
| CL/F (L/h/kg) | 11 | 2.019 | 1.778 | 2.335 | 1.211 | 2.827 |

TABLE 40-continued

Statistical Analysis of Weight-Normalized Clearance and Volume of Distribution of l-amphetamine Supplied as Formula #1002A Age Group 3 (10-12 yrs):

| Parameter | n | Geometric Mean | 95% Confidence Interval | | Target Confidence Interval Range 60%-140% | |
|---|---|---|---|---|---|---|
| | | | Lower Bound | Upper Bound | Lower Bound | Upper Bound |
| Vz/F (L/kg) | 11 | 28.35 | 26.23 | 30.84 | 17.01 | 39.69 |
| CL/F (L/h/kg) | 11 | 1.712 | 1.497 | 2.001 | 1.027 | 2.397 |

Note:
Target confidence interval range was calculated by multiplying the geometric mean by 0.6 for the 60% lower bound and 1.4 for the 140% upper bound.
Abbreviations: CL/F = oral clearance; CR = controlled release; h = hour; MAR = mixed amphetamine resin; ODT = oral disintegrating tablet; Vz/F = volume of distribution in the terminal phase after oral administration; yrs = years.

Conclusions:

There were no unusual or unexpected adverse effects (AEs) related to the study medication. There were no deaths, SAEs, or discontinuations. In general, the nature of the TEAEs reported was consistent with the mechanism of action for these study medications.

An age-related trend in mean maximum and total d-amphetamine and l-amphetamine exposure was observed; as age increased, mean amphetamine exposure decreased. Weight did not appear to be a prominent factor in the observed downward age-related trend in amphetamine exposure.

Mean weight-normalized CL/F and Vz/F values for d-amphetamine and l-amphetamine decreased slightly with an increase in age. Mean $T_{1/2}$ was similar across age groups. Additionally, the geometric means and 95% CIs calculated for d-amphetamine and l-amphetamine CL/F and Vz/F were within the target range of 60% to 140% for each age group.

Example 24

Human Pharmacokinetic Study Using Amphetamine Liquid Formulations and ADDERALL XR Under Fasted Conditions This was a single-dose, open-label, randomized, four-period, four-treatment crossover study that compared the rate of absorption and oral bioavailability of three different amphetamine controlled-release liquid suspensions (equivalent to 30 mg mixed amphetamine salts/15 mL) to an equivalent 30 mg dose of ADDERALL XR capsule, in healthy subjects.

All doses were administered after an overnight fast of at least 10 hours. Each dose administration was separated by a washout period of at least 7 days.

Subjects received the treatments listed below during the four treatment periods:

Treatment A: Test Formulation #1005A controlled-release liquid (shown below). Dose=1×15 mL of suspension. This dose was administered orally without water.

Treatment B: Test Formulation #1005B controlled-release liquid (shown below). Dose=1×15 mL of suspension. This dose was administered orally without water.

Treatment C: Test Formulation #1005C controlled-release liquid (shown below). Dose=1×15 mL of suspension. This dose was administered orally without water.

Treatment D (Reference Product): ADDERALL XR Shire US, Inc. Dose=1×30 mg capsule. This dose was administered orally with 60 mL (2 fl. oz.) of water.

TABLE 41

Test Formulation #1005A (suspension amphetamine with 45% IR and 55% DR)
IR Resin - 36.05% base assay & DR Resin - 7.82% base assay Formula 1005A
(45% active from IR Resin & 55% active from DR Resin)

|  | mg per 15 mL dose | Notes | % |
|---|---|---|---|
| Uncoated (IR) AMP Resin | 23.5 | The 23.5 mg/dose quantity is the | 0.145 |
| Amphetamine (base) | 4.23 | actual amount of IR resin (at a 36.05% | |
| Dextroamphetamine (base) | 4.23 | assay value) that goes into each 15 mL | |
| AMBERLITE IRP069 Resin + Water | 15.04 | dose. | |
|  |  | The values in the gray area are the | |
|  |  | quantities of each material that | |
|  |  | compromise the IR material. | |
| Coated (DR) AMP Resin | 132.2 | The 132.2 mg/dose quantity is the | 0.816 |
| Amphetamine (base) | 5.17 | actual amount of DR resin (at an 7.82% | |
| Dextroamphetamine (base) | 5.17 | assay value) that goes into each 15 mL | |
| AMBERLITE IRP069 Resin + Water | 21.98 | dose. | |
| Humectant | 0.34 | The IR resin material was used to make | |
| EUDRAGIT L100 | 86.74 | the 132.2 mg/dose DR material. | |
| Plasticizer | 12.84 | The values in the gray area are the | |
|  |  | quantities of each material that | |
|  |  | compromise the DR material. | |
| Purified Water | 9839.55 | Each 15 mL dose of liquid suspension | 60.74 |
| Citric Acid | 5.10 | is equivalent to 16.2 grams at the | 0.03 |
| Propylene Glycol | 577.50 | theoretical specific gravity of 1.08. | 3.56 |
| Preservative | 8.55 |  | 0.05 |
| Xanthan Gum | 116.25 |  | 0.72 |
| Vegetable Oil | 33.00 |  | 0.20 |
| Maltitol Syrup | 5400.00 |  | 33.33 |
| Flavor and Color | 4.35 |  | <0.39 |
| Total | 16,200.0 mg |  | 100% |

TABLE 42

Test Formulation #1005B (suspension amphetamine with 45% IR and 55% DR)
IR Resin - 36.05% base assay & DR Resin - 7.82% base assay Formula #1005B
(45% active from IR Resin & 55% active from DR Resin)

|  | mg per 15 mL dose | Notes | % |
|---|---|---|---|
| Uncoated (IR) AMP Resin | 23.5 | The 23.5 mg/dose quantity is the | 0.145 |
| Amphetamine (base) | 4.23 | actual amount of IR resin (at a 36.05% | |
| Dextroamphetamine (base) | 4.23 | assay value) that goes into each 15 mL | |
| AMBERLITE IRP069 Resin + Water | 15.04 | dose. | |
|  |  | The values in the gray area are the | |
|  |  | quantities of each material that | |
|  |  | compromise the IR material. | |
| Coated (DR) AMP Resin | 132.2 | The 132.2 mg/dose quantity is the | 0.816 |
| Amphetamine (base) | 5.17 | actual amount of DR resin (at an 7.82% | |
| Dextroamphetamine (base) | 5.17 | assay value) that goes into each 15 mL | |
| AMBERLITE IRP069 Resin + Water | 21.98 | dose. | |
| Humectant | 0.34 | The IR resin material was used to make | |
| EUDRAGIT L100 | 86.74 | the 132.2 mg/dose DR material. | |
| Plasticizer | 12.84 | The values in the gray area are the | |
|  |  | quantities of each material that | |
|  |  | compromise the DR material. | |
| Purified Water | 11,227.05 | Each 15 mL dose of liquid suspension | 69.30 |
| Citric Acid | 5.10 | is equivalent to 16.2 grams at the | 0.03 |
| Propylene Glycol | 577.50 | theoretical specific gravity of 1.08. | 3.56 |
| Preservative | 8.55 |  | 0.05 |
| Xanthan Gum | 116.25 |  | 0.72 |
| Vegetable Oil | 33.00 |  | 0.20 |
| 70% Sorbitol Solution | 4012.5 |  | 24.77 |
| Flavor and Color | 64.35 |  | <0.39 |
| Total | 16,200.0 mg |  | 100% |

TABLE 43

Test Formulation #1005C (suspension amphetamine with 45% IR and 55% DR)
IR Resin - 36.05% base assay & DR Resin - 7.82% base assay

| | mg per 15 mL dose | Notes | % |
|---|---|---|---|
| Uncoated (IR) AMP Resin | 23.5 | The 23.5 mg/dose quantity is the actual amount of IR resin (at a 36.05% assay value) that goes into each 15 mL dose. The values in the gray area are the quantities of each material that compromise the IR material. | 0.145 |
| Amphetamine (base) | 4.23 | | |
| Dextroamphetamine (base) | 4.23 | | |
| AMBERLITE IRP069 Resin + Water | 15.04 | | |
| Coated (DR) AMP Resin | 132.2 | The 132.2 mg/dose quantity is the actual amount of DR resin (at an 7.82% assay value) that goes into each 15 mL dose. The IR resin material was used to make the 132.2 mg/dose DR material. The values in the gray area are the quantities of each material that compromise the DR material. | 0.816 |
| Amphetamine (base) | 5.17 | | |
| Dextroamphetamine (base) | 5.17 | | |
| AMBERLITE IRP069 Resin + Water | 21.98 | | |
| Humectant | 0.34 | | |
| EUDRAGIT L100 | 86.74 | | |
| Plasticizer | 12.84 | | |
| Purified Water | 11,201.55 | Each 15 mL dose of liquid suspension is equivalent to 16.2 grams at the theoretical specific gravity of 1.08. | 69.15 |
| Citric Acid | 5.10 | | 0.03 |
| Propylene Glycol | 577.50 | | 3.56 |
| Preservative | 8.55 | | 0.05 |
| Xanthan Gum | 116.25 | | 0.72 |
| Vegetable Oil | 33.00 | | 0.20 |
| Sodium Polystyrene Sulfonate | 25.5 | | 0.16 |
| Maltitol Syrup | 4012.5 | | 24.77 |
| Flavor and Color | 64.35 | | <0.39 |
| Total | 16,200.0 mg | | 100% |

Data collection and analysis were carried out as similarly described above. 44 subjects participated in the study with 39 subjects completing all four study periods, and 42 subjects completing at least one test period and the reference period of the study. Data for the 42 subjects were included in the pharmacokinetic and statistical analyses. Mean concentration-time data are showing in FIGS. 36 and 37. Results of the pharmacokinetic and statistical analysis are shown below in Tables 44 through 49.

Figure 36A:
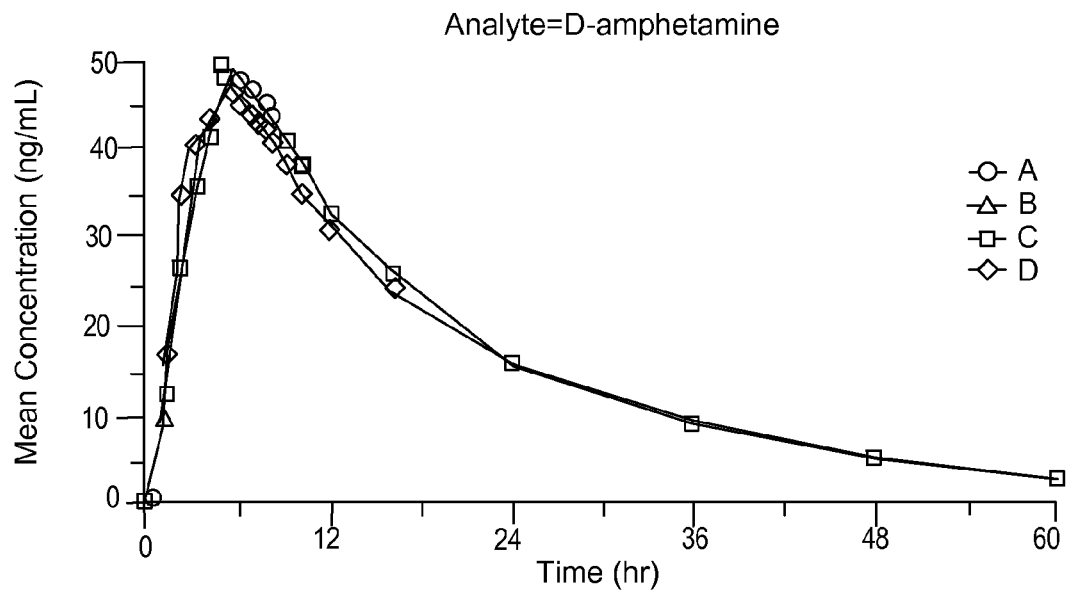
FIGS. 36A and 36B show the mean d-amphetamine concentration-time profiles after administration of Test Formulation #1 (Treatment A), Test Formulation #2 (Treatment B), Test Formulation #3 (Treatment C), and the Reference Product (Treatment D), as described in Example 24.
Figure 36B:
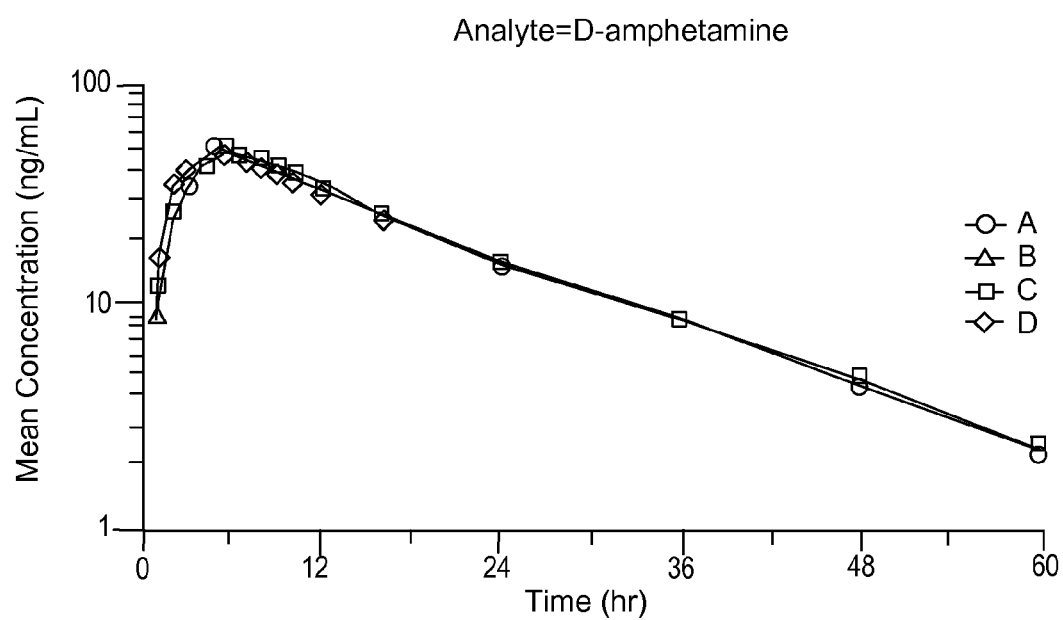

FIGS. 36A and 36B show mean d-amphetamine Concentration-Time Profiles after Administration of Test Formulation #1 (Treatment A), Test Formulation #2 (Treatment B), Test Formulation #3 (Treatment C), and the Reference Product (Treatment D).

Figure 37A:
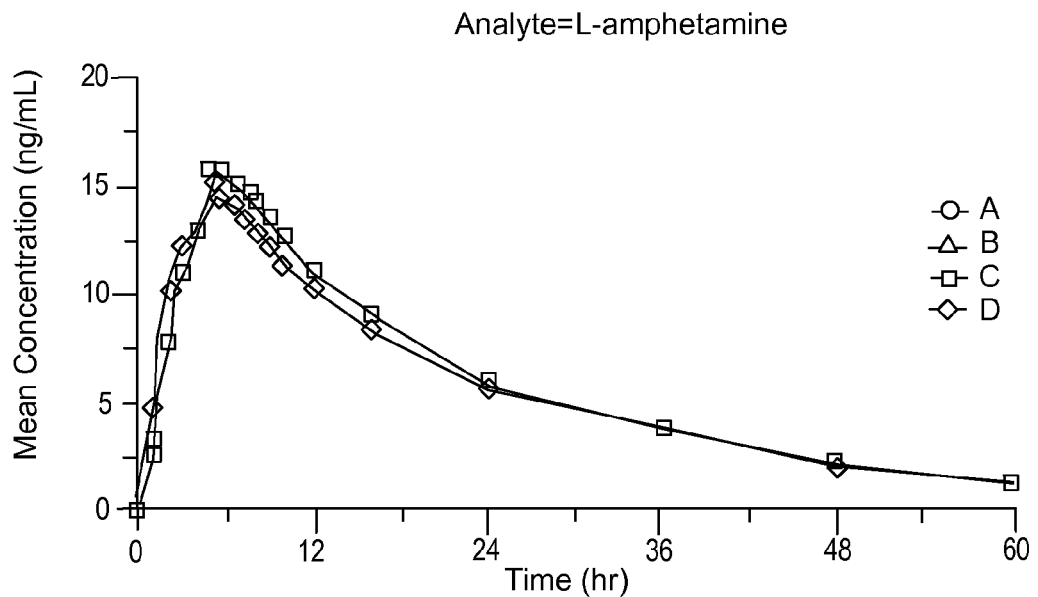
FIGS. 37A and 37B show the mean l-amphetamine concentration-time profiles after administration of Test Formulation #1 (Treatment A), Test Formulation #2 (Treatment B), Test Formulation #3 (Treatment C), and the Reference Product (Treatment D), as described in Example 24.
Figure 37B:
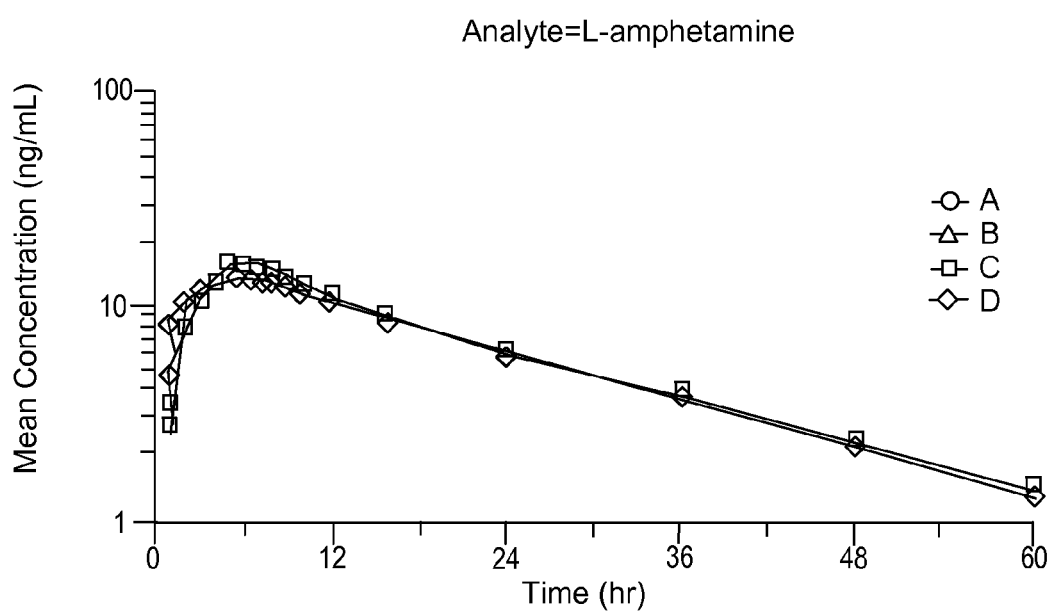

FIGS. 37A and 37B show mean l-amphetamine Concentration-Time Profiles after Administration of Test Formulation #1 (Treatment A), Test Formulation #2 (Treatment B), Test Formulation #3 (Treatment C), and the Reference Product (Treatment D).

TABLE 44

Statistical Analysis of the Log-Transformed Systemic Exposure Parameters of d-amphetamine Comparing Test Formulation #1 (Treatment A) to the Reference Product (Treatment D)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 50.1580 | 49.5786 | 101.17 | 99.16 | 103.22 | 1.0000 | 5.43 |
| $\ln(AUC_{0-5})$ | 130.5315 | 153.2270 | 85.19 | 79.53 | 91.25 | 0.9997 | 18.76 |
| $\ln(AUC_{5-12})$ | 287.7548 | 272.5554 | 105.58 | 103.05 | 108.16 | 1.0000 | 6.56 |
| $\ln(AUC_{5-last})$ | 823.1422 | 791.92221 | 103.94 | 100.64 | 107.35 | 1.0000 | 8.75 |
| $\ln(AUC_{0-24})$ | 696.5164 | 696.4442 | 100.01 | 98.18 | 101.88 | 1.0000 | 5.01 |
| $\ln(AUC_{last})$ | 958.9738 | 951.6525 | 100.77 | 98.40 | 103.19 | 1.0000 | 6.45 |
| $\ln(AUC_{inf})$ | 1001.0534 | 995.6153 | 100.55 | 97.95 | 103.21 | 1.0000 | 7.10 |

[a] Geometric Mean for Test Formulation #1 (Test) and Reference Product (Ref) based on Least Squares Mean of log-transformed parameter values
[b] Ratio(%) = Geometric Mean (Test)/Geometric Mean (Ref)
[c] 90% Confidence Interval

TABLE 45

Statistical Analysis of the Log-Transformed Systemic Exposure Parameters of d-amphetamine Comparing Test Formulation #2 (Treatment B) to the Reference Product (Treatment D)

| Dependent Variable | Geometric Mean[a] Test | Geometric Mean[a] Ref | Ratio (%)[b] (Test/Ref) | 90% CI[c] Lower | 90% CI[c] Upper | ANOVA Power | ANOVA CV % |
|---|---|---|---|---|---|---|---|
| $\ln(C_{max})$ | 50.0963 | 49.3574 | 101.50 | 99.82 | 103.20 | 1.0000 | 4.42 |
| $\ln(AUC_{0-5})$ | 135.9603 | 152.6483 | 89.07 | 84.05 | 94.38 | 1.0000 | 15.45 |
| $\ln(AUC_{5-12})$ | 286.6888 | 271.5835 | 105.56 | 103.52 | 107.64 | 1.0000 | 5.18 |
| $\ln(AUC_{5-last})$ | 821.7640 | 789.8344 | 104.04 | 100.69 | 107.51 | 1.0000 | 8.71 |
| $\ln(AUC_{0-24})$ | 699.0396 | 694.7072 | 100.62 | 98.59 | 102.70 | 1.0000 | 5.41 |
| $\ln(AUC_{last})$ | 960.8482 | 949.2052 | 101.23 | 98.63 | 103.90 | 1.0000 | 6.91 |
| $\ln(AUC_{inf})$ | 1003.0198 | 993.2407 | 100.98 | 98.07 | 103.99 | 1.0000 | 7.79 |

[a]Geometric Mean for Test Formulation #2 (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 46

Statistical Analysis of the Log-Transformed Systemic Exposure Parameters of d-amphetamine Comparing Test Formulation #3 (Treatment C) to the Reference Product (Treatment D)

| Dependent Variable | Geometric Mean[a] Test | Geometric Mean[a] Ref | Ratio (%)[b] (Test/Ref) | 90% CI[c] Lower | 90% CI[c] Upper | ANOVA Power | ANOVA CV % |
|---|---|---|---|---|---|---|---|
| $\ln(C_{max})$ | 50.7295 | 49.3066 | 102.89 | 100.35 | 105.49 | 1.0000 | 6.51 |
| $\ln(AUC_{0-5})$ | 136.5321 | 152.7544 | 89.38 | 84.81 | 94.20 | 1.0000 | 13.75 |
| $\ln(AUC_{5-12})$ | 289.7260 | 271.3370 | 106.78 | 105.26 | 108.31 | 1.0000 | 3.72 |
| $\ln(AUC_{5-last})$ | 829.3721 | 787.7095 | 105.29 | 102.81 | 107.83 | 1.0000 | 6.22 |
| $\ln(AUC_{0-24})$ | 705.8156 | 693.9269 | 101.71 | 99.85 | 103.61 | 1.0000 | 4.82 |
| $\ln(AUC_{last})$ | 970.1670 | 947.3535 | 102.41 | 100.17 | 104.69 | 1.0000 | 5.76 |
| $\ln(AUC_{inf})$ | 1015.0619 | 991.6597 | 102.36 | 99.66 | 105.13 | 1.0000 | 6.96 |

[a]Geometric Mean for Test Formulation #3 (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 47

Statistical Analysis of the Log-Transformed Systemic Exposure Parameters of l-amphetamine Comparing Test Formulation #1 (Treatment A) to the Reference Product (Treatment D)

| Dependent Variable | Geometric Mean[a] Test | Geometric Mean[a] Ref | Ratio (%)[b] (Test/Ref) | 90% CI[c] Lower | 90% CI[c] Upper | ANOVA Power | ANOVA CV % |
|---|---|---|---|---|---|---|---|
| $\ln(C_{max})$ | 15.6903 | 14.9321 | 105.08 | 102.81 | 107.40 | 1.0000 | 5.92 |
| $\ln(AUC_{0-5})$ | 39.6019 | 45.0296 | 87.95 | 81.98 | 94.35 | 0.9996 | 19.20 |
| $\ln(AUC_{5-12})$ | 92.7020 | 85.1083 | 108.92 | 106.39 | 111.52 | 1.0000 | 6.39 |
| $\ln(AUC_{5-last})$ | 302.9169 | 283.7188 | 106.77 | 103.27 | 110.38 | 1.0000 | 9.03 |
| $\ln(AUC_{0-24})$ | 230.3610 | 222.7249 | 103.43 | 101.39 | 105.51 | 1.0000 | 5.40 |
| $\ln(AUC_{last})$ | 344.2092 | 330.7995 | 104.05 | 101.35 | 106.83 | 1.0000 | 7.14 |
| $\ln(AUC_{inf})$ | 373.9861 | 360.6700 | 103.69 | 100.39 | 107.10 | 1.0000 | 8.78 |

[a]Geometric Mean for Test Formulation #1 (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 48

Statistical Analysis of the Log-Transformed Systemic Exposure Parameters of l-amphetamine Comparing Test Formulation #2 (Treatment B) to the Reference Product (Treatment D)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 15.6747 | 14.8460 | 105.58 | 103.86 | 107.33 | 1.0000 | 4.36 |
| $\ln(AUC_{0-5})$ | 41.2088 | 44.8276 | 91.93 | 86.65 | 97.52 | 1.0000 | 15.75 |
| $\ln(AUC_{5-12})$ | 92.3827 | 84.8244 | 108.91 | 106.73 | 111.14 | 1.0000 | 5.37 |
| $\ln(AUC_{5-last})$ | 303.6696 | 283.1073 | 107.26 | 103.43 | 111.24 | 1.0000 | 9.66 |
| $\ln(AUC_{0-24})$ | 231.4482 | 222.2016 | 104.16 | 101.78 | 106.59 | 1.0000 | 6.12 |
| $\ln(AUC_{last})$ | 345.8479 | 330.0470 | 104.79 | 101.67 | 108.00 | 1.0000 | 8.02 |
| $\ln(AUC_{inf})$ | 375.9631 | 360.0332 | 104.42 | 100.75 | 108.23 | 1.0000 | 9.51 |

[a]Geometric Mean for Test Formulation #2 (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 49

Statistical Analysis of the Log-Transformed Systemic Exposure Parameters of l-amphetamine Comparing Test Formulation #3 (Treatment C) to the Reference Product (Treatment D)

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 16.0082 | 14.8077 | 108.11 | 105.08 | 111.23 | 1.0000 | 7.42 |
| $\ln(AUC_{0-5})$ | 41.4033 | 44.8626 | 92.29 | 87.52 | 97.32 | 1.0000 | 13.89 |
| $\ln(AUC_{5-12})$ | 93.3817 | 84.7844 | 110.14 | 108.48 | 111.83 | 1.0000 | 3.97 |
| $\ln(AUC_{5-last})$ | 305.8158 | 282.5814 | 108.22 | 105.23 | 111.30 | 1.0000 | 7.32 |
| $\ln(AUC_{0-24})$ | 233.5886 | 222.0427 | 105.20 | 103.03 | 107.41 | 1.0000 | 5.42 |
| $\ln(AUC_{last})$ | 348.6608 | 329.6149 | 105.78 | 103.04 | 108.59 | 1.0000 | 6.85 |
| $\ln(AUC_{inf})$ | 380.0816 | 359.7935 | 105.64 | 101.93 | 109.48 | 1.0000 | 9.32 |

[a]Geometric Mean for Test Formulation #3 (Test) and Reference Product (Ref) based on Least Squares Mean of log-transformed parameter values
[b]Ratio(%) = Geometric Mean (Test)/Geometric Mean (Ref)
[c]90% Confidence Interval Conclusions There were no unusual or unexpected adverse events related to the study medication. The 90% confidence interval for comparing the maximum exposure, based on $\ln(C_{max})$, is within the accepted 80% to 125% limits for all comparisons and analytes.

The 90% confidence intervals for comparing total systemic exposure, based on $\ln(AUC_{last})$ and $\ln(AUC_{inf})$, are within the accepted 80% to 125% limits for all comparisons and analytes.

With the exception of the log-transformed $AUC_{0-5}$ Test Formulation #1005A vs. reference comparison for d-amphetamine, all log-transformed partial AUC parameters were within the accepted 80% to 125% range across all treatment comparisons and analytes. The lower bound of the 90% confidence interval for the log-transformed $AUC_{0-5}$ Test Formulation #1005A vs. reference comparison was 79.53%, slightly below 80% for d-amphetamine.

Therefore, Test Formulations #1005B and #1005C (equivalent to 30 mg mixed amphetamine salts/15 mL) are bioequivalent to ADDERALL XR under fasted conditions.

Test Formulation #1005A (equivalent to 30 mg mixed amphetamine salts/15 mL) is bioequivalent to ADDERALL XR under fasted conditions based on standard bioequilvance metrics ($C_{max}$, $AUC_{last}$, $AUC_{inf}$) and additional metrics such as $AUC_{5-12}$, $AUC_{5-last}$, and $AUC_{0-24}$; bioequilvance criteria were not met for $AUC_{0-5}$ for d-amphetamine.

Example 25

Rate of Absorption and Oral Bioavailability of Mixed Amphetaminers in Oral Liquid Suspension Compared to the Commercially Available Reference Product, Adderall XR This was an open-label, single-dose, 3-treatment, 3-period, randomized, crossover study to assess the effect of food on the rate of absorption and oral bioavailability of mixed amphetamines on ion exchange resin in oral liquid suspension. The oral liquid suspension is similar to the suspension described in Example 24. Subjects were randomly assigned to a treatment sequence and received three separate single-dose administrations of study medication, one treatment per period, according to the randomization schedule. Dosing days were separated by a washout period of at least 7 days. Subjects received each of the treatments listed below during the three treatment periods:

Treatment A: Test Formulation 25A, an Oral Liquid suspension (equivalent to 30 mg mixed amphetamine salts/15 mL) was administered under fasted conditions; Dose=1×15 mL liquid oral suspension.

Treatment B: Test Formulation 25B, an Oral Liquid Suspension (equivalent to 30 mg mixed amphetamine salts/15 mL) was administered under fed conditions; Dose=1×15 mL liquid oral suspension.

Treatment C: Reference Product 25C, an Adderall XR® administered under fed conditions; Dose=1×30 mg capsule.

In each study period, subjects were admitted to the study unit in the evening prior to the scheduled dose. Subjects were confined to the research center during each study period until completion of the 36-hour blood collection and other study procedures. Subjects returned to the study unit for outpatient pharmacokinetic blood samples at 48 and 60 hours.

Procedures for Collecting Samples for Pharmacokinetic Analysis

Blood samples (1×4 mL) were collected and analyzed for d- and l-amphetamine. Samples were analyzed as described above. The following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to 5.00 hours ($AUC_{0-5}$), area under the concentration-time curve from 5.00 hours to the time of the last quantifiable concentration ($AUC_{5-last}$), area under the concentration-time curve from time-zero to the time of the last quantifiable concentration ($AUC_{last}$), and area under the plasma concentration time curve from time-zero extrapolated to infinity ($AUC_{inf}$).

To assess the bioequivalence for Treatment B (fed) vs. Adderall XR (Treatment C, fed), an analysis of variance (ANOVA) model and the two one-sided t-tests procedure was performed on the log-transformed pharmacokinetic parameters $C_{max}$, $AUC_{0-5}$, $AUC_{5-last}$, and $AUC_{inf}$ for d- and l-amphetamine across treatments. Bioequivalence was demonstrated if the 90% confidence intervals were within the accepted limits of 80.00 to 125.00%.

To assess the effect of food on the rate and extent of absorption of Treatment B (fed) vs. Treatment A (fast), an analysis of variance (ANOVA) model and the two one-sided t-tests procedure was performed on the log-transformed pharmacokinetic parameters $C_{max}$, $AUC_{last}$, and AUC, for d- and l-amphetamine across treatments. No significant food effect was demonstrated if the 90% confidence intervals were within the accepted limits of 80.00 to 125.00%.

Results

Figure 38A:
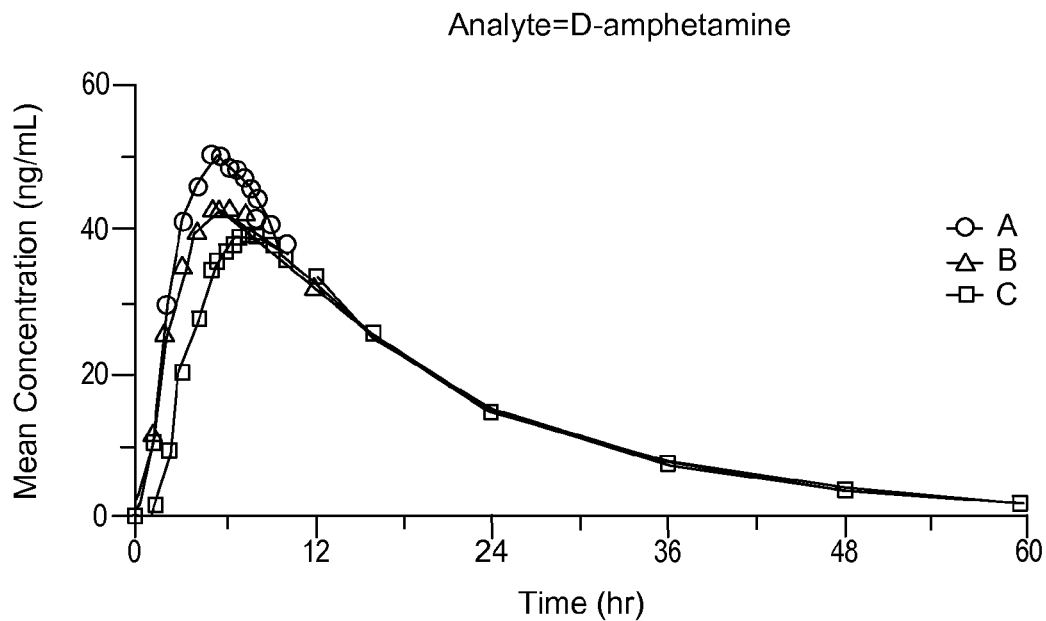
FIG. 38A is a linear graph of the mean concentration time profiles for d-amphetamine following: administration of suspension under fasted conditions (Treatment A), administration of suspension under fed conditions (Treatment B), and administration of reference product under fed conditions (Treatment C).
Figure 38B:
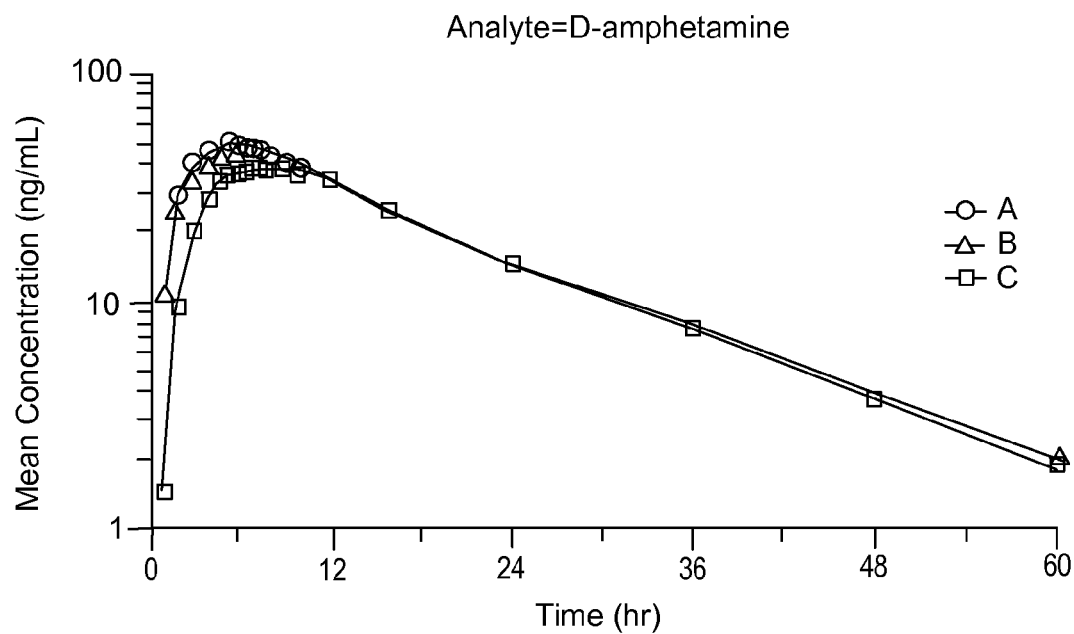
FIG. 38B is a semi-log scale graph of the mean concentration time profiles for d-amphetamine following: administration of suspension under fasted conditions (Treatment A), administration of suspension under fed conditions (Treatment B), and administration of reference product under fed conditions (Treatment C).
Figure 39A:
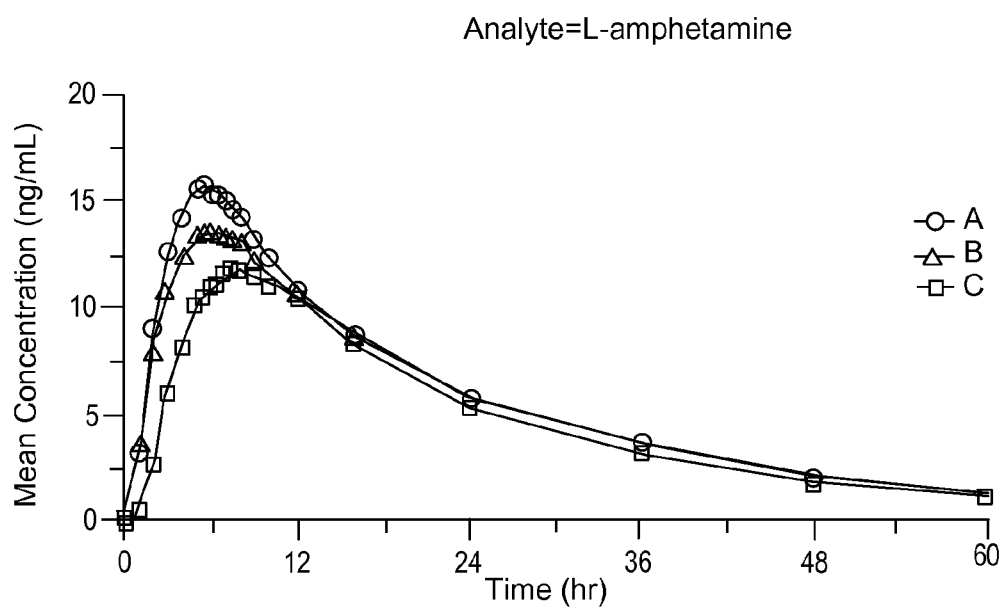
FIG. 39A is a linear graph of the mean concentration time profiles for l-amphetamine following: administration of suspension under fasted conditions (Treatment A), administration of suspension under fed conditions (Treatment B), and administration of reference product under fed conditions (Treatment C).
Figure 39B:
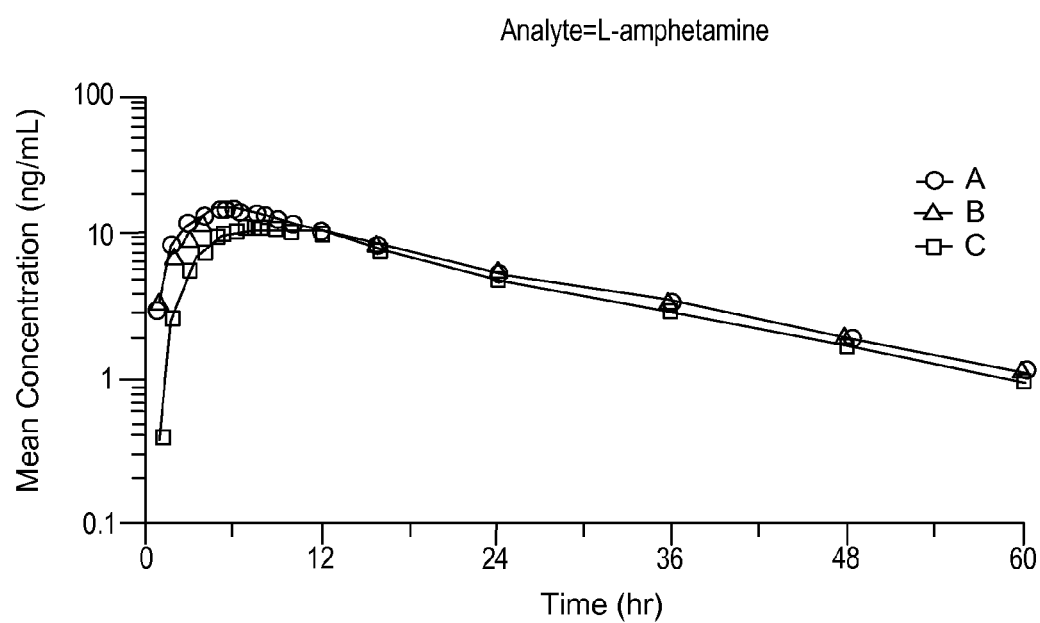
FIG. 39B is a semi-log scale graph of the mean concentration time profiles for l-amphetamine following: administration of suspension under fasted conditions (Treatment A), administration of suspension under fed conditions (Treatment B), and administration of reference product under fed conditions (Treatment C).

Data from 29 subjects were included in the pharmacokinetic and statistical analyses. Mean concentration-time data are shown in FIGS. 38 and 39. Results of the pharmacokinetic and statistical analyses are shown below in Tables 50 through 53.

Conclusions

Bioequivalence Assessment (Treatment B, (Fed) Vs. Adderall XR (Treatment C, (Fed))

The 90% confidence interval for comparing the maximum exposure, based on $\ln(C_{max})$, is within the accepted 80% to 125% limits for d- and l-amphetamine. The 90% confidence intervals for comparing late and total systemic exposure, based on $\ln(AUC_{5-last})$ and $\ln(AUC_{inf})$, are within the accepted 80% to 125% limits for d- and l-amphetamine. The 90% confidence intervals for comparing early systemic exposure, based on $\ln(AUC_{0-5})$ are not within the accepted 80% to 125% limits for either d- and l-amphetamine. Therefore, a formulation of mixed amphetamine resin Oral Liquid Suspension (equivalent to 30 mg mixed amphetamine salts/15 mL) is not bioequivalent to the reference listed drug product (RLD) Adderall XR under fed conditions. Rather, formulating amphetamines in a suspension of drug-resin particles maintains an early onset of amphetamine effect, even when taken with meals.

Food Effect Assessment (Treatment B, Fed) Vs. (Treatment A, Fast))

The 90% confidence interval for comparing the maximum exposure, based on $\ln(C_{max})$, is within the accepted 80% to 125% limits for d- and l-amphetamine. The 90% confidence intervals for comparing total systemic exposure, based on $\ln(AUC_{last})$ and $\ln(AUC_{inf})$, are within the accepted 80% to 125% limits for d- and l-amphetamine. Therefore, no significant food effect was demonstrated for the formulations of Oral Liquid Suspension containing mixed amphetamines on resin particles (equivalent to 30 mg mixed amphetamine salts/15 mL). Such suspensions provide amphetamine exposure levels that more closely resemble the fasted state, even when taken with meals.

TABLE 50

Statistical Analysis of the Log-Transformed Systemic Exposure Parameters of d-Amphetamine Comparing Fed Conditions (Treatment B) to the Reference Product under Fed Conditions (Treatment C)

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 45.2535 | 41.6470 | 108.66 | 103.14 | 114.47 | 1.0000 | 11.66 |
| $\ln(AUC_{0-5})$ | 125.0648 | 72.1095 | 173.44 | 145.51 | 206.73 | 0.6764 | 40.70 |
| $\ln(AUC_{5-last})$ | 773.0222 | 757.8067 | 102.01 | 97.59 | 106.63 | 1.0000 | 9.90 |
| $\ln(AUC_{inf})$ | 945.7804 | 866.6134 | 109.14 | 104.84 | 113.61 | 1.0000 | 8.97 |

[a]Geometric Mean for Treatment B, Fed (Test) and Reference Product-Fed (Ref) based on Least Squares Mean of log-transformed parameter values
[b]Ratio(%) = Geometric Mean (Test)/Geometric Mean (Ref)
[c]90% Confidence Interval

TABLE 51

Statistical Analysis of the Log-Transformed Systemic Exposure Parameters of d-Amphetamine Comparing Fed Conditions (Treatment B) to Fasted Conditions (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($C_{max}$) | 45.3087 | 51.0913 | 88.68 | 85.41 | 92.08 | 1.0000 | 8.40 |
| ln($AUC_{last}$) | 909.6180 | 942.7716 | 96.48 | 93.20 | 99.89 | 1.0000 | 7.74 |
| ln($AUC_{inf}$) | 945.6631 | 977.1454 | 96.78 | 93.30 | 100.39 | 1.0000 | 8.19 |

[a]Geometric Mean for Treatment B, Fed (Test) and Treatment A Fasted (Ref) based on Least Squares Mean of log-transformed parameter values
[b]Ratio(%) = Geometric Mean (Test)/Geometric Mean (Ref)
[c]90% Confidence Interval

TABLE 52

Statistical Analysis of the Log-Transformed Systemic Exposure Parameters of l-Amphetamine Comparing Fed Conditions (Treatment B) to the Reference Product under Fed Conditions (Treatment C)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($C_{max}$) | 14.3840 | 12.5275 | 114.82 | 109.16 | 120.78 | 1.0000 | 11.32 |
| ln($AUC_{0-5}$) | 38.7444 | 20.9999 | 184.50 | 154.35 | 220.53 | 0.6642 | 41.41 |
| ln($AUC_{5-last}$) | 281.9542 | 258.7635 | 108.96 | 103.88 | 114.29 | 1.0000 | 10.68 |
| ln($AUC_{inf}$) | 349.4520 | 301.4583 | 115.92 | 110.57 | 121.53 | 1.0000 | 10.56 |

[a]Geometric Mean for Treatment B, Fed (Test) and Reference Product-Fed (Ref) based on Least Squares Mean of log-transformed parameter values
[b]Ratio(%) = Geometric Mean (Test)/Geometric Mean (Ref)
[c]90% Confidence Interval

TABLE 53

Statistical Analysis of the Log-Transformed Systemic Exposure Parameters of l-Amphetamine Comparing Fed Conditions (Treatment B) to Fasted Conditions (Treatment A)

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($C_{max}$) | 14.3990 | 16.0658 | 89.63 | 86.43 | 92.94 | 1.0000 | 8.11 |
| ln($AUC_{last}$) | 324.6557 | 338.2024 | 95.99 | 92.54 | 99.58 | 1.0000 | 8.19 |
| ln($AUC_{inf}$) | 349.3468 | 361.6533 | 96.60 | 92.75 | 100.61 | 1.0000 | 9.09 |

[a]Geometric Mean for Treatment B, Fed (Test) and Treatment A, Fasted (Ref) based on Least Squares Mean of log-transformed parameter values
[b]Ratio(%) = Geometric Mean (Test)/Geometric Mean (Ref)
[c]90% Confidence Interval All documents (e.g., patents and published patent applications) mentioned in this specification are hereby incorporated by reference in their entirety.

The invention claimed is:

1. A pharmaceutical composition comprising an ADHD effective agent complexed with ion-exchange resin particles to form drug-resin particles,
    wherein said ADHD effective agent is methylphenidate,
    wherein said composition comprises a first plurality of drug-resin particles that provide for immediate release of said ADHD effective agent and a second plurality of drug-resin particles that are coated with a triggered-release coating triggered by a pH change and a diffusion barrier coating, and
    wherein administration of the composition to a human produces a mean plasma concentration profile for d-methylphenidate in human subjects which has one or more parameters selected from the group consisting of $AUC_{0-3}$, $AUC_{0-5}$, $AUC_{0-Tmax}$, $AUC_{5-12}$, $AUC_{5-24}$, $AUC_{Tmax-24}$, $AUC_{Tmax-12}$, $AUC_{5-t}$, $AUC_{Tmax-t}$, $AUC_{0-24}$, and $AUC_{0-\infty}$ which is substantially similar to those parameters of at least one of the in vivo serum profiles of the compositions comprising methylphenidate-containing drug-resin particles shown in FIG. 20A.

2. The composition of claim 1, wherein the triggered-release coating is cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters, co-polymerized methacrylic acid/acrylic acid ethyl esters, or mixtures thereof.

3. The composition of claim 2, wherein the composition additionally contains polistirex, polacrilex, cholestyramine, polacrilin or mixtures thereof.

4. The composition of claim 1, wherein the diffusion barrier coating contains polyvinylpyrrolidone, polyvinylacetate, polyvinylalcohol or mixtures thereof.

5. The composition of claim 1, wherein the diffusion barrier coating is a water insoluble, water permeable membrane.

6. The composition of claim 5, wherein the water insoluble, water permeable membrane is ethylcellulose.

7. The composition of claim 1, wherein the triggered-release coating covers the diffusion barrier coating.

8. The composition of claim 7, wherein the diffusion barrier coating is ethylcellulose.

9. The composition of claim 1, wherein the resin particles are strong acidic cation exchange resins, selected from the group consisting of polistirex, polacrilex, cholestyramine, polacrilin and mixtures thereof.

10. The composition of claim 1, wherein said first plurality of particles comprise 20%-30% by number of the drug-resin particles present in said composition and said second plurality of particles comprise 70%-80% by number of the drug-resin particles present in said composition.

11. The composition of claim 8, wherein said first plurality of particles comprise about 25% by number of the drug-resin particles present in said composition and said second plurality of particles comprise about 75% by number of the drug-resin particles present in said composition.

12. The composition of claim 1, wherein the composition is a liquid suspension, chewable composition, or an orally disintegrating tablet composition.

13. The composition of claim 1, wherein the amount of methylphenidate is 10-60 mg.

14. The composition of claim 1, wherein the composition has an in vitro dissolution profile wherein 30-33% by weight of the ADHD effective agent is released from the drug-resin particles within the first 30 minutes, 34-42% by weight of the agent is released within 2 hours, 40-80% of the agent is released within 4 hours, and 80-100% by weight of the agent is released within 24 hours, wherein the dissolution profile is determined by an in vitro dissolution assay, wherein the conditions of the dissolution assay are an initial dissolution medium of 0.1 N HCl, and after 2 hours, the medium is adjusted to a pH of about 6.8; and the dissolution assay is performed using a USP Apparatus 2.

15. The composition of claim 1, wherein the composition has an in vivo serum profile that is statistically similar to at least one profile selected from FIGS. 27A, 27B, 28A, and 28B.

16. The composition of claim 1, wherein a mammal receiving said composition, in the presence of ethanol, is exposed to a reduced amount of methylphenidate compared to an extended release composition without resin particles comprising methylphenidate hydrochloride.

17. The composition of claim 1, wherein the amount of said methylphenidate in said composition is equivalent to the amount present in a 10 mg, 20 mg, 30 mg, 40 mg, 50 mg or 60 mg dose of methylphenidate hydrochloride.

18. The composition of claim 1, wherein said composition is an orally disintegrating tablet and is effective to provide a mean plasma concentration profile in human adult ADHD patients which has an $AUC_{0-3}$ of 20.53 ng hr/mL −20%/+25% and a $C_{max}$ of 20.17 ng/mL −20%/+25% for d-methylphenidate, an $AUC_{0-3}$ of 0.62 ng hr/mL −20%/+25% and a $C_{max}$ of 0.44 ng/mL −20%/+25% for l-methylphenidate, and/or an $AUC_{0-3}$ of 21.29 ng hr/mL −20%/+25% and a $C_{max}$ of 20.60 ng/mL −20%/+25% for total methylphenidate, for a total methylphenidate dose that is equivalent to the amount present in a 60 mg total dose of methylphenidate hydrochloride, or respective AUC and $C_{max}$ values directly proportional thereto for a total methylphenidate dose other than that which is equivalent to the amount present in a 60 mg total dose of methylphenidate hydrochloride.

19. The composition of claim 1, wherein said composition is an orally disintegrating tablet and is effective to provide a mean plasma concentration profile in human adult ADHD patients which has an $AUC_{0-5}$ of 50.16 ng hr/mL −20%/+25% and a $C_{max}$ of 20.17 ng/mL −20%/+25% for d-methylphenidate, an $AUC_{0-5}$ of 1.07 ng hr/mL −20%/+25% and a $C_{max}$ of 0.44 ng/mL −20%/+25% for l-methylphenidate, and/or an $AUC_{0-5}$ of 51.43 ng hr/mL −20%/+25% and a $C_{max}$ of 20.60 ng/mL −20%/+25% for total methylphenidate, for a total methylphenidate dose that is equivalent to the amount present in a 60 mg total dose of methylphenidate hydrochloride, or respective AUC and $C_{max}$ values directly proportional thereto for a total methylphenidate dose other than that which is equivalent to the amount present in a 60 mg total dose of methylphenidate hydrochloride.

20. The composition of claim 1, wherein said composition is an orally disintegrating tablet and is effective to provide a mean plasma concentration profile in human adult ADHD patients which has an $AUC_{5-24}$ of 103.84 ng hr/mL −20%/+25% and a $C_{max}$ of 20.17 ng/mL −20%/+25% for d-methylphenidate, an $AUC_{5-24}$ of 0.96 ng hr/mL −20%/+25% and a $C_{max}$ of 0.44 ng/mL −20%/+25% for l-methylphenidate, and/or an $AUC_{5-24}$ of 105.07 ng hr/mL −20%/+25% and a $C_{max}$ of 20.60 ng/mL −20%/+25% for total methylphenidate, for a total methylphenidate dose that is equivalent to the amount present in a 60 mg total dose of methylphenidate hydrochloride, or respective AUC and $C_{max}$ values directly proportional thereto for a total methylphenidate dose other than that which is equivalent to the amount present in a 60 mg total dose of methylphenidate hydrochloride.

21. The composition of claim 1, wherein said composition is an orally disintegrating tablet and is effective to provide a mean plasma concentration profile in human adult ADHD patients which has an $AUC_{0-24}$ of 156.72 ng hr/mL −20%/+25% and a $C_{max}$ of 20.17 ng/mL −20%/+25% for d-methylphenidate, an $AUC_{0-24}$ of 2.19 ng hr/mL −20%/+25% and a $C_{max}$ of 0.44 ng/mL −20%/+25% for l-methylphenidate, and/or an $AUC_{0-24}$ of 159.25 ng hr/mL −20%/+25% and a $C_{max}$ of 20.60 ng/mL −20%/+25% for total methylphenidate, for a total methylphenidate dose that is equivalent to the amount present in a 60 mg total dose of methylphenidate hydrochloride, or respective AUC and $C_{max}$ values directly proportional thereto for a total methylphenidate dose other than that which is equivalent to the amount present in a 60 mg total dose of methylphenidate hydrochloride.

22. The composition of claim 1, wherein said composition, would produce, in a human adult, a mean plasma concentration versus time curve (ng/ml versus hours) having an area under the curve ($AUC_{0-\infty}$) of about 160 ng hr/ml to about 180 ng hr/ml for total methylphenidate when said composition contains a total methylphenidate dose that is equivalent to that present in about a 60 mg total dose of methylphenidate hydrochloride.

23. The composition of claim 1, wherein one or more in vivo pharmacokinetic parameters of the composition selected from the group consisting of $C_{max}$, $AUC_{0-3}$, $AUC_{0-5}$, $AUC_{0-Tmax}$, $AUC_{5-12}$, $AUC_{5-24}$, $AUC_{Tmax-24}$, $ACU_{Tmax-12}$, $AUC_{5-t}$, $AUC_{Tmax-t}$, $AUC_{0-24}$, and $AUC_{0-\infty}$ have a 90% confidence interval with upper and lower bounds within a range from 90%-115% of the value of the same parameter(s) for a bioequivalent reference composition.

24. The composition of claim 1, wherein said composition has an in vivo serum profile with a $T_{max}$ of approximately six hours.

25. The composition of claim 24, wherein said composition has a bimodal profile with two peaks, having a first peak at approximately 3 hours.

26. The composition of claim 1, wherein said composition has an in vivo serum profile with a first and second peak and said second peak is the $C_{max}$.

27. The composition of claim 1, wherein a dose of said composition comprising a total amount of said methylphenidate that is equivalent to that present in about a 60 mg total dose of methylphenidate hydrochloride produces a $C_{max}$ greater than 16.55 ng/mL.

28. The composition of claim 1, wherein said first plurality of drug-resin particles is uncoated.

* * * * *